(12) United States Patent
Pines et al.

(10) Patent No.: US 7,385,395 B2
(45) Date of Patent: Jun. 10, 2008

(54) APPARATUS FOR PREPARING A SOLUTION OF A HYPERPOLARIZED NOBLE GAS FOR NMR AND MRI ANALYSIS

(75) Inventors: Alexander Pines, Berkeley, CA (US); Thomas Budinger, Berkeley, CA (US); Gil Navon, Ramat Gan (IL); Yi-Qiao Song, Berkeley, CA (US); Stephan Appelt, Waiblingen (DE); Angelo Bifone, Rome (IT); Rebecca Taylor, Berkeley, CA (US); Boyd Goodson, Berkeley, CA (US); Roberto Seydoux, Berkeley, CA (US); Toomas Room, Albany, CA (US); Tanja Pietrass, Socorro, NM (US)

(73) Assignee: Lawrence Berkeley National Laboratory, Berkeley, CA (US)

( * ) Notice: Subject to any disclaimer, the term of this patent is extended or adjusted under 35 U.S.C. 154(b) by 491 days.

(21) Appl. No.: 10/940,297

(22) Filed: Sep. 13, 2004

(65) Prior Publication Data

US 2005/0030026 A1 Feb. 10, 2005

Related U.S. Application Data

(62) Division of application No. 10/164,324, filed on Jun. 5, 2002, now Pat. No. 6,818,202, which is a division of application No. 08/825,475, filed on Mar. 28, 1997, now Pat. No. 6,426,058.

(60) Provisional application No. 60/014,321, filed on Mar. 29, 1996.

(51) Int. Cl.
   G01V 3/00 (2006.01)
   G01N 24/00 (2006.01)
   A61B 5/055 (2006.01)

(52) U.S. Cl. ...................... 324/301; 324/307; 436/173; 424/9.3

(58) Field of Classification Search ...................... None
   See application file for complete search history.

(56) References Cited

U.S. PATENT DOCUMENTS 4,586,511 A 5/1986 Clark, Jr.

(Continued)

FOREIGN PATENT DOCUMENTS

EP 0620 447 A2 4/1994

(Continued)

OTHER PUBLICATIONS

Albert, M.S. et al., "Biological Magnetic Resonance Imaging Using Laser-Polarized 129-Xe," Letters to Nature, vol. 330, No. 21, pp. 199-201 (1994).

(Continued)

Primary Examiner—Yelena G. Gakh
(74) Attorney, Agent, or Firm—Knobbe, Martens, Olson & Bear LLP

(57) ABSTRACT

The present invention relates generally to nuclear magnetic resonance (NMR) techniques for both spectroscopy and imaging. More particularly, the present invention relates to methods in which hyperpolarized noble gases (e.g., Xe and He) are used to enhance and improve NMR and MRI. Additionally, the hyperpolarized gas solutions of the invention are useful both in vitro and in vivo to study the dynamics or structure of a system. When used with biological systems, either in vivo or in vitro, it is within the scope of the invention to target the hyperpolarized gas and deliver it to specific regions within the system.

25 Claims, 20 Drawing Sheets

U.S. PATENT DOCUMENTS

| | | | |
|---|---|---|---|
| 5,357,959 A | | 10/1994 | Fishman |
| 5,545,396 A | * | 8/1996 | Albert et al. ............... 424/9.3 |
| 5,642,625 A | | 7/1997 | Cates, Jr. et al. |
| 5,665,777 A | | 9/1997 | Fesik et al. |
| 5,688,486 A | | 11/1997 | Watson et al. |
| 5,698,401 A | | 12/1997 | Fesik et al. |
| 5,773,024 A | | 6/1998 | Unger et al. |
| 5,785,953 A | | 7/1998 | Albert et al. |
| 5,804,390 A | | 9/1998 | Fesik et al. |
| 5,809,801 A | * | 9/1998 | Cates et al. ................... 62/637 |
| 5,846,517 A | | 12/1998 | Unger |
| 5,891,643 A | | 4/1999 | Fesik et al. |
| 5,989,827 A | | 11/1999 | Fesik et al. |
| 6,023,162 A | | 2/2000 | Johnson |
| 6,042,809 A | | 3/2000 | Tournier et al. |
| 6,043,024 A | | 3/2000 | Fesik et al. |
| 6,051,208 A | | 4/2000 | Johnson et al. |
| 6,071,494 A | | 6/2000 | Unger |
| 6,278,893 B1 | | 8/2001 | Ardenkjaer-Larson et al. |
| 6,288,261 B1 | | 9/2001 | Augeri et al. |
| 6,426,058 B1 | | 7/2002 | Pines et al. |
| 6,453,188 B1 | | 9/2002 | Ardenkjaer-Larsen et al. |

FOREIGN PATENT DOCUMENTS

| | | |
|---|---|---|
| WO | WO 95/27438 | 10/1995 |
| WO | WO 96/08234 | 3/1996 |
| WO | WO 96/28090 | 9/1996 |
| WO | WO 97/37239 | 10/1997 |
| WO | WO 98/18500 | 5/1998 |
| WO | WO 98/42383 | 10/1998 |
| WO | WO 00/25828 | 5/2000 |
| WO | WO 00/53229 | 9/2000 |

OTHER PUBLICATIONS

Albert, Mitchell S. et al., "129 Xe Relaxation Catalysis by Oxygen," 11th Annual Meeting Society of Magnetic Resonance in Medicine, pp. 4710 (1992).

Albert, Mitchell S. et al., "Measurement of 129-Xe T1 in Blood to Explore the Feasibility of Hyperpolarized 129-Xe MRI," Journal of Computer Assisted Tomography, vol. 19, No. 6, pp. 975-978, Nov./Dec. 1995.

Albert, Mitchell S. et al., "Relaxation of 129-Xe In Model Biological Systems: On Probing the Mechanism of General Anesthesia," 11th Annual Meeting Society of Magnetic Resonance in Medicine, pp. 2104 (1992).

Andrew, E.R. et al., "Possibilities for High-Resolution Nuclear Magnetic Resonance Spectra of Crystals," Discussions of the Faraday Society, High Resolution Nuclear Magnetic Resonance, vol. 34, pp. 38-42 (1962).

Ardelean, Ioan et al., "The Nutation Spin Echo and Its Use for Localized NMR," Journal of Magnetic Resonance, vol. 146, pp. 43-48 (2000).

Augustine, Matthew P. et al., "Low Field Magnetic Resonance Images of Polarized Noble Gases Obtained with a dc Superconducting Quantum Interference Device," Applied Physics Letters, vol. 72, No. 15, pp. 1908-1910, Apr. 13, 1998.

Balbach, John et al., "High-Resolution NMR in Inhomogeneous Fields," Chemical Physics Letters, vol. 277, pp. 367-374 (1997).

Bhaskar, N.D. and Happer, W., "Efficiency of Spin Exchange between Rubidium Spins and 129 Xe Nuclei in a Gas,".

Bifone, A. et al., "NMR of Laser-Polarized Xenon in Human Blood,"Proc. Natl. Acad. Sci, vol. 93, pp. 12932-12936, Nov. 1996.

Bowers et al., "Exploring Surfaces and Cavities in Lipoxygenase and Other Proteins by Hyperpolarized Xenon-129 NMR," JACS, vol. 121, pp. 9370-9377 (1999).

Brotin et al., "129- Xenon NMR Spectroscopy of Deuterium-Labeled Cryptophane-A Xenon Complexes," J ACS, vol. 122, pp. 1171-1174 (2000).

Carver, Thomas R. et al., "Experimental Verification of the Overhauser Nuclear Polarization Effect," Physical Review, vol. 102, No. 4, pp. 975-980, May 15, 1956.

Carver, Thomas R., "Optical Pumping," Science, vol. 141, No. 3581, pp. 599-608, Aug. 16, 1963.

Checovich et al., Fluorescence Polarization-A New Tool for Cell Molecular Biology, Nature, vol. 375, pp. 254-256, May 18, 1995.

Chmelka, B.F. & Pines, A., "Some Developments in Nuclear Magnetic Resonance of Solids," Science, vol. 246, Issue 4926, pp. 71-77, Oct. 6, 1989.

de Swiet, Thomas M. et al., "In Situ Analysis of Fluids Contained in Sedimentary Rock," Journal of Magnetic Resonance, vol. 133, pp. 385-387 (1998).

Diehl, P. and Jokisaari, J., "Nuclear Magnetic Relaxation of the 129-Xe and 131-Xe Isotopes of Xenon Gas Dissolved in Isotropic and Anisotropic Liquids," Journal of Magnetic Resonance, vol. 88, pp. 660-665 (1990).

Gehring, Kalle et al., "An NMR Study of Ligand Binding by Maltodextrin Binding Protein," Biochem. Cell Biol., vol. 76, pp. 189-197 (1998).

Hall, Jason A. et al., "Two Modes of Ligand Binding in Maltose-Binding Protein of *Escherichia coli*," Journal of Biological Chemistry, vol. 272, No. 28, pp. 17605-17609, Jul. 1997.

Hall, Laurance D. et al., "Measurement of High-Resolution NMR Spectra in an Inhomogeneous Magnetic Field," Journal of the American Chemical Society, vol. 109, pp. 7579-7581 (1987).

Hurlimann, M. & Griffin, D., "Spin Dynamics of Carr-Purcell-Meiboom-Gili-Like Sequences in Grossly Inhomogeneous B-O and B-1 Fields and Application to NMR Well Logging," Journal of Magnetic Resonance, vol. 143, pp. 1020-135 (2000).

International Search Report from International Application No. PCT/US97/05166, Published as WO 97/37239, Oct. 9, 1997.

Jershow, Alexej, "Multiple Echoes Initialed by a Single Radio Frequency Pulse in NMR," Chemical Physics Letters, vol. 296, pp. 466-470 (1998).

Kilenyi et al., "Two New Abnormal Pathways in the Para-Claisen Rearrangement of 2(Allyloxy)- and 2-(Crotyloxy)-3-hydroxybenzaldehyde," JOC, vol. 56, pp. 2591-2594 (1991).

Kleinberg, R.L. et al., "Novel NMR Apparatus for Investigating an External Sample," Journal of Magnetic Resonance, vol. 97, pp. 466-485 (1992).

Labouriau, Andrea, et al., "129-Xe NMR Spectroscopy of Metal Carbonyl Clusters and Metal Clusters in Zeolite NaY," J. Am. Chem. Soc., vol. 121, pp. 7674-7681 (1999).

Landon et al., "Magnetization transfer from laser-polarized xenon to protons located in the hydrophobic cavity of the wheat nonspecific lipid transfer protein," Protein Science, vol. 10, pp. 762-770 (2001).

Levitt, Malcolm H., "Composite Pulses," Historical Encyclopedia of NMR, Editors Grant & Harris, pp. 1396-1411 (1996). Abragam, A., "Thermal Relaxation in Liquids and Gases," Principles of Nuclear Magnetism, Oxford University Press, pp. 264-353 (1961).

Long, H.W. et al., "High-Field Cross Polarization NMR from Laser-Polarized Xenon to a Polymer Surface," Journal of the American Chemical Society, vol. 115, No. 18, pp. 8491-8492 (1993).

Luhmer et al., "Study of Xenon Binding in Cryptophane-A Using Laser-Induced NMR Polarization Enhancement," JACS, vol. 121, pp. 3502-3512 (1999).

Malmqvist, "Biospecific Interaction Analysis Using Biosensor Technology," Nature, vol. 361, pp. 185-187, Jan. 14, 1993.

Mansfield, P., "Multi-planar Image Formation Using NMR Spin Echoes," Journal of Physical Chemistry: Solid State Physics, vol. 10, pp. L55 thru L58 (1977).

McKim, Steven & Hinton, James F., "Evidence of Xenon Transport Through the Gramicidin Channel: A 120-Xe-NMR Study," Biochimica et Biophysica Acta, vol. 1193, pp. 186-198 (1994).

Middleton, Hunter, "MR Imaging with Hyperpolarized 3-He Gas," Magnetic Resonance in Medicine, vol. 33, pp. 271-275 (1995).

Miller, J.B. et al., "The NMR Chemical Shift of Xenon-129 Dissolved in Polymers," Macromolecules, vol. 26, No. 21, pp. 5602-5610 (1993).

Minagawa, Etsuo et al., "Isolation and Characterization of a *Thermostable Aminopepidase* (Aminopeptidase T) from Thermus aquaticus YT-1, an Extremely Thermophilic Bacterium," Agric. Biol. Chem., vol. 52, No. 7, pp. 1755-1763 (1988).

Miyawaki et al., "Fluorescent Indicators for Ca2+ Based on Green Fluorescent Proteins and Calmodulin" Nature, vol. 388, pp. 882-887, Aug. 28, 1997.

Mizusawa, Kiyoshi et al., "Production of Thermostable Alkaline Proteases by *Thermophilic streptomyces*," Applied Microbiology, vol. 17, No. 3, pp. 366-371, Mar. 1969.

Moschos, A. and Reisse, J., "Nuclear Magnetic Relaxation of Xenon-129 Dissolved in Organic Solvents," Journal of Magnetic Resonance, vol. 95, pp. 603-606,(1991).

Noggle, Joseph H. & Schirmer, Roger E., "The Nuclear Overhauser Effect," Chapter 1, pp. 4-43, Academic Press, (1971).

Overhauser, Albert W., "Polarization of Nuclei in Metals," Physical Review, Vol. 92, No. 2, pp. 411-415, Oct. 15, 1953.

Physical Review Letters, vol. 49, No. 1, pp. 25-28, Jul. 5, 1982.

Prange, Thierry et al., "Exploring Hydrophobic Sites in Proteins with Xenon or Krypton," Proteins: Structure, Function, and Genetics, vol. 30, pp. 61-73 (1998).

Quillin, Michael L. et al., "Size versus Polarizability in Protein-Ligand Interactions: Binding of Noble Gases Within Engineered Cavities in Phage T4 Lysozyme," J. Mol. Biol., vol. 302, pp. 955-977 (2000).

Raftery, D. et al., "Spin-Polarized 129 Xe NMR Study of a Polymer Surface," Journal of Physical Chemistry, vol. 97, No. 8, pp. 1649-1655 (1993).

Raftery, D., Long, M., Meersmann, T., Grandinetti, P. J., Reven, L., and Pines, A., "High-Field NMR of Absorbed Xenon Polarized by Laser Pumping," Physical Review Letters, vol. 66, No. 5, pp. 584-587, Feb. 4, 1991.

Ratcliffe, "Xenon NMR,"Annual Reports on NMR Spectroscopy, vol. 36, pp. 123-220 (1998).

Roncari, G. et al., "Thermophilic Aminopeptidases from *Bacillus stearothermophilus*," pp. 45-61, Jul. 15, 1968.

Rubin et al., "Detection of a Conformational Change in Maltose Binding Proteins by 129-Xenon NMR" Spectroscopy, J. Am. Chem. Soc. 2001, 123, 8616-17.

Rubin et al., "Evidence of Nonspecific Surface Interactions Between Laser-Polarized Xenon and Myoglobin in Solution," PNAS, vol. 97, No. 17, pp. 9472-9475, Aug. 15, 2000.

Sagane, Ryokichi et al., "The Dependence of the 33-Mev Pi+ Production Cross Section on Atomic Number," Physical Review, vol. 92, No. 2, pp. 212-213, October 15, 1953, Letters to the Editor.

Scharfenecker, Attila et al., "Diffusion Measurements with the Aid of Nutation Spin Echoes Appearing After Two Inhomogeneous Radiofrequency Pluses in Inhomogeneous Magnetic Fields," Journal of Magnetic Resonance, vol. 148, pp. 363-366 (2001).

Schoenborn, Benno P. et al., "Binding of Xenon to Sperm Whale Myoglobin," Nature, Vol. 4992, pp. 28.30, Jul. 3, 1965.

Schwartz, Maxime, in *Escherichia coli* and *Salmonella typhimurium*: Cellular and Molecular Biology; Neidhardt, F.C. et al. Eds.; American Society for Microbiology; Washington, D.C. vol. 2, pp. 1482-1502 (1987).

Sharff, Andrew J. et al., "Crystallographic Evidence of a Large Ligand-Induced Hinge-Twist Motion Between the Two Domains of the Maltodextrin Binding Protein Involved in Active Transport and Chemotaxis," Biochemistry, vol. 31, pp. 10657-10663 (1992).

Sharff, Andrew J. et al., "Refined 1.9A Structure Reveals the Mode of Binding of B-Cyclodextrin to the Maltodextrin Binding Protein," Biochemistry, vol. 52, No. 40, pp. 10553-10559 (1993).

Shilton, Brian H. et al., "Conformational Changes of Three Periplasmic Receptors for Bacterial Chemotaxis and Transport: The Maltose-, Glucose/Galactose- and Ribose-binding Proteins," J. Mol. Biol., vol. 264, pp. 350-363 (1996).

Shuker et al., "Discovering High-Affinity Ligands for Proteins: SAR by NMR," Science, vol. 274, pp. 1531-1534, Nov. 29, 1996.

Smith et al., "Intracellular Calcium Measurements by 19F NMR of Fluorine-Labeled Chelators," PNAS, vol. 80, pp. 7178-7182, Dec. 1983.

Soloman, I., "Relaxation Processes in a System of Two Spins," Physical Review, vol. 99, No. 2, pp. 559-565, Jul. 18, 1955.

Song, Y.-Q. et al., "Spin-Polarized 129-Xe Gas Imaging of Materials," Journal of Magnetic Resonance, vol. 115, pp. 127-130 (1995).

Stebbins, Jonathan & Farnan, Ian, "Nuclear Magnetic Resonance Spectroscopy in the Earth Sciences; Structure and Dynamics," Science, vol. 245, Issue 4915, pp. 257-263, Jul. 21, 1989.

Szmelcman, Sevec & Schwartz, Maxime, "Maltose Transport in *Escherichia coli* K12," European Journal of Biochemistry, vol. 65, pp. 13-19 (1976).

Tilton, Robert F. et al., "Cavities in Proteins: Structure of a Metmyoglobin-Xenon Complex Solved to 1.9A," Biochemistry, vol. 23, pp. 2849-2857 (1984).

Weitekamp, D. et al., "High-Resolution NMR Spectra in Inhomogeneous Magnetic Fields: Application of Total Spin Coherence Transfer Echoes," Journal of the American Chemical Society, vol. 103, pp. 3578-3579 (1981).

Wilson, Elizabeth K. "Hyperpolarized Gases Set NMR World Spinning," Chemical Engineering News, vol. 74, No. 52, pp. 21-23, Dec. 23, 1996.

Wolber, Jan et al., "Hyperpolarized 129-Xe NMR as a Probe for Blood Oxygenation," Magnetic Resonance in Medicine, vol. 43, pp. 491-496 (2000).

Chawla et al. (1998). In vivo magnetic resonance vascular imaging using laser-polarized $^3$He microbubbles. *Proc. Natl. Acad. Sci. USA*, 95:10832-10835.

Luhmer, et al. (1999). Study of xenon binding in Cryptophane-A using laser-induced NMR polarization enhancement, *J. Am. Chem. Soc.*, 121:3502-3512.

Miller, Keith W. et al., "Xenon NMR: Chemical Shifts of a General Anesthetic in Common Solvents, Proteins, and Membranes," Proc. Natl. Acad. Sci., vol. 78, No. 8, pp. 4946-4949, Aug. 1981.

Tilton, R.F., Jr. & Kuntz, I.D., Jr., "Nuclear Magnetic Resonance Studies of Xenon-129 with Myoglobin and Hemoglobin," Biochemistry, vol. 21, No. 26, pp. 6850-6857, 1982.

Bhaskar, N.D. and Happer, W., "Efficiency of Spin Exchange between Rubidium Spins and 129 Xe Nuclei in a Gas," Physical Review Letters, vol. 49, No. 1, pp. 25-28, Jul. 5, 1982.

Happer, W. et al., "Polarization of the Nuclear spins of Noble-Gas Atoms by Spin Exchange with Optically Pumped Alkali-Metal Atoms," Physical Review A, vol. 29, No. 6, pp. 3092-3110, Jun. 1984.

Moschos, A. and Reisse, J., "Nuclear Magnetic Relaxation of Xenon-129 Dissolved in Organic Solvents," Journal of Magnetic Resonance, vol. 95, pp. 603-606, (1991).

Raftery, D. et al., "NMR of Optically Pumped Xenon Thin Films," Chemical Physics Letters, vol. 191, No. 5, pp. 385-390, Apr. 10, 1992.

Raftery, D. et al., "Spin-Polarized 129 Xe NMR Study of a Polymer Surface," Journal of Physical Chemistry, vol. 97, No. 8, pp. 1649-1655, (1993).

Bowers, C.R. et al., "Cross Polarization from Laser-Polarized Solid Xenon to 13 CO2," Chemical Physics Letters, vol. 205, No. 2,3, pp. 168-170, Apr. 9, 1993.

Long, H.W. et al., "High-Field Cross Polarization NMR from Laser-Polarized Xenon to a Polymer Surface," Journal of the American Chemical Society, vol. 115, No. 18, pp. 8491-8492, (1993).

Miller, J.B. et al., "The NMR Chemical Shift of Xenon-129 Dissolved in Polymers," Macromolecules, vol. 26, No. 21, pp. 5602-5610, (1993).

Albert, M.S. et al., "Biological Magnetic Resonance Imaging Using Laser-Polarized 129-Xe," Letters to Nature, vol. 330, No. 21, pp. 199-201, (1994).

Song, Y.-Q. et al., "Spin-Polarized 129-Xe Gas Imaging of Materials," Journal of Magnetic Resonance, vol. 115, pp. 127-130, (1995).

Albert, Mitchell S. et al., "Measurement of 129-Xe T1 in Blood to Explore the Feasibility of Hyperpolarized 129-Xe MRI," Journal of Computer Asisted Tomography, vol. 19, No. 6, pp. 975-978, Nov./Dec. 1995.

Driehuys, B. et al., "Spin Transfer Between Laser-Polarized 129-Xe Nuclei and Surface Protons," Physics Letters A, vol. 184, No. 1, pp. 88-92, Dec. 27, 1993.

Driehuys, B. et al., "Surface Relaxation Mechanisms of Laser-Polarized 129-Xe," Physical Review Letters, vol. 74, No. 24, pp. 4943-4946, Jun. 12, 1995.
Service, Robert F., "(Amplifying) the Fine Details of Molecular Structure Is a Gas," Science, vol. 271, pp. 1810, Mar. 29, 1996.
Wilson, Elizabeth K., "Hyperpolarized Gases Set NMR World Spinning," Chemical Engineering News, vol. 74, No. 52, pp. 21-23, Dec. 23, 1996.
International Search Report from International Application No. PCT/US97/05166, Published as WO 97/37239, Oct. 9, 1997.
Middleton, Hunter, "MR Imaging with Hyperpolarized 3-He Gas," Magnetic Resonance in Medicine, vol. 33, pp. 271-275, (1995).
Meriles, Carlos A. et al., "Approach to High-Resolution Ex Situ NMR Spectroscopy," Science, vol. 293, pp. 82-85, Jul. 6, 2001.
Ackerman, Joseph H. et al., "Mapping of Metabolites in Whole Animals by 31-P NMR Using Surface Coils," Nature, vol. 283, pp. 167-170, Jan. 10, 1980.
Stebbins, Jonathan & Farnan, Ian, "Nuclear Magnetic Resonance Spectroscopy in the Earth Sciences: Structure and Dynamics," Science, vol. 245, Issue 4915, pp. 257-263, Jul. 21, 1989.
Frank, S. & Lauterbur, P., "Voltage-Sensitive Magnetic Gels as Magnetic Resonance Monitoring Agents," Nature, vol. 363, pp. 334-336, May 27, 1993.
Hurlimann, M. & Griffin, D., "Spin Dynamics of Carr-Purcell-Meiboom-Gill-Like Sequences in Grossly Inhomogeneous B-0 and B-1 Fields and Application to NMR Well Logging," Journal of Magnetic Resonance, vol. 143, pp. 120-135, (2000).
Blumich, B. et al., "The NMR-Mouse: Construction, Excitation, and Applications," Magnetic Resonance Imaging, vol. 16, No. 5/6, pp. 479-484, (1998).
Weitekamp, D. et al., "High-Resolution NMR Spectra in Inhomogeneous Magnetic Fields: Application of Total Spin Coherence Transfer Echoes," Journal of the American Chemical Society, vol. 103, pp. 3578-3579, (1981).
Balbach, John et al., "High-Resolution NMR in Inhomogeneous Fields," Chemical Physics Letters, vol. 277, pp. 367-374, (1997).
Hall, Laurance D. et al., "Measurements of High-Resolution NMR Spectra in an Inhomogeneous Magnetic Field," Journal of the American Chemical Society, vol. 109, pp. 7579-7581, (1987).
Richter, Wolfgang et al., "Imaging with Intermolecular Multiple-Quantum Coherences in Solution Nuclear Magnetic Resonance," Science, vol. 267, Issue 5198, pp. 654-657, Feb. 3, 1995.
Jerschow, Alexej, "Multiple Echoes Initiated by a Single Radio Frequency Pulse in NMR," Chemical Physics Letters, vol. 296, pp. 466-470, (1998).
Scharfenecker, Attila et al., "Diffusion Measurements with the Aid of Nutation Spin Echoes Appearing After Two Inhomogeneous Radiofrequency Pulses in Inhomogeneous Magnetic Fields," Journal of Magnetic Resonance, vol. 148, pp. 363-366, (2001).
Ardelean, Ioan et al., "The Nutation Spin Echo and Its Use for Locatlized NMR," Journal of Magnetic Resonance, vol. 146, pp. 43-48, (2000).
Levitt, Malcolm H., "Composite Pulses," Historical Encyclopedia of NMR, Editors Grant & Harris, pp. 1396-1411, (1996).
Abragam, A., "Thermal Relaxation in Liquids and Gases," Principles of Nuclear Magnetism, Oxford University Press, pp. 264-353, (1961).
Kleinberg, R.L. et al., "Novel NMR Apparatus for Investigating an External Sample," Journal of Magnetic Resonance, vol. 97, pp. 466-485, (1992).
Andrew, E.R. et al., "Nuclear Magnetic Resonance Spectra from a Crystal Rotated at High Speed," Nature-Letters to the Editor, pp. 1659, Dec. 13, 1958.
de Swiet, Thomas M. et al., "In Situ Analysis of Fluids Contained in Sedimentary Rock," Journal of Magnetic Resonance, vol. 133, pp. 385-387, (1998).
Chmelka, B.F. & Pines, A., "Some Developments in Nuclear Magnetic Resonance of Solids," Science, vol. 246, Issue 4926, pp. 71-77, Oct. 6, 1989.
Rubin et al., "Evidence of nonspecifice Surface Interactions Between Laser-Polarized Xenon and Myoglobin in Solution," PNAS, vol. 97, No. 17, pp. 9472-9475, Aug. 15, 2000.
Canceill et al., "Synthesis and Excition Optical Activity of D3-Cryptophanes," JACS, vol. 109, pp. 6454-6464, (1987).
Collet, "Cyclotriveratrylenes and Cryptophanes," in Tetrahedron Report No. 226, Tetredron, vol. 43, No. 24, pp. 5725-5759.
Kilenyi et al., "Two New Abnormal Pathways in the Para-Claisen Rearrangement of 2(Allyloxy)- and 2-(Crotyloxy)-3-hydroxybenzaldehyde," JOC, vol. 56, pp. 2591-2594, (1991).
Wilchek et al., "Applications of Aviden-Biotim Technology: Literature Survey," Methods in Enzymology, vol. 184, pp. 14-45.
Landon et al., "Magnetization transfer from laser-polarized xenon to protons located in the hydrophobic cavity of the wheat nonspecific lipid transfer protein," Protein Science, vol. 10, pp. 763-770, (2001).
Weber et al., "Structural Origins of High-Affinity Biotin Binding to Streptavidin," Science, vol. 243, pp. 85-88, Jan. 6, 1989.
Brotin et al., "129-Xenon NMR Spectroscopy of Deuterium-Labeled Cryptophane-A Xenon Complexes," JACS, vol. 122, pp. 1171-1174, (2000).
Navon et al., "Enhancement of Solution NMR and MRI with Laser-Polarized Xenon," Science, vol. 271, pp. 1848-1851, Mar. 29, 1996.
Tilton et al., "NMR Studies of Xenon-129 with Myoglobin and Hemoglobin," Biochemistry, vol. 21, pp. 6850-6857, (1982).
Luhmer et al., "Study of Xenon Binding in Cryptophane-A Using Laser-Induced NMR Polarization Enhancement," JACS, vol. 121, pp. 3502-3512, (1999).
Ginsburg et al., "Temperature-Dependent Molecular Motions of Cholesterol Esters: A Carbon 13 NMR Study," Biochemistry, vol. 21, pp. 6857-6867, (1982).
Bowers et al., "Exploring Surfaces and Cavitities in Lipoxygenase and Other Proteins by Hyperpolarized Xenon-129 NMR," JACS, vol. 121, pp. 9370-9377, (1999).
Wolber et al., "Hyperpolarized 120-Xenon NMR as a Probe for Blood Oxygenation," Magnetic Resonance in Medicine, vol. 43, pp. 491-496, (2000).
Albert et al., "Biological Magnetic Resonance Imaging Using Laser Polarized 129-Xenon," Nature, vol. 370, pp. 200-201, Jul. 21, 1994.
Song, "NMR and MRI Using Laser-Polarized Xenon," Spectroscopy, vol. 14, pp. 726-733, Jul. 1999.
Ratcliffe, "Xenon NMR," Annual Reports on NMR Spectroscopy, vol. 36, pp. 123-220, (1998).
Walker et al., "Spin-Exchange Optical Pumping of Noble-Gas Nuclei," Reviews of Modern Physics, vol. 69, No. 2, pp. 629-642, Apr. 1997.
Louie et al., "In Vivo Visualization of Gene Expression Using MRI," Nature Biotechnology, vol. 18, pp. 321-325, Mar. 18, 2000.
Shuker et al., "Discovering High-Affinity Ligands for Proteins: SAR by NMR," Science, vol. 274, pp. 1531-1533, Nov. 29, 1996.
Miyawaki et al., "Fluorescent Indicators for Ca2+ Based on Green Fluorescent Proteins and Calmodulin,j" Nature, vol. 388, pp. 882-887, Aug. 28, 1997.
Checovich et l., Fluorescence Polarization-A New Tool for Cell Molecular Biology," Nature, vol. 375, pp. 254-256, May 18, 1995.
Malmqvist, "Biospecific Interaction Analysis Using Biosensor Technology," Nature, vol. 361, pp. 185-187, Jan. 14, 1993.
Smith et al., "Intracellular Calcium Measurements by 19F NMR of Fluorine-Labeled Chelators," PNAS, vol. 80, pp. 7178-7189, Dec. 1989.
Bifone, A. et al., "NMR of Laser-Polarized Xenon in Human Blood," Proc. Natl. Acad. Sci., vol. 93, pp. 12932-12936, Nov. 1996.
Song, Yi-Qiao et al., "Selective Enhancement of NMR Signals for x-Cyclodextrin with Laser-Polarized Xenon," Angw. Chem. Int. Ed. Engl., vol. 36, No. 21, pp. 2368-2370, Nov. 14, 1997.
Augustine, Matthew P. et al., "Low Field Magnetic Resonance Images of Polarized Noble Gases Obtained with a dc Superconducting Quantum Interference Device," Applied Physics Letters, vol. 72, No. 15, pp. 1908-1910, Apr. 13, 1998.
Schoenborn, Benno P. et al., "Binding of Xenon to Sperm Whale Myoglobin," Nature, vol. 4992, pp. 28-30, Jul. 3, 1965.
Tilton, Robert F. et al., "Cavities in Proteins: Structure of a Metmyoglobin-Xenon Complex Solved to 1.9A," Biochemistry, vol. 23, pp. 2849-2857, (1984).

Prange, Thierry et al., "Exploring Hydrophobic Sites in Proteins with Xenon or Krypton," Proteins: Structure, Function, and Genetics, vol. 30, pp. 61-73, (1998).

Quillin, Michael L. et al., "Size versus Polarizability in Protein-Ligand Interactions: Binding of Noble Gases Within Engineered Cavities in Phage T4 Lysozyme," J. Mol. Biol., vol. 302, pp. 955-977, (2000).

Walker, Thad G., "Spin-Exchange Optical Pumping of Noble-Gas Nuclei," Reviews of Modern Physics, vol. 69, No. 2, pp. 629-642, Apr. 1997.

Shilton, Brian H. et al., "Conformational Changes of Three Periplasmic Receptors for Bacterial Chemotaxis and Transport: The Maltose-, Glucose/Galactose- and Ribose-binding Proteins," J. Mol. Biol., vol. 264, pp. 350-363, (1996).

Labouriau, Andrea, et al., "129-Xe NMR Spectroscopy of Metal Carbonyl Clusters and Metal Clusters in Zeolite NaY," J. Am. Chem. Soc., vol. 121, pp. 7674-7681, (1999).

Spurlino, John C., et al., "The 2.3 A Resolution Structure of the Maltose- or Maltodextrin- binding Protein, A Primary Receptor of Bacterial Active Transport and Chemotaxis," The Journal of Biological Chemistry, vol. 266, No. 8, pp. 5202-5219, Mar. 15, 1991.

Wolber, Jan et al., "Spin-Lattice Relaxation of Laser-Polarized Xenon in Human Blood," Proc. Natl. Acad. Sci., vol. 96, pp. 3664-3669, Mar. 1999.

Sharff, Andrew J. et al., "Refined 1.9A Structure Reveals the Mode of Binding of B-Cyclodextrin to the Maltodextrin Binding Protein," Biochemistry, vol. 52, No. 40, pp. 10553-10559, (1993).

Brotin, Thierry et al., "129-Xe NMR Spectroscopy of Deuterium Labeled Cryptophane-A Xenon Complexes: Investigation of Host-Guest Complexation Dynamics," J. Am. Chem. Soc., vol. 122, pp. 1171-1174, (2000).

Rubin, Seth M. et al., "Evidence of Nonspecific Surface Interactions Between Laser-Polarized Xenon and Myoglobin in Solution," PNAS, vol. 97, No. 17, pp. 9472-0475, Aug. 15, 2000.

Hall, Jason A. et al., "The Modes of Ligand Binding in Maltose-Binding Protein of *Escherichia coli*," Journal of Biological Chemistry, vol. 272, No. 28, pp. 17605-17609, Jul. 1997.

Wolber, Jan et al., "Hyperpolarized 129-Xe NMR as a Probe for Blood Oxygenation," Magnetic Resonance in Medicine, vol. 43, pp. 491-496, (2000).

McKim, Steven & Hinton, James F., "Evidence of Xenon Transport Through the Gramicidin Channel: A 120-Xe-NMR Study," Biochimica et Biophysica Acta, vol. 1193, pp. 186-198, (1994).

Bowers, C.R. et al.,"Exploring Surfaces and Cavities in Lipoxygenase and Other Proteins by Hyperpolarized Xenon-129 NMR," J. Am. Chem. Soc., vol. 121, No. 40, pp. 9370-9378, (1999).

Diehl, P. and Jokisaari, J., "Nuclear Magnetic Relaxation of the 129-Xe and 131-Xe Isotopes of Xenon Gas Dissolved in Isotropic and Anisotropic Liquids," Journal of Magnetic Resonance, vol. 88, pp. 660-665, (1990).

Solomon, I., "Relaxation Processes in a System of Two Spins," Physical Review, vol. 99, No. 2, pp. 559-565, Jul. 15, 1955.

Mansfield, P., "Multi-Planar Image Formation Using NMR Spin Echoes," Journal of Physical Chemistry: Solid State Physics, vol. 10, pp. L55 thru L58, (1977).

Haase, A., Frahm, J., Matthael, D., Hanicke, W., and Merboldt, K.D., "Flash Imaging. Rapid NMR Imaging Using Low Flip-Angle Pulses," Journal of Magnetic Resonance, vol. 67, pp. 258-266, (1986).

Raftery, D., Long, H., Meersmann, T., Grandinetti, P.J., Reven, L., and Pines, A., "High-Field NMR of Absorbed Xenon Polarized by Laser Pumping," Physical REview Letters, vol. 66, No. 5, pp. 584-587, Feb. 4, 1991.

Long, H.W., Gaede, H.C., Shore, J., Reven, L., Bowers, C.R., Kritzenberge, J., Pietrass, T., and Pines, A., "High-Field Cross Polarization NMR From Laser-Polarized Xenon to a Polymer Surface," Journal of the American Chemical Society, vol. 115, No. 18, pp. 8491-8492, Nov. 18, 1993.

Hall, Jason A. et al.; "Two Modes of Ligand Binding in Maltose-Binding Protein of *Escherichia coli*," Journal of Biological Chemistry, vol. 272, No. 28, pp. 17605-17609, Jul. 11, 1997.

Faruqi, Tatjana R. et al.; "Structure-Function Analysis of Protease-Activated Receptor 4 Tethered Ligand Peptides," Journal of Biological Chemistry, vol. 275, No. 26, pp. 19728-19734, Jun. 30, 2000.

Bartik, Kristin et al.; "129 Xenon and 1H NMR Study of the Reversible Trapping of Xenon by Cryptophane-A in Organic Solution," Journal of American Chemical Society, vol. 120, pp. 784-791, (1998).

* cited by examiner

Odd number of Xe/H pulse pairs

APPARATUS FOR PREPARING A SOLUTION OF A HYPERPOLARIZED NOBLE GAS FOR NMR AND MRI ANALYSIS

CROSS-REFERENCE TO RELATED APPLICATIONS

This application is a divisional of U.S. application Ser. No. 10/164,324 filed on Jun. 5, 2002, now U.S. Pat. No. 6,818,202, which is a divisional of U.S. application Ser. No. 08/825,475 filed on Mar. 28, 1997, now U.S. Pat. No. 6,426,058, which claims priority from U.S. provisional application Ser. No. 60/014,321 filed on Mar. 29, 1996.

STATEMENT REGARDING FEDERALLY SPONSORED RESEARCH OR DEVELOPMENT

This invention was made with Government support under Contract No. DE-AC03-765F00098, awarded by the Department of Energy. The Government has certain rights in this invention.

REFERENCE TO A COMPUTER PROGRAM APPENDIX

Not Applicable

FIELD OF THE INVENTION

The present invention relates generally to nuclear magnetic resonance (NMR) techniques for both spectroscopy and imaging. More particularly, the present invention relates to the use of hyperpolarized noble gases (e.g., Xe and He) to enhance and improve NMR and MRI.

BACKGROUND OF THE INVENTION

Nuclear magnetic resonance (NMR) is an established technique for both spectroscopy and imaging. NMR spectroscopy is one of the most powerful methods available for determining primary structure, conformation and local dynamic properties of molecules in liquid, solid and even gas phases. As a whole-body imaging technique, Magnetic Resonance Imaging (MRI) affords images possessing such superb soft tissue resolution that MRI is the modality of choice in many clinical settings. MRI can produce images which allow the clinician to distinguish between a pathological condition and healthy tissue. For example, MR images clearly differentiate tumors from the surrounding tissue. Further, using MRI it is possible to image specific regions within the organism and to obtain anatomical (morphology and pathology) and/or functional information about various processes including blood flow and tissue perfusion. Functional imaging of the brain is now also well documented.

The structural and functional information available through MRI is complemented by whole-body NMR spectroscopy. NMR spectroscopic studies on organisms provides a means to probe the chemical processes occurring in the tissue under study. For example, the location and quantity of intrinsic NMR spectroscopic markers such as lactate and citrate can be studied to gain insight into the chemical processes underlying a disease state (Kurhanewicz, J., et al., *Urology* 45: 459-466 (1995)). NMR spectroscopy can also be used to observe the effects of administered drugs on the biochemistry of the organism or the changes in the drug which occur following its administration (Maxwell, R. J., *Cancer Surv.* 17: 415-423 (1993)). Efforts to improve the information yield from MRI and NMR spectroscopy through increased sensitivity or the use of appropriately designed extrinsic probes have been ongoing since the inception of these techniques.

Sensitivity poses a persistent challenge to the use of NMR, both in imaging and spectroscopy. In proton MRI, contrast is primarily governed by the quantity of protons in a tissue and the intrinsic relaxation times of those protons (i.e., $T_1$ and $T_2$). Adjacent tissues which are histologically distinct yet magnetically similar appear isointense on an MR image. As the proton content of a tissue is not a readily manipulable parameter, the approach taken to provide distinction between magnetically similar tissues is the introduction into the biological system of a paramagnetic pharmaceutical (i.e, contrast enhancing agent) such as Gd(DTPA) (Niendorf, H. P., et al., *Eur. J. Radiol.*, 13: 15 (1991)). Interaction between the proton nuclei and the unpaired spins on the $Gd^{+3}$ ion dramatically decrease the proton relaxation times causing an increase in tissue intensity at the site of interaction. Gd(DTPA) and analogous agents are small molecular agents which remain largely confined to the extracellular compartment and do not readily cross the intact blood-brain barrier. Thus, these agents are of little use in functional brain imaging.

Similar to MRI, NMR spectroscopic studies generally rely on detecting NMR active nuclei which are present in their natural abundance (e.g., $^1H$, $^{31}P$, $^{13}C$) (Sapega, A. A., et al., *Med. Sci. Sports Exerc.*, 25: 656-666 (1993)). Additionally, the chemical species under observation must be spectroscopically distinguishable from the other compounds within the window of observation. Thus, sensitivity in NMR spectroscopy is a function of both the abundance and the spectral characteristics of the molecule(s) desired to be studied. The range of NMR spectroscopic studies has been somewhat expanded by the application of exogenous probes which contain NMR active nuclei, for example $^{19}F$ (Aiken, N. R., et al., *Biochim. Biophys. Acta*, 1270: 52-57 (1995)).

Noble gases are of interest as tracers and probes for MRI and NMR spectroscopy (Middleton, H., et al., *Magn. Res. Med.* 33: 271 (1995)), however, the sensitivity of MRI and NMR spectroscopy for these molecules is relatively low. A factor which contributes to the lack of sensitivity of these techniques for the noble gases is that the spin polarization, or net magnetic moment, of the noble gas sample is low. For example, a typical molecule at thermal equilibrium at room tem has an excess of spins in one direction along an imposed magnetic field relative to those in the opposite direction of generally less than 1 in $10^5$. Lower temperatures and higher fields, to the extent that these can be imposed, provide only limited benefit. Alternative approaches rely on disrupting the equilibrium magnetization by forcing molecules in the sample into a polarized state. Two methods known in the art for enhancing the spin polarization of a population of nuclei are dynamic nuclear polarization and optical pumping.

Dynamic nuclear polarization, originally applied to metals, arises from the cross relaxation between coupled spins. The phenomenon is known as the Overhauser Effect with early disclosures by Overhauser and others (Ovehauser, A. W., "Polarization of nuclei in metals," *Phys. Rev.* 92(2): 411-415 (1953), Solomon, I., "Relaxation processes in a system of two Spins," *Phys. Rev.* 99(2): 559-565 (1955), and Carver, T. R., et al., "Experimental verification of the Overhauser nuclear polarization effect," *Phys. Rev.* 102(4): 975-980 (1956)). The Nuclear Overhauser Effect between nuclear spins is widely used to determine interatomic distances in NMR studies of molecules in solution.

Optical pumping is a method for enhancing the spin polarization of gases which consists of irradiating an alkali metal, in the presence of a noble gas, with circularly polarized light. The hyperpolarized gases that result have been used for NMR studies of surfaces and imaging void spaces and surfaces. Examples are the enhanced surface NMR of hyperpolarized $^{129}$Xe, as described by Raftery, D., et al., *Phys. Rev. Lett.* 66: 584 (1991); signal enhancement of proton and $^{13}$C NMR by thermal mixing from hyperpolarized $^{129}$Xe, as described by Driehuys, B., et al., *Phys. Lett.* A184: 88-92 (1993), and Bowers, C. R., et al., *Chem. Phys. Lett.* 205: 168 (1993), and by Hartmann-Hahn cross-polarization, as described by Long, H. W., et al., *J. Am. Chem. Soc.* 115: 8491 (1993); and enhanced MRI of void spaces in organisms (such as the lung) and other materials, as described by Albert, M. S., et al., *Nature* 370: 199-201 (1994), and Song, Y.-Q., et al., *J. Magn. Reson.* A115: 127-130 (1995).

Although hyperpolarize noble gases have proven useful as probes in the study of the air spaces in lungs, the effectiveness or sensitivity of these methods is somewhat compromised for biological materials and organs, such as blood and the parts of the body that are accessible only through the blood. During its residence time in the blood, the hyperpolarized gas is diluted considerably and the delay in transferring the gas from the lung space to the blood consumes much of the time (e.g., $T_1$) required for the polarized gas to return to its non-hyperpolarized state. Further complicating the situation, the penetration of the hyperpolarized gas into the interior of red blood cells dramatically reduces the $T_1$ of the hyperpolarized gas and thus, sorely attenuates the temporal range over which the gas can serve as an effective probe.

A considerable advance in both MRI and NMR spectroscopy could be achieved by the introduction of a versatile hyperpolarized noble gas-based NMR active tracer which could also function as a contrast enhancing agent or otherwise affect, in a spectroscopically discernable manner, sample molecules to which the probe is proximate. Among other applications, such an agent would be useful in conjunction with functional imaging of the brain and also to probe the dynamics of exchange between the intracellular and extracellular compartments of various tissues. Of even more profound significance would be a means of delivering the tracer, either through the blood or via direct injection into the tissue of interest, which maintains the hyperpolarization of the gas during the delivery process and through the imaging or spectroscopic experiment. Quite surprisingly, the instant invention provides both such a tracer and delivery method.

SUMMARY OF THE INVENTION

The present invention provides methods for using hyperpolarized noble gases in conjunction with NMR spectroscopy and MRI. The noble gases are useful both as tracers, which are themselves detected, and also as agents which affect the magnetic properties of other nuclei present in a sample.

Thus, in a first aspect, the present invention provides a method for analyzing a sample containing an NMR active nucleus, the method comprising:
(a) contacting the sample with a hyperpolarized noble gas;
(b) scanning the sample by nuclear magnetic resonance spectroscopy, magnetic resonance imaging, or both nuclear magnetic resonance spectroscopy and magnetic resonance imaging;
(c) detecting the NMR active nucleus, wherein the NMR active nucleus is a nucleus other than a noble gas.

In another aspect, the present invention provides a method for analyzing a sample which comprises: (a) combining a hyperpolarized noble gas with a fluid to form a mixture; (b) contacting the sample with the mixture; and (c) scanning the sample, the noble gas or both the sample and the noble gas by nuclear magnetic resonance spectroscopy, magnetic resonance imaging, or both nuclear magnetic resonance spectroscopy and magnetic resonance imaging.

In a further aspect, the invention provides a pharmaceutical composition which comprises a hyperpolarized noble gas dissolved in a physiologically compatible liquid carrier.

In yet another aspect, the present invention provides a method for studying a property of a noble gas in a tissue. This method of the invention comprises: (a) hyperpolarizing a noble gas; (b) dissolving the hyperpolarized noble gas in a physiologically compatible liquid carrier to form a mixture; (c) contacting the tissue with the mixture from (b); and (d) scanning the tissue by nuclear magnetic resonance, magnetic resonance imaging, or both, whereby the property of the noble gas in the tissue is studied.

In a further aspect, the invention provides a method for enhancing the relaxation time of a hyperpolarized noble gas in contact with a physiological fluid. This method comprises: (a) forming a hyperpolarized noble gas intermediate solution by dissolving the hyperpolarized noble gas in a fluid in which the relaxation time of the noble gas is longer than the relaxation time of the noble gas in the physiological fluid; and (b) contacting the physiological fluid with the intermediate solution.

In yet a further aspect, the present invention provides a method for measuring a signal transferred from at least one hyperpolarized noble gas atom to at least one non-noble gas NMR active nucleus, comprising: (a) contacting a non-noble gas NMR active nucleus with a hyperpolarized noble gas atom; (b) applying radiofrequency energy to the non-noble gas NMR active nucleus in a magnetic field; and (c) measuring the signal transferred from the hyperpolarized noble gas atom to the non-noble gas NMR active nucleus using nuclear magnetic resonance spectroscopy, magnetic resonance imaging, or both.

In a still further aspect, the invention provides a pulse sequence for heteronuclear difference spin polarization induced nuclear Overhauser effect (SPINOE) NMR of a system comprising at least one hyperpolarized noble gas atom and at least one non-noble gas NMR active nucleus, comprising: (a) at least one non-noble gas NMR active nucleus π/2 pulse; (b) a non-noble gas NMR active nucleus π pulse applied simultaneously with application of a noble gas π pulse; and (c) a non-noble gas NMR active nucleus π/2 pulse.

In an additional aspect, the invention provides an apparatus for preparing a solution of a hyperpolarized noble gas in a fluid, the apparatus comprising:
a vessel for receiving the fluid;
a reservoir for receiving the hyperpolarized noble gas, the reservoir communicating through a first shutoff valve with the vessel, the reservoir being shaped to allow the reservoir to be cooled independently of the vessel;
a gas inlet port communicating through a second shutoff valve with the reservoir; and
a means for withdrawing the fluid from the vessel independently of the first and second shutoff valve.

Other features, objects and advantages of the invention and its preferred embodiments will become apparent from the detailed description which follows.

BRIEF DESCRIPTION OF THE DRAWINGS

FIG. 5A shows the initial equilibrium spectrum and the time dependent spectra following the selective inversion. FIG. 5B shows the time dependence of the signal intensities.

$$I(t)=a+b(e^{-t/t1}-e^{-t/t2}) \qquad (1)$$

yielding time constants of 120 s and 1050 s (●), and 140 s and 1020 s (♦). $^1$H NMR was performed at 185 MHz using a home-built probe and a tipping angle of 3°.

Figure 10:
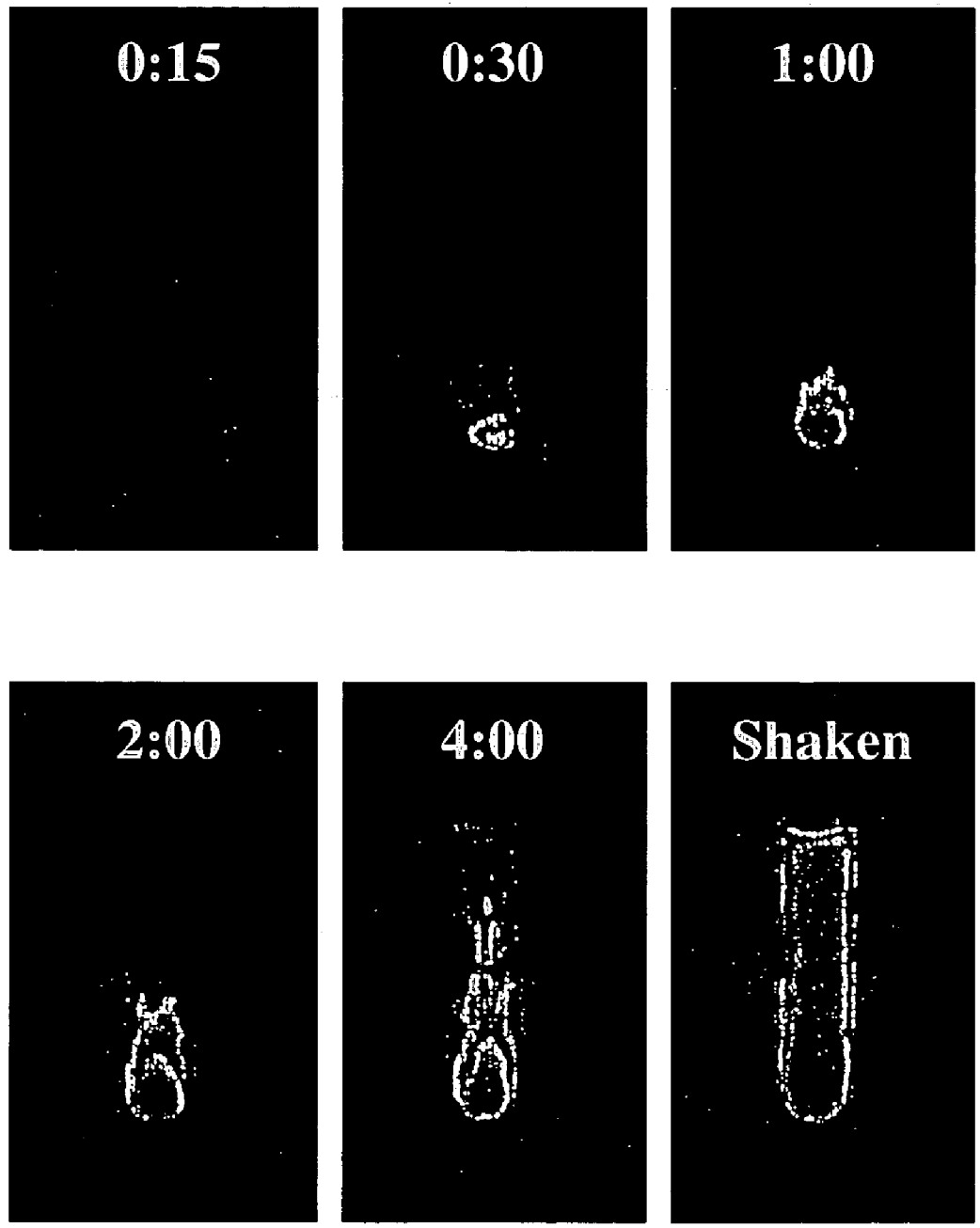

FIG. 10. Time-resolved, two-dimensional magnetic resonance images of $^{129}$Xe dissolved in benzene, taken after the exposure of the benzene to hyperpolarized $^{129}$Xe. A Xe concentration gradient exists immediately after the Xe is admitted, evolving with time to a more uniform solution. The 64 pixel by 128 pixel images were taken by the fast low-angle shot (FLASH) imaging method on a Quest 4300 spectrometer, with a tipping angle of 3° for each of the 64 signal acquisitions. The frequency-encoding gradient was 3.5 G/mm. The step size of the phase-encoding gradient pulses, which were 500 μs long, was 0.063 G/mm. The diameter of the sample tube is 7 mm, and the solution occupies a region of length 15 mm.

Figure 11:
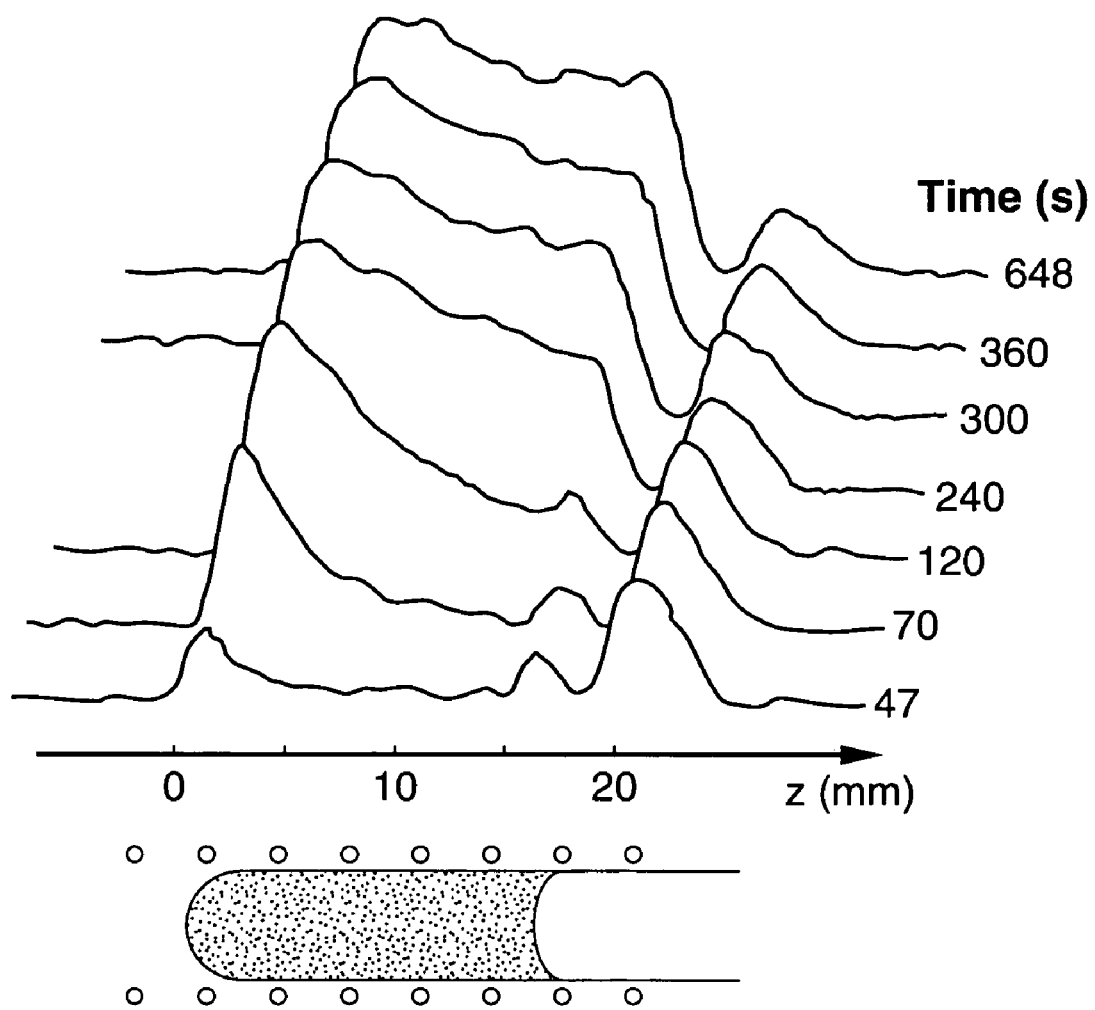

FIG. 11. Time-resolved distribution of $^{129}$Xe magnetization in partially deuterated benzene from MRI projection along the tube axis (z). The sample was not shaken after xenon was admitted to the benzene in order to prevent a uniform initial concentration. In the first image taken 47 s after the admission of the xenon gas to the solution three regions may be distinguished. The intensity above the solution level (above 18 mm) arises from $^{129}$Xe in the gas phase which is displaced from the dissolved $^{129}$Xe signal due to its different chemical shift. The decrease of the gas signal above 21 mm along the z axis is due to the declining NMR sensitivity beyond the radiofrequency coil, represented by circles in the schematic. The signal maximum at a position of 15.2 mm corresponds to the top of the solution, arising from xenon diffusing into the solution from the gas phase. The signal maximum at about 1.3 mm corresponds to the lower end of the tube. Thus, xenon accumulates at the bottom of the sample tube first and a discernible xenon concentration gradient persists for up to 5 minutes. The concentration gradient results from natural convection due to density differences between the xenon solution and that of pure benzene, progressing ultimately to a uniform saturated xenon solution. The imaging field gradient was 2.6 G/mm.

Figure 12:
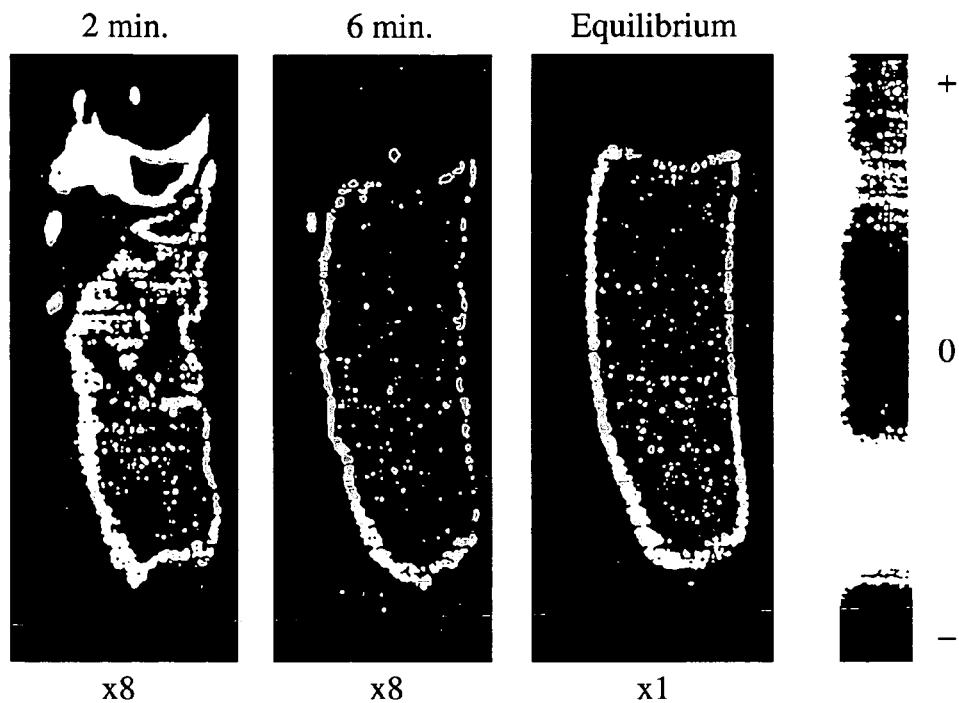

FIG. 12. Two-dimensional magnetic resonance images of the NOE enhanced $^1$H signals at 2 and 6 minutes after hyperpolarized xenon was admitted to the sample tube containing normal benzene. The enhancement images were obtained by subtracting the equilibrium image shown, which is the average of four images taken after 25 minutes. The intensity scale in the difference images has been magnified 8-fold for clarity. The maximum NOE enhancement in the 2 minute image is 0.05; that in the 6 minute image is 0.12. A perceptible gradient of the enhanced $^1$H signal is observed in the 2 minute image, corresponding to the observed gradient in the xenon concentration and the enhancement is found to be uniform in the 6 minute image when the xenon concentration gradient is diminished. The negative region in the 2 minute image could be caused by expansion of the liquid phase as xenon dissolves. The images were taken by the Echo Planar Imaging method (Mansfield, P., *J. Phys. C* 10, L55 (1977)) in 24 ms. The frequency-encoding gradient was 3.15 G/mm; the phase-encoding gradient pulses were 0.14 G/mm and 50 µs long. The image dimension was 128×32, and the image was zero-filled to 256×256 in data processing. The skew of the image is due to the inhomogeneity of the static magnetic field.

Figure 13:
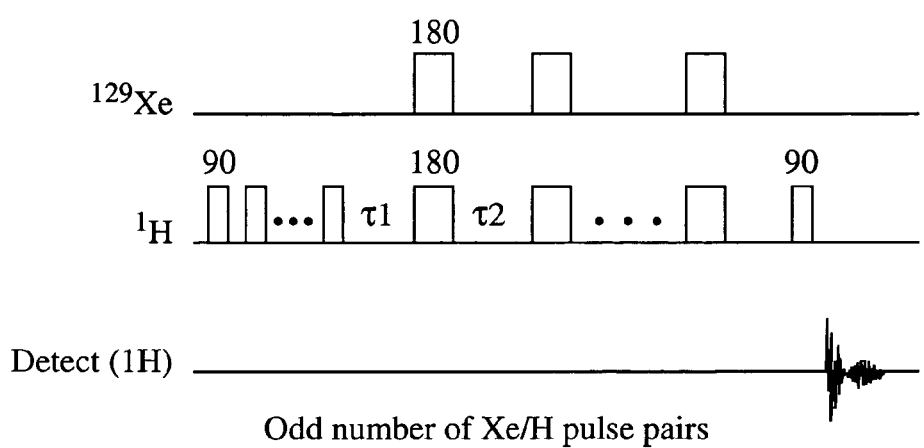

FIG. 13. Schematic diagram of the pulse sequence used to obtain heteronuclear difference SPINOE spectra. The proton magnetization is saturated first by a series of $\pi/2$ pulses and a z-axis magnetic field gradient is applied in between the pulses to dephase the transverse components of the magnetization for optimal saturation. The $\pi$ pulses helps to reduce the growth of proton signal due to spin-lattice relaxations. A $\pi$ pulse is also applied to the $^{129}$Xe resonance at the same time of the proton $\pi$ pulses so that the $^{129}$Xe magnetization is inverted in synchronization with the proton magnetization. This synchronization ensures that the SPINOE signals will be accumulated during the entire mixing time. Both proton and xenon $\pi$ pulses are adiabatic pulses BIR4 of 1 ms in duration.

Figure 14:
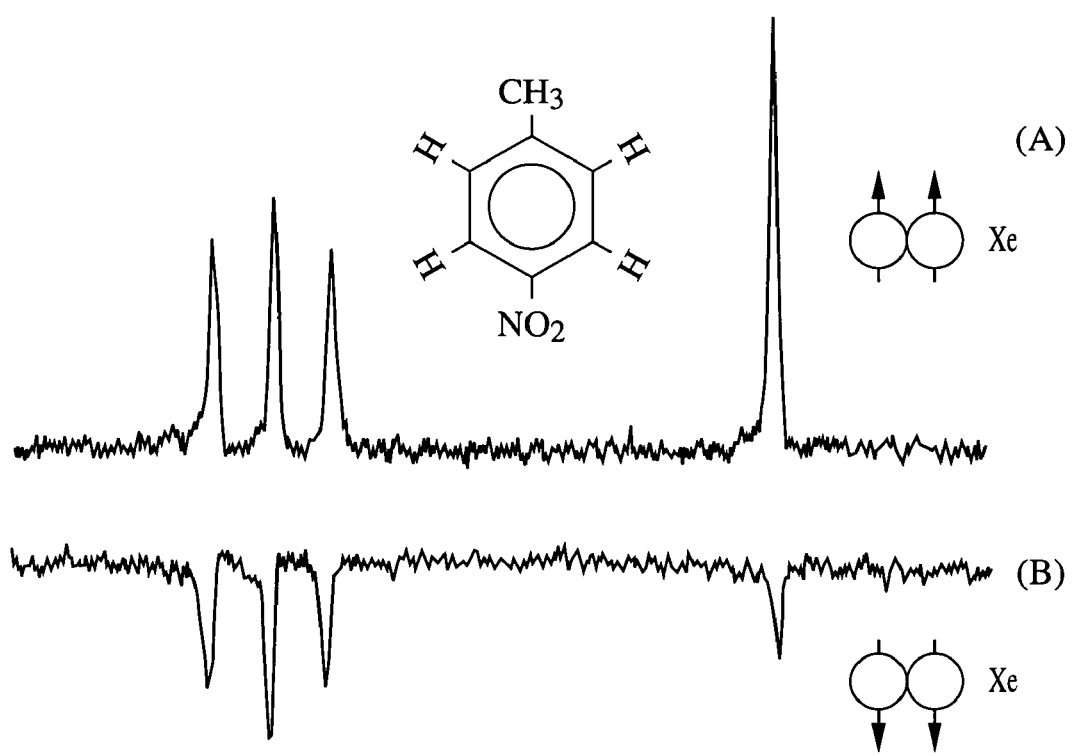

FIGS. 14A and 14B. (A) Proton spectra of 0.1 M p-nitrotoluene solution in perdeuterated benzene at thermal equilibrium; (B) SPINOE proton spectra of 0.1 M p-nitrotoluene solution in perdeuterated benzene with positive and negative $^{129}$Xe spin polarization. The total mixing time is 2.1 s.

Figure 15:
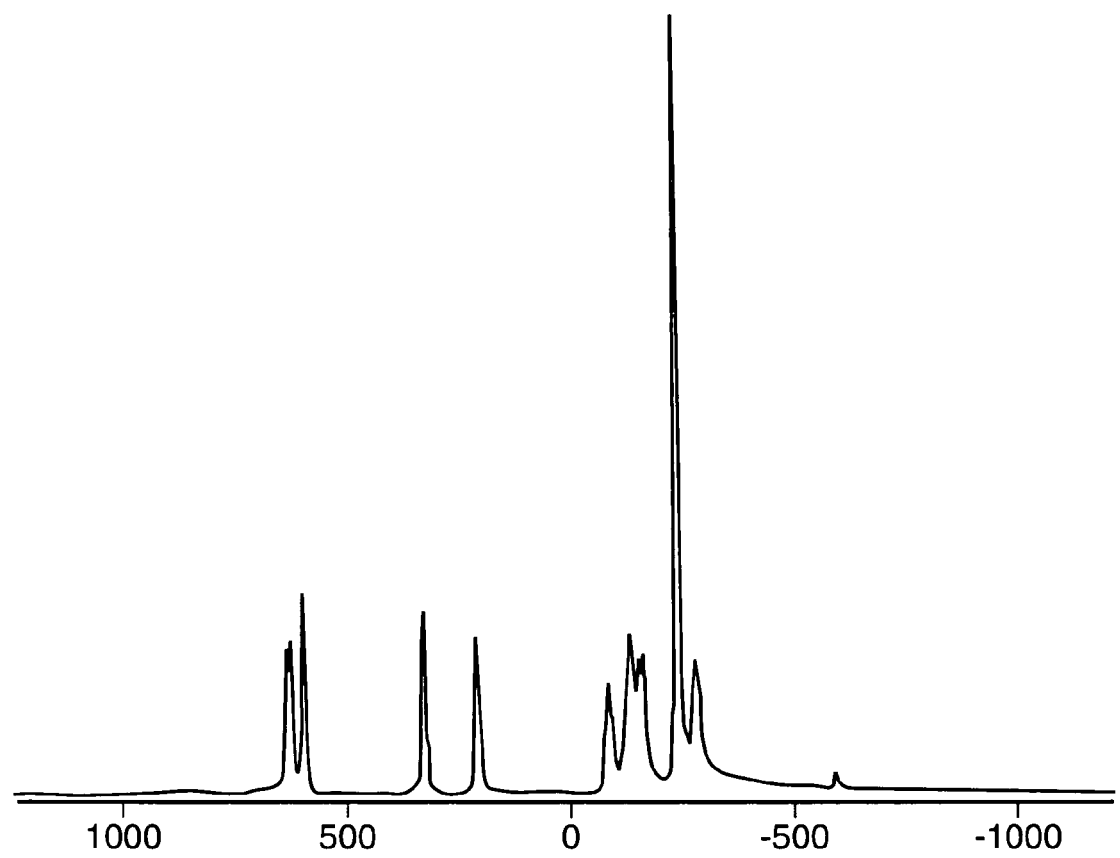
Figure 16:
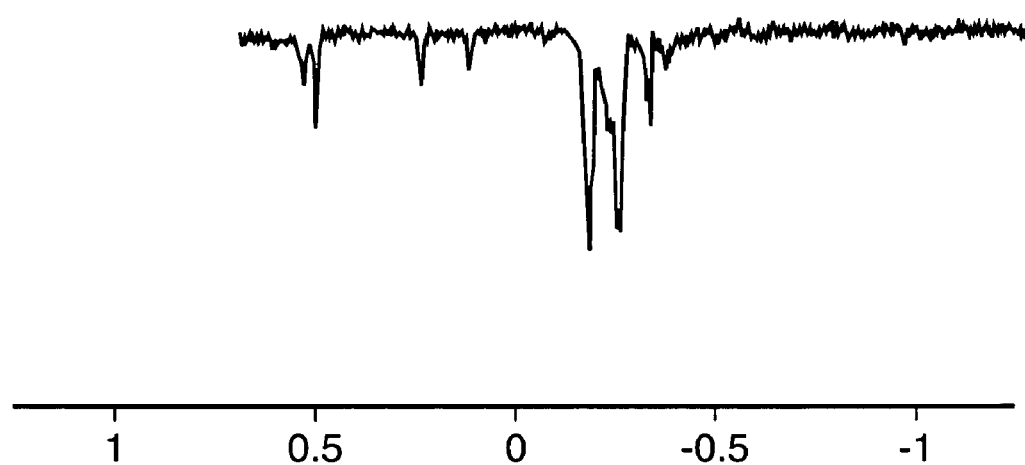

FIG. 15. Proton spectra of 0.05 M α-cyclodextrin solution in perdeuterated DMSO (dimethyl sulfoxide) at thermal equilibrium;

FIG. 16. SPINOE spectrum of α-cyclodextrin in the presence of negatively polarized $^{129}$Xe.

Figure 17:
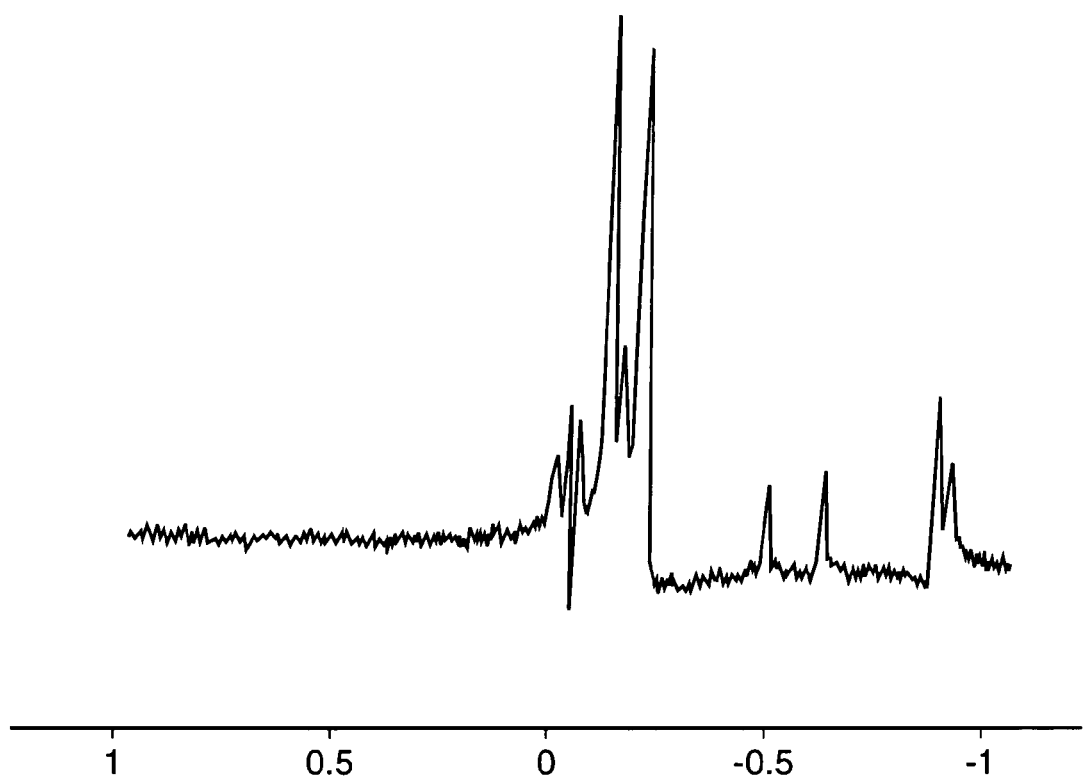

FIG. 17. SPINOE spectrum of α-cyclodextrin in the presence of positively polarized $^{129}$Xe. The positive $^{129}$Xe polarization is defined to be along the thermal equlibrium polarization. The total mixing time is 1 s and two signals were acquired for each spectrum.

Figure 18:
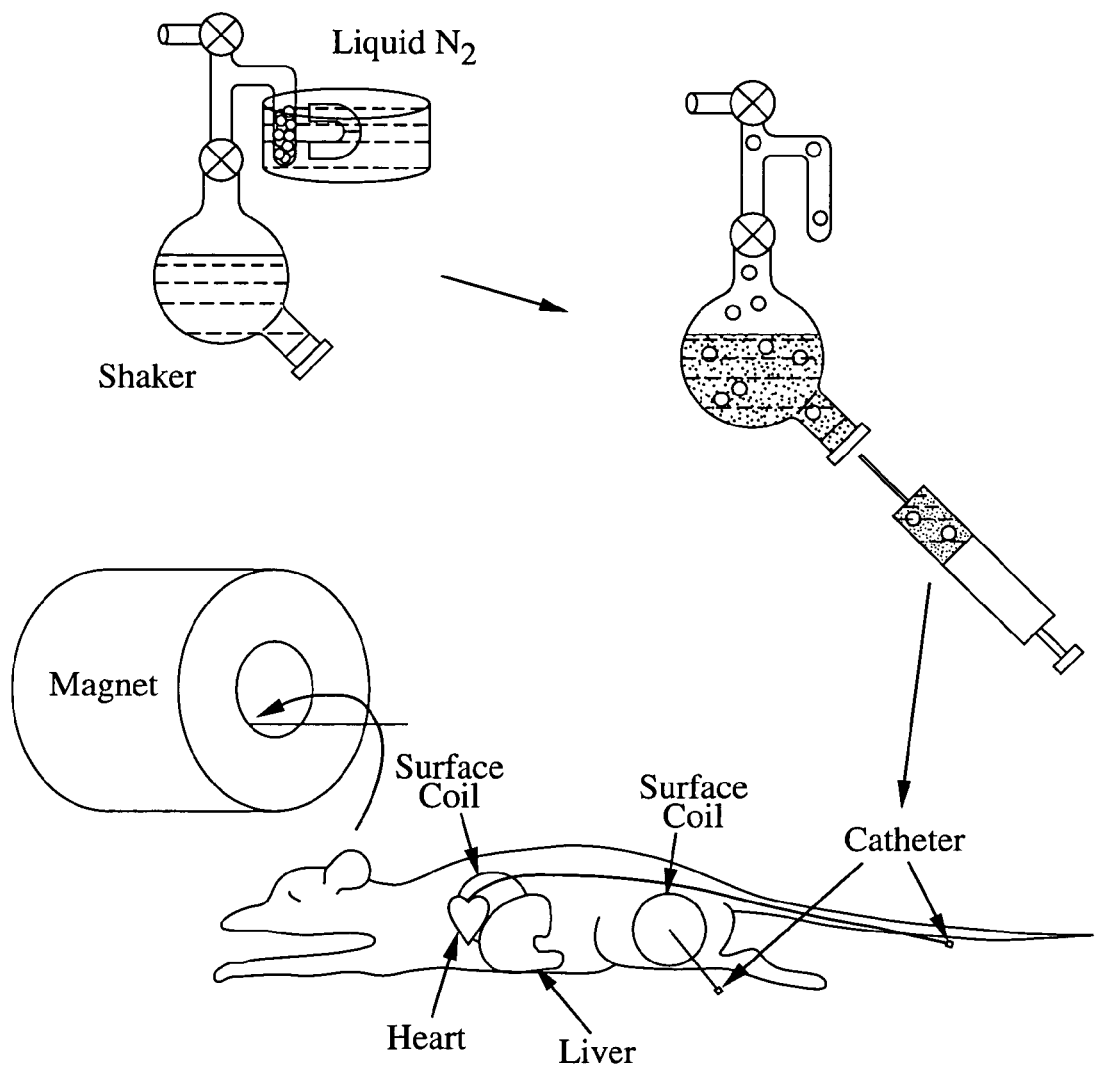

FIG. 18. Schematic diagram showing the process used for in vivo imaging of hyperpolarized 129Xe in the rat.

Figure 19A:
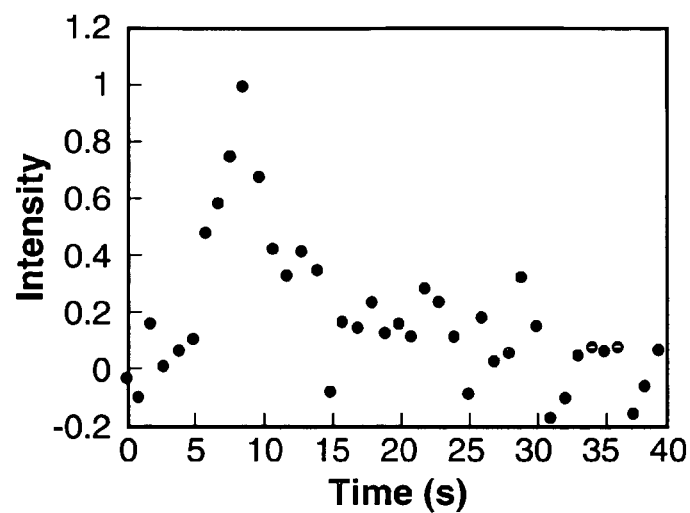
Figure 19B:
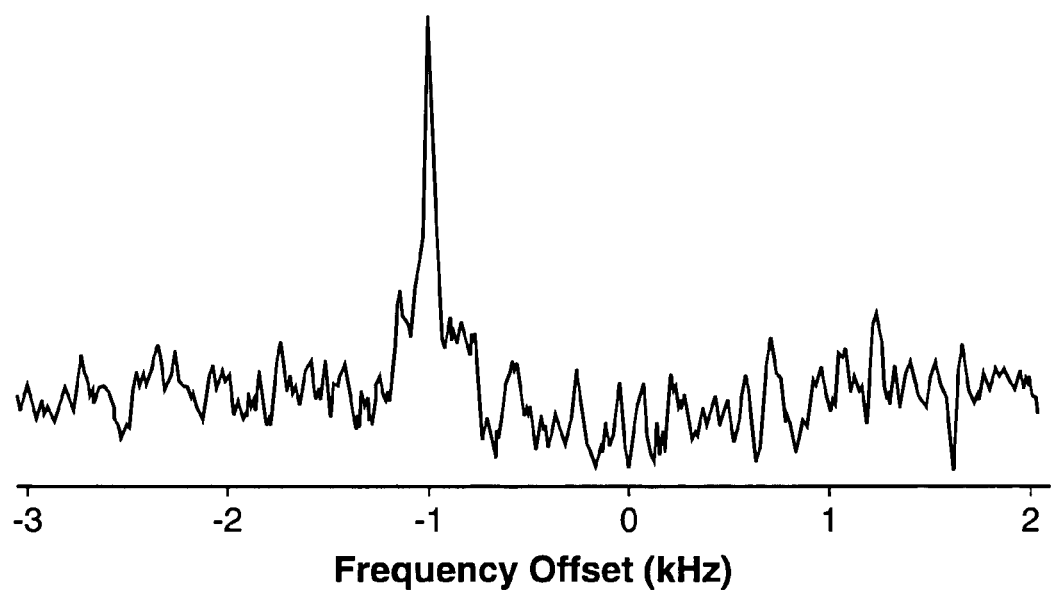

FIG. 19. A $^{129}$Xe xenon spectrum representing an average of the sixth through the twelfth scan in a series of $^{129}$Xe spectra taken over the thorax and abdomen areas following intravenous injection of a xenon/INTRALIPID® solution in the rat.

Figure 20:
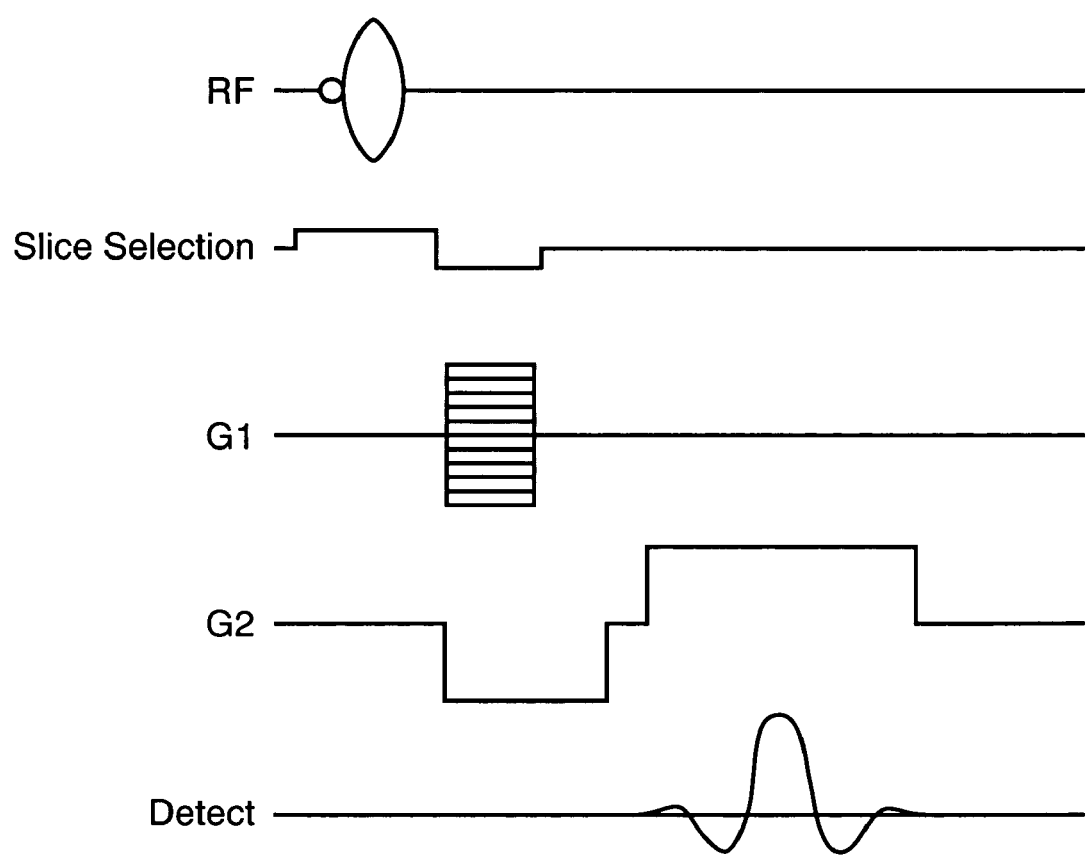
Figure 21A:
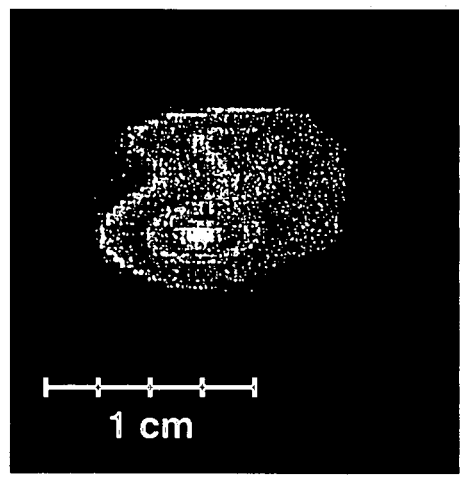
Figure 21B:
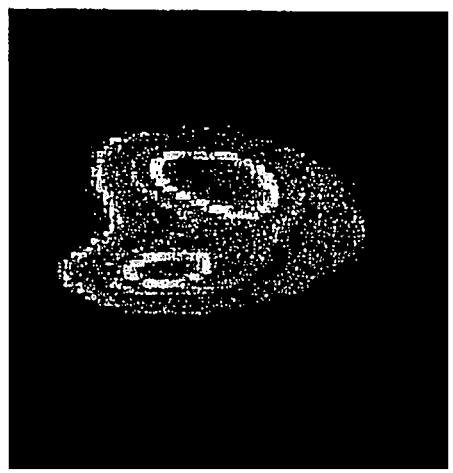
Figure 21C:
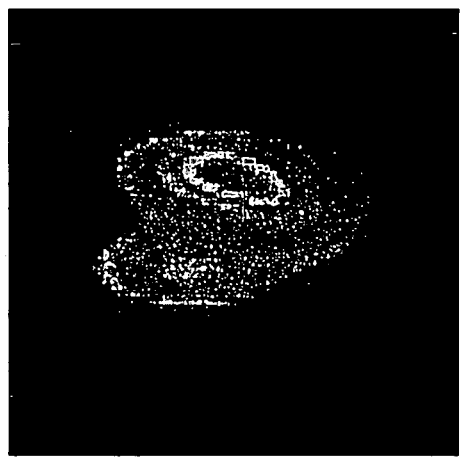
Figure 21D:
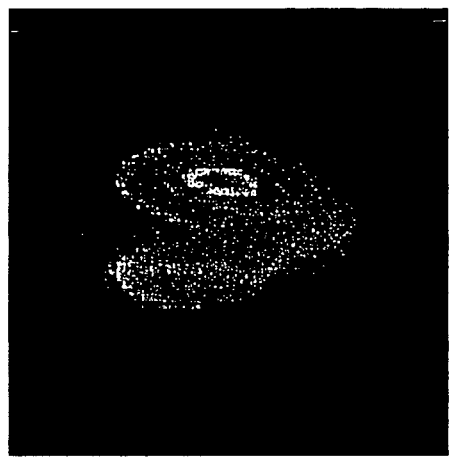
Figure 21E:
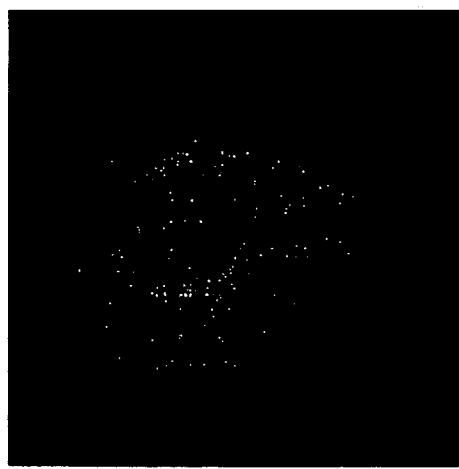
Figure 21F:
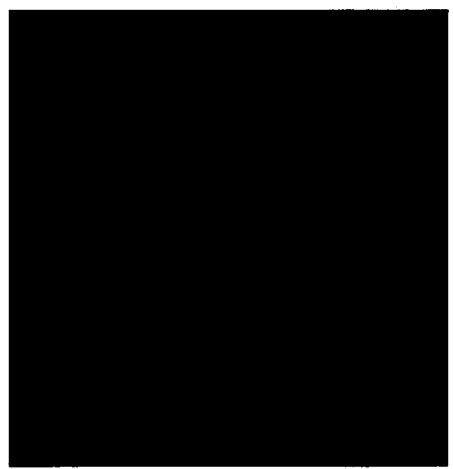

FIG. 20. Schematic diagram of the $^{129}$Xe imaging experiment showing the timing of and relationship between the excitation pulse, slice selection pulse, first and second gradients and signal detection.

FIG. 21. Two dimensional $^{129}$Xe images taken at intervals of approximately 7 seconds. The images depict the $^{129}$Xe signal intensity in the upper part of the rat's hind leg.

Figure 22:
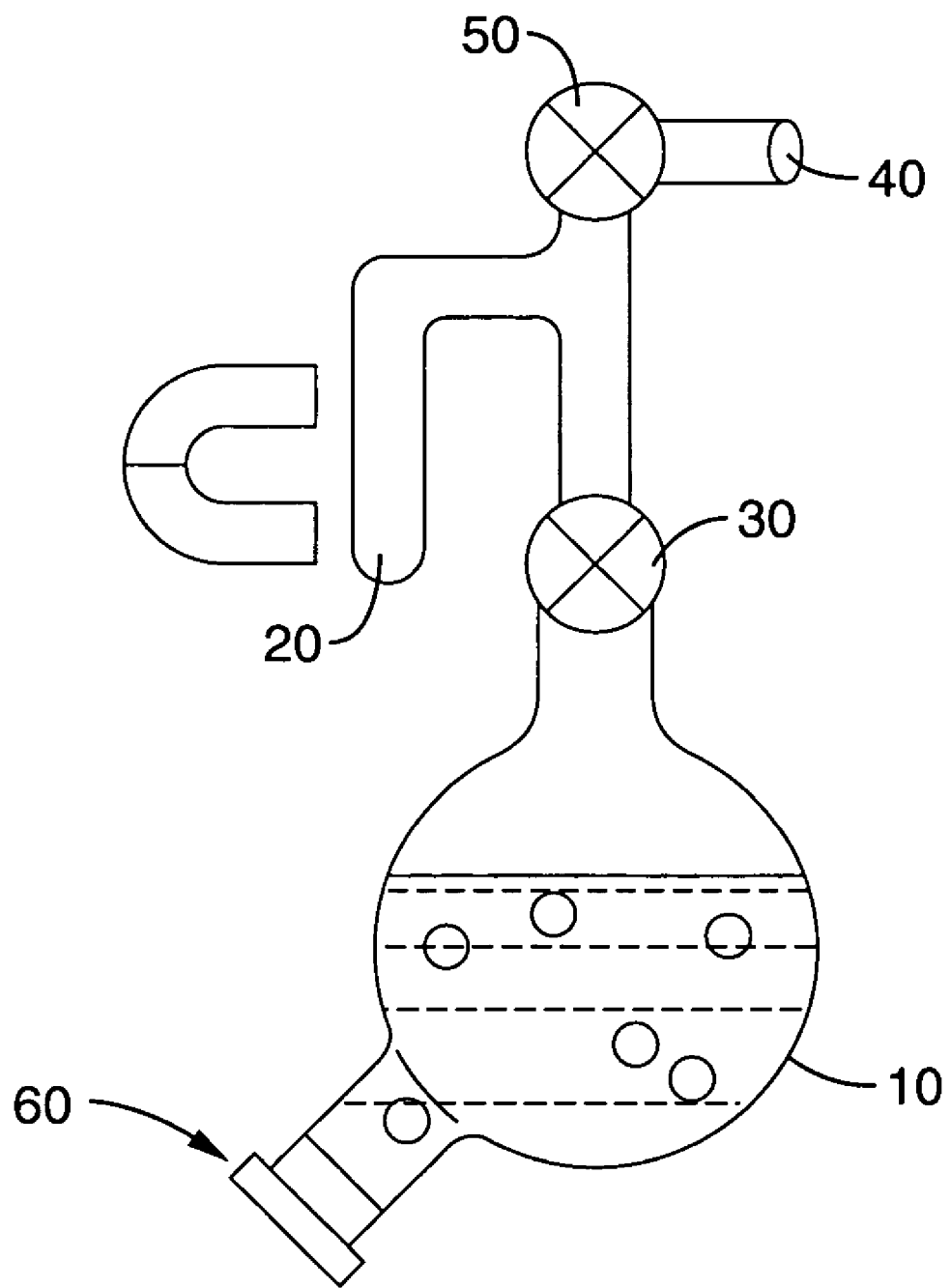

FIG. 22. A representation of one possible apparatus to accomplish the mixing of a hyperpolarized noble gas with a fluid as contemplated by this invention. The apparatus has four main subcomponents: a vessel for receiving the fluid 10, a noble gas reservoir 20, a gas inlet port 40, and a means to remove the liquid from the vessel 60. The reservoir and the vessel are connected by means of a shutoff valve 30. Similarly, the reservoir and the gas inlet port are connected via a shutoff valve 50.

DETAILED DESCRIPTION OF THE INVENTION AND PREFERRED EMBODIMENTS

It has been discovered that when a hyperpolarized noble gas (e.g., $^{129}$Xe) is dissolved in liquid solvents, a time dependent departure of, e.g., the proton spin polarization from its thermal equilibrium is observed. The variation of the magnetization, positive or negative depending on the sign of the spin polarization of the noble gas, is an unexpected manifestation of the nuclear Overhauser effect (NOE), a consequence of cross relaxation between the spins of the solution protons and the dissolved hyperpolarized noble gas. Time-resolved magnetic resonance images of both nuclei, $^1$H and dissolved noble gas, in solution show that the proton magnetization is selectively perked in regions containing the spin-polarized noble gas. Thus, it has now been determined that optical pumping and the nuclear Overhauser effect can effectively be used to transfer enhanced polarization from hyperpolarized noble gas to solution phase species without requiring the need for radiofrequency irradiation of the perturbing spins, an effect which is denoted Spin Polarization Induced Nuclear Overhauser Effect (SPINOE). Thus, SPINOE can advantageously be used to enhance the sensitivity of NMR and, in turn, to better determine the primary structure, conformation and local dynamic properties of the molecules in a liquid solution.

As such, in one aspect, the present invention provides a method for analyzing a sample containing an NMR active nucleus. This method comprises:

(a) contacting the sample with a hyperpolarized noble gas;
(b) scanning the sample using nuclear magnetic resonance spectroscopy, magnetic resonance imaging, or both nuclear magnetic resonance spectroscopy and magnetic resonance imaging; and (c) detecting the NMR active nucleus, wherein the NMR active nucleus is a nucleus other than a noble gas.

The term "contacting" is used herein interchangeably with the following: combined with, added to, dissolved in, mixed with, passed over, flowed over, administered to, injected into, ingested by, etc. The sample can be contacted with the hyperpolarized noble gas in a liquid, solid or gas phase. Further, the sample studied may be a liquid, solid, a combination of a liquid and a solid or the boundary between a solid and a liquid. Prior to contacting the sample with the hyperpolarized noble gas, it may be desirable to freeze the noble gas to preserve the hyperpolarization. Further, freezing the gas in a magnetic field can preserve the hyperpolarization for a period which is significantly longer than that obtained simply by freezing the gas. For those noble gases which freeze at temperatures which are difficult to achieve, it is within the scope of this invention to cool those gases to a temperature above their freezing point. This procedure is encompassed by the term "freezing." Similar to that described above, such cooling can also occur in the presence of a magnetic field Once contacted with the noble gas, the sample can be scanned using NMR, MRI or both. The sample is scanned to detect the effects of the hyperpolarized gas on NMR active nuclei within the sample. Any non-noble gas NMR active nucleus can be detected. As used herein, "NMR active nucleus" denotes those nuclei which have a nonzero spin quantum number. Such NMR active nuclei include, but are not limited to, $^1$H, $^{13}$C, $^{15}$N, $^{19}$F, $^{29}$Si, $^{31}$P and combinations thereof. In preferred embodiments, multiple NMR active nuclei are detected. By detecting the effects of the hyperpolarized noble gas on the sample, one can readily analyze the structure, chemistry, spatial distribution, etc. of the sample.

In another aspect, the present invention provides a method for analyzing a sample which is based on the discovery that a noble gas can be combined with a fluid to form a mixture and, in turn, the mixture can be delivered to blood or other tissue while the noble gas still has a large off-equilibrium nuclear spin polarization. Thus, this method comprises: (a) combining a hyperpolarized noble gas with a fluid to form a mixture; (b) contacting the sample with the mixture; and (c) scanning the sample, the noble gas or both the sample and the noble gas by nuclear magnetic resonance spectroscopy, magnetic resonance imaging or both nuclear magnetic resonance spectroscopy and magnetic resonance imaging.

As used herein, the term "fluid" includes, but is not limited to water, saline, phosphate buffered saline, aqueous bufffer solutions, fluorocarbons, fluorocarbon solutions in water or organic solvents, aqueous fluorocarbon emulsions, lipids, solutions of lipids organic solvents, aqueous emulsions of lipids, organic solvents (e.g., DMSO, ethanol, etc.). "Aqueous" encompasses solutions and emulsions prepared with $^1H_2O$, $^2H_2O$ or $^3H_2O$. The terms "fluid," "liquid" and "liquid carrier" are used interchangeably herein.

In preferred embodiments, the noble gas is selected from the group consisting of xenon, helium, neon, krypton and mixtures of these gases. In more preferred embodiments, the noble gas is xenon and in particularly preferred embodiments, the noble gas is either $^{129}Xe$ or $^{131}Xe$. In this method, it is desirable to pre-dissolve the hyperpolarized noble gas in a fluid which can, for example, prolong its relaxation time when the hyperpolarized xenon is in contact with physiological fluids. For instance, if the hyperpolarized gas is to be injected into blood, it is desirable to first pre-dissolve the hyperpolarized gas in a lipid, lipid solution or lipid emulsion to form a mixture which, in turn, is injected into the blood. Also desirable is dissolving the hyperpolarized noble gas in a fluorocarbon, fluorocarbon solution or fluorocarbon emulsion. The means of making such lipid and fluorocarbon formulations will be apparent to those of skill in the art. Moreover, it may be desirable to use a hyperpolarized noble gas to polarize a fluid which, in turn, is used as the contrasting agent or probe. For instance, it may be desirable to polarize water by combining it with a hyperpolarized noble gas and, thereafter, use the polarized water as the contrasting agent or probe. It may also prove advantageous to dissolve the noble gas in a liquid prior to hyperpolarizing the noble gas.

In another aspect, the present invention provides a pharmaceutical composition comprising a hyperpolarized noble gas dissolved in a physiologically compatible liquid carrier. In preferred embodiments, the liquid carrier is compatible with administration of the hyperpolarized gas by percutaneous, intravenous, oral, intraperitoneal, intramuscular or inhalation routes. In certain more preferred embodiments, the liquid carrier is appropriate for administration to an organism via an intravenous route.

As noted above, the hyperpolarized noble gas is combined with a fluid or liquid carrier which is chemically, biologically or materially compatible with the sample to be analyzed or, in some instance, dissolves as much of the noble gas as possible. Fluids suitable for use in the methods of the present invention include, but are not limited to, water, saline water, isotonic buffers, lipids, lipid emulsions, organic solvents, fluorocarbon blood substitutes and other medically safe intravenous or oral media in which the noble gas relaxation time is sufficiently long.

In preferred embodiments, the fluid in which the noble gas is dissolved is a fluorocarbon or aqueous perfluorocarbon emulsion. Preferred species are perfluorocarbons including, but not limited to, perfluorodecalin, perfluoro-1,3-dimethylcyclohexane, perfluorohexane(s), perfluorohexyl iodide, perfluoro(methylcyclohexane), perfluoro(methyldecalin), perfluoro-2-methyl-2-pentene, perfluorononane, perfluorooctane(s), perfluorobutylamine and perfluorotriethylamine. The only caveat to the use of perfluorcarbons is that, where it is desired to use fluorocarbons in vivo, the fluorocarbons must be compatible with the biological system under study. Those of skill in the art will readily be able to discern whether the fluorocarbon is compatible with the biological system. For in vitro applications, such compatibility is desirable but is not essential.

Particularly preferred fluorocarbons are those known in the art to be safe for in vivo administration. Of those safe for in vivo administration, perfluorocarbons which are useful as blood substitutes are the most preferred. Perfluorocarbons useful as blood substitutes are known in the art. (See, for example, Long, D. M., et al. in BLOOD SUBSTITUTES, Chang, T. M. S. and Geyer, R. D., Eds. Marcel Dekker, Inc. New York, 1989, pp 411-420, which is herein incorporated by reference.). Examples of perfluorocarbons used as blood substitutes include perfluorooctylbromide (PFOB), perfluortributylamine and perfluorodecalin. Fluorocarbons can be used as neat liquids, emulsions, or they can be dissolved in a solvent or injection adjuvant prior to their use.

Fluorocarbon emulsions can be formed with water, plasma, blood, buffers or other aqueous constituents. Methods of producing pharmaceutically acceptable solutions and emulsions are well known to those of skill in the art and any means known in the art for preparing these mixtures can be used to practice the instant invention. (See, Naim, J. G., in REMINGTON'S PHARMACEUTICAL SCIENCES, Vol. 17, Gennaro, A. R., Ed., Mack Publishing Co., Easton, Pa., 1985, pp. 1492-1517, which is incorporated herein by reference.).

Fluids particularly preferred in practicing the present invention are commercially available blood substitutes such as PFB-1, PFB-2 (Alliance Pharmaceutical Corp.) and FLUOSOL®. FLUOSOL®, an intravascular perfluorocarbon emulsion which is commercially available from Alpha Therapeutic Corporation (Los Angeles, Calif., U.S.A.), is exemplary of a fluorocarbon blood substitute which can be used in the methods of the present invention. Other fluorocarbons and fluorocarbon formulations useful in practicing the invention will be apparent to those of skill in the art.

In another embodiment, the noble gas is dissolved in a lipid, lipid solution or lipid emulsion. The term "lipid" refers to any oil or fatty acid derivative. The oil may be derived from vegetable, mineral or animal sources. As used herein, the term "lipid" also includes those lipids which are capable of forming a bilayer in aqueous medium, such th a hydrophobic portion of the lipid material orients toward the bilayer while a hydrophilic portion orients toward the aqueous phase. Hydrophilic characteristics derive from the presence of phosphato, carboxylic, sulfato, amino, sulfhydryl, nitro and other like groups. Hydrophobicity can be conferred by the inclusion of groups tat include, but are not limited to, long chain saturated and unsaturated aliphatic hydrocarbon groups and such groups substituted by one or more aromatic, cycloaliphatic or heterocyclic group(s). Preferred lipids are phosphoglycerides and sphingolipids, representative examples of which include phosphatidylcholine, phosphatidylethanolamine, phosphatidylserine, phosphatidylinositol, phosphatidic acid, palmitoyloleoyl phosphatidylcholine, lysophosphatidylcholine, lysophosphatidyl-ethanolamine, dipalmitoylphosphatidylcholine, dioleoylphosphatidylcholine, distearoyl-phosphatidylcholine or dilinoleoylphosphatidylcholine could be used. Other compounds lacking in phosphorus, such as sphingolipid and glycosphingolipid families, are also within the group designated as lipid. Additionally, the amphipathic lipids described above may be mixed with other lipids including triglycerides and sterols.

Particularly preferred in practicing this embodiment of the present invention is the use of a commercially available lipid preparation such as 10% or 20% INTRALIPID® (Clintec Nutrition, Deerfield, Ill., U.S.A.), or 10% or 20% LIPOSYN® II, or 10% or 20% LIPOSYN® III. LIPOSYN® is an intravenous fat emulsion which is commercially available from Abbot Laboratories (Abbot Park Ill., U.S.A.), and is exemplary of a lipid emulsion which can be used in the methods of the present invention. Lipid emulsions are particularly useful because they dissolve the noble gases and, in addition, because the noble gases have long relaxation times in such lipids. Other lipids, lipid mixtures and fluids in general which are suitable for use in accordance with the present invention will be apparent to those of skill in the art.

It should be noted that it is often desirable to add a deuterated or partially deuterated solvent to the mixture. Moreover, intramuscular injection adjuvants, such as DMSO, vitamin E, etc., can also be used as carriers of the noble gas. Many of these fluids are readily available from commercial sources. Other compounds which are solvents for noble gases and also have pharmaceutically acceptable or pharmacologically useful properties will be apparent to those of skill in the art.

In certain preferred embodiments, the fluid into which the noble gas is dissolved will have the property of specifically or selectively targeting a specific organ or tissue within an organism. Many methods of achieving such targeting are known in the art. For example, lipid vesicles (liposomes) are known to be rapidly scavenged by the cells of the reticuloendothelial system (RES). Thus, in one embodiment, polarized noble gas is targeted to the RES by its incorporation into a liposome. Certain liposomes ("Stealth liposomes") are known which avoid the cells of the RES and remain primarily intravascular over their period of in vivo residence. Thus, in another embodiment, the hyperpolarized noble gas is incorporated into a "Stealth liposome" and is used as an intravascular agent. Other liposomes for use in the present invention include temperature sensitive liposomes, target-sensitive liposomes and pH-sensitive liposomes. Each of these liposomes is well known in the art. (See, Oku, N. LIPOSOMES, pp. 24-33, in POLYMERIC DRUGS AND DRUG DELIVERY SYSTEMS, Dunn, R. L., et al., Eds. ACS Symposium Series 469, American Chemical Society, Washington, D.C., 1991, which is herein incorporated by reference.).

The use of molecules which have a chemical avidity for receptors on cell surfaces to deliver pharmaceutical agents to those cells is well known in the art. It is within the scope of the instant invention to dissolve a noble gas in a fluid containing a molecule with avidity for specific tissues or cells and exploit this avidity to deliver the noble gas to the tissue or cells. Each of the above-detailed embodiments can be used both in vitro and in vivo.

The above discussion regarding the use of liposomes and receptor-mediated targeting of polarized noble gases is intended to serve as an example of methods and delivery vehicles which are useful in conjunction with the present invention. These examples are not intended to define or limit the invention or the embodiments of the invention wherein the noble gas is targeted to specific tissues.

Once formed, the noble gas/liquid mixture can be combined with the sample using a number of different techniques known to those of skill in the art. For example, if the sample is a mammalian organism or a portion thereof, the mixture can be administered to the organism by, for example, injection, inhalation or ingestion. More particularly, depending upon its intended use, the noble gas/liquid mixture can be injected into the tissue of interest (if clinically harmless), or intravascularly to be delivered to the tissue of choice. In addition, the noble gas/liquid mixture can be swallowed or, alternatively, a noble gas/liquid aerosol can be inhaled for certain medical imaging applications. Once the noble gas/liquid mixture has been administered to the sample, the sample is scanned by nuclear magnetic resonance and/or by magnetic resonance imaging for purposes of molecular structural studies and/or spatial distribution. It should be noted that the noble gas/liquid mixture can be administered a single time or, alternatively, on a continuous or quasi-continuous basis.

As used herein the term "sample" encompasses diverse structures and can include an organism. "Sample" also include organic monomers and polymers, inorganic monomers and polymers, biopolymers including, but not limited to, oligopeptides, polypeptides, antibodies, proteins, oligonucleotides, polymers of ribonucleic acids (e.g., RNA, mRNA, tRNA) and deoxyribonucleic acids (DNA) including, but not limited to, chromosomes, genes and plasmids. Also encompassed within the term "sample" are carbohydrates, including oligosaccharides, polysaccharides, glycoproteins and mucopolysaccharides, lipids, blood, carbohydrates, catalysts, polymers, porous materials (e.g., surfaces, chemical reactor beds, rocks present in oil reserves), etc. A "sample" can natively contain NMR active nuclei, NMR inactive nuclei or a combination of NMR active and NMR inactive nuclei. Using the methods of the present invention, one can readily analyze the structure, chemistry, spatial distribution, etc. of such samples. Other samples which can be analyzed using the methods of the present invention will be readily apparent to those of skill in the art.

As used herein, the term "organism" refers to life forms including, for example, animals, plants, microorganisms and fungi. Methods of the invention can be used with organisms which are either living or dead. The term "organism" also encompasses portions of organisms (e.g., organs, organ group(s), tissue(s), etc.) either in situ or removed from the organism to which they are native.

The term "organ" refers to individual functional components of an organisms including heart, liver, lungs, blood, brain, muscle, etc. "Organ group" as used herein, refers to cooperative organ systems, for example, reticuloendothelial, central nervous, peripheral nervous, digestive, etc. As used herein "tissue" means a cell or an aggregate of similar cells including, for example, blood, bone, muscle, nerve, etc. That some overlap exists between the structures encompassed by the terms "organ," "organ group," and "tissue" should be recognized; these terms are not intended to be mutually exclusive.

As used herein, the term "organic monomer" refers to a small organic (i.e., carbon containing) molecule with a molecular weight typically falling within the range of from about 15 daltons to about 1000 daltons. Beyond a general adherence to the stated molecular weight range, no limitation on the structure or functionality of these molecules is intended. This term encompasses both synthetic and natural compounds. Further, an "organic monomer" may also comprise one or more inorganic molecules such as is found in, for example, organic chelates, chelating resins, organometallic compounds and metalloporphyrins.

Complementary to the term "organic monomer," and similar in definition, is the term "organic polymer" which encompasses organic molecules of a molecular weight greater than about 1000 daltons. Both synthetic and natural compounds are defined by this term. Organic polymers may include materials such as, for example, engineering plastics, textile polymers and polymers with medical applications.

As used herein, the term "inorganic monomer" refers to a small inorganic molecule with a molecular weight typically falling within the range of from about 1 dalton to about 1000 daltons. "Inorganic monomer" complements the term "organic monomer" and thus, encompasses molecules which do not incorporate carbon as part of their structure. Complementary to the term "inorganic monomer" and similar in definition is the term "inorganic polymer" which defines inorganic molecules of a molecular weight greater than 1000 daltons and encompasses both synthetic and natural polymeric materials.

The term "protein," as used herein, has the meaning commonly given it in the art and includes, for example both structural and functional (i.e., enzymes) proteins. "Protein" includes both natural and synthetic proteins produced or isolated by any means known in the art. Non-natural proteins are also encompassed by this term. Thus, for example, a protein may contain one or more mutations in the amino acid sequence of its peptide backbone. Proteins may also bear unnatural groups added as probes or to modify protein characteristics. These groups may be added by chemical or microbial modification of the protein or one of its subunits. Additional variations on the term "protein" will be apparent to those of skill in the art.

The term "oligopeptide," as used herein, refers to a peptide which is made up of 2-10 amino acid units. "Polypeptide," as used herein, refers to peptides containing greater than 10 amino acid subunits. Both "oligopeptide" and "polypeptide" refer to both natural and synthetic peptides which can contain only natural amino acids, only unnatural amino acids, or a combination of natural and unnatural amino acids.

As used herein, the term "oligonucleotide" refers to synthetic or natural nucleotide constructs made up of 2-20 nucleic acids. The oligonucleotide may be composed of either ribonucleic acids, deoxyribonucleic acids or combinations thereof "Oligonucleotides" can be made up of only natural nucleic acids, only unnatural nucleic acids or a combination of natural and unnatural nucleic acids.

As used herein, the terms "ribonucleic acid," "deoxyribonucleic acid," "chromosomes" and "genes" have the meaning normally given to them by those of skill in the art and also include modified analogs which may be produced by any means known in the art including, but not limited to, chemical synthesis and microbial synthesis.

The term "carbohydrates," as used herein, refers to both natural and synthetic saccharides, oligosaccharides, polysaccharides, glycoproteins and mucopolysaccharides. Any means known in the art to produce or isolate carbohydrates can be used to provide carbohydrates of use in practicing the instant invention.

As used herein, the term "noble gas" refers to a rare or inert gas which is a member of the zero group of the periodic table. Noble gases suitable for use in the methods of the present invention include those having a nuclear spin, i.e., a non-zero nuclear spin. Examples of such noble gases include, but are not limited to, $^3$He, $^{21}$Ne, $^{83}$Kr, $^{129}$Xe, $^{131}$Xe and combinations thereof. In a preferred embodiment, the noble gas employed is $^{129}$Xe, $^{131}$Xe or $^3$He. Although these noble gases are generally preferred, other noble gases may be preferred in different applications because of their different physical, chemical association and magnetic resonance properties. Additionally, in some instances, it may be preferred to use a combination of noble gases, e.g., $^{129}$Xe and $^3$He.

In another aspect, the present invention provides a method for studying a property of a noble gas in a tissue. The method comprises: (a) hyperpolarizing a noble gas; (b) dissolving the hyperpolarized noble gas in a physiologically compatible liquid carrier to form a mixture; (c) contacting the tissue with the mixture from (b); and (d) scanning the tissue by nuclear magnetic resonance spectroscopy, magnetic resonance imaging, or both, whereby the property of the noble gas in the tissue is studied.

In this aspect of the invention, the tissue studied may be any tissue of the organism. The tissue may be studied in situ or removed from the organism to which it is native. In preferred embodiments of this aspect of the invention, the tissue studied is a tissue of the central or peripheral nervous system. In particularly preferred embodiments, the tissue is a component of the central nervous system such as the brain, spinal cord, blood-brain barrier or cerebrospinal fluid and the studied property of the noble gas in the tissue may be either a functional or a structural property.

As used herein, the term "property" encompasses NMR parameters, functional properties and structural properties. The term "NMR parameter" refers to frequency shift, chemical shift, scalar coupling, dipolar coupling, relaxation time (e.g., $T_1$, $T_{1\rho}$, $T_2$, $T_2^*$, etc.). Both functional and structural properties can be derived from the NMR parameters of the system under observation.

The term "functional property," as used herein, refers to the properties of a noble gas interacting with a tissue and includes properties such as, but not limited to, the mechanism of exchange of the noble gas between the intracellular and extracellular compartments, the exchange rate of the noble gas between the intracellular and extracellular compartments of a tissue, the residence time of the noble gas in the intracellular or extracellular compartment, the effect of the noble gas on the chemistry or metabolism of the cell and the concentration of the noble gas in the extracellular or intracellular compartment of the tissue.

As used herein, the term "structural property" refers to the properties of a noble gas interacting with a tissue and includes properties such as, but not limited to, the spatial distribution of the noble gas within the intracellular or extracellular compartment of a tissue and the location and identity of sites which bind the noble gas within the intracellular compartment, extracellular compartment or the membrane separating the compartments.

In one preferred embodiment, the property studied is the mechanism of exchange of the noble gas between the intracellular and extracellular compartments of a tissue. In another preferred embodiment, the tissue studied is a tissue of the peripheral or central nervous system. In a more preferred embodiment, the property studied is the mechanism of noble gas exchange between the intracellular and extracellular compartments of a tissue of the central nervous system.

In still another aspect, the invention provides a method for enhancing the relaxation time of a hyperpolarized noble gas in contact with a physiological fluid. In this aspect, the method of the invention comprises: (a) forming a hyperpolarized noble gas intermediate solution by dissolving the hyperpolarized noble gas in a fluid in which the relaxation time of the hyperpolarized noble gas is longer than the relaxation time of the noble gas in the physiological fluid; and (b) contacting the physiological fluid with the intermediate solution.

As used herein, the term "physiological fluid" encompasses the various intracellular and extracellular fluids which are found in an organism. Such physiological fluids include, but are not limited to, blood, plasma, lymph, cerebrospinal fluid, bile, saliva, gastric fluids, vitreous humor, cytoplasm, etc.

As used herein, the term "relaxation time" refers to the time required for a nucleus which has undergone a transition into a higher energy state to return to the energy state from which it was initially excited. Regarding bulk phenomena, the term "relaxation time" refers to the time required for a sample of nuclei, the Boltzmann distribution of which has been perturbed by the application of energy, to reestablish the Boltzmann distribution. The relaxation times are commonly denoted $T_1$ and $T_2$. $T_1$ is referred to as the longitudinal relaxation time and $T_2$ is referred to as the transverse relaxation time. Other relaxation times of relevance include, but are not limited to $T_{1p}$ (the paramagnetic contribution to the longitudinal relaxation rate) and $T_2^*$ (the transverse relaxtion time including the effect of $B_0$ inhomogeneity). As used herein, the term "relaxation time" refers to the above-described relaxation times either together or in the alternative. Other relevant relaxation times will be apparent to those of skill in the art. An exhaustive treatise on nuclear relaxation is available in Banci, L, et al. NUCLEAR AND ELECTRON RELATION, VCH, Weinheim, 1991, which is herein incorporated by reference.

In a preferred embodiment of this aspect of the invention, the fluid into which the hyperpolarized noble gas is dissolved is a fluorocarbon or lipid, as described above. In a more preferred embodiment, the fluid is an aqueous emulsion of either a fluorocarbon or a lipid, or is an aqueous emulsion of a combination of a fluorocarbon and a lipid.

In an additional aspect the invention provides a method for measuring a signal transferred from a hyperpolarized noble gas atom to a non-noble gas NMR active nucleus, comprising: (a) contacting the non-noble gas NMR active nucleus with the hyperpolarized noble gas atom; (b) applying radiofrequency energy to the non-noble gas NMR active nucleus in a magnetic field; and (c) measuring the signal transferred from the hyperpolarized noble gas atom to the non-noble gas NMR active nucleus using nuclear magnetic resonance spectroscopy, magnetic resonance imaging, or both.

In preferred embodiments, the non-noble gas nucleus is a biologically relevant nucleus such as, but not limited to, $^1H$, $^{13}C$, $^{15}N$, $^{31}P$, etc. In a particularly preferred embodiment, the nucleus is a proton.

In yet another aspect, the invention provides a pulse sequence for heteronuclear difference spin polarization induced nuclear Overhauser effect (SPINOE) NMR of a system comprising a hyperpolarized noble gas and a non-noble gas NMR active nucleus. The pulse sequence comprises: (a) a non-noble gas NMR active nucleus $\pi/2$ pulse; (b) a non-noble gas NMR active nucleus $\pi$ pulse applied simultaneously with application of a noble gas $\pi$ pulse; and (c) a non-noble gas NMR active nucleus $\pi/2$ pulse.

As used herein, the term "non-noble gas $\pi$ pulse" denotes a radiofrequency pulse, at the resonant frequency of a non-noble gas nucleus, which is delivered to the system and is of a duration sufficient to rotate the bulk magnetization of the sample of non-noble gas nuclei by 180°. Similarly, a "noble gas $\pi$ pulse" refers to a radiofrequency pulse sufficient to rotate the bulk magnetization of noble gas sample by 180°. A "non-noble gas NMR active nucleus $\pi/2$ pulse" will rotate the bulk magnetization of a sample of protons by 90°. Means of delivering these pulses to the system under observation will be apparent to those of skill in the art.

The pulse sequence embodied in this aspect of the invention can be used to obtain information related to the transfer of polarization from a hyperpolarized noble gas to a non-noble gas NMR active nucleus such as a proton. In a preferred embodiment, the pulse sequence is used to study regions of a structure that bind to or otherwise interact with the hyperpolarized noble gas. In other preferred embodiments, the pulse sequence is used to study a macromolecule such as a protein, polysaccharide, polypeptide, oligonucleotide, or any other molecule which interacts with a hyperpolarized noble gas in a NMR or MRI discernable manner. In still another preferred embodiment, the hyperpolarized noble gas is dissolved in a fluid prior to its administration to a tissue.

In another embodiment, the invention provides an apparatus for preparing a solution of a hyperpolarized noble gas. The apparatus comprises: a vessel for receiving the fluid; a reservoir for receiving the hyperpolarized noble gas, the reservoir communicating through a first shutoff valve with the vessel, the reservoir being shaped to allow the reservoir to be cooled independently of the vessel; a gas inlet port communicating through a second shutoff valve with the reservoir; and a means for withdrawing the fluid from the vessel independently of the shutoff valve.

The apparatus can be constructed of any material with the caveats that the material does not speed the relaxation of the hyperpolarized gas and must be capable of withstanding the temperatures necessary to freeze the noble gas and the temperature shifts between the temperature used to freeze the noble gas and room temperature or higher. Thus, the apparatus can be constructed of, for example, glass, pyrex, metal or plastic.

The limitations on the shape and size of the components are minimal. The only essential limitation being that the noble gas reservoir is capable of being cooled separately from the fluid vessel. Thus, it is within the scope of the invention to have a reservoir which is a side-arm, flask or other receptacle pendent off of the fluid vessel. The reservoir may also be separable from the rest of the apparatus by means of a joining means such as, for example, tubing, hoses, ground-glass joints, ball-and-socket joints, or any other joining means known to those of skill in the art. When large volumes of gas and/or fluid are to be used, it is particularly preferred that the apparatus be composed of separable components (i.e., reservoir and vessel) which can be assembled and disassembled as need be to facilitate the purpose of the apparatus.

The shutoff valves between the main components of the apparatus comprise any means of reversibly separating two attached vessels known in the art. Thus, it is within the scope of the invention to use a stopcock, septum, valve, check-valve, pressure-release valve, etc. Similarly, the means to remove the fluid from the vessel may comprise any means known in the art to reversibly seal a vessel. These include, but are not limited to, stopcocks, septa, membranes, break-seals, caps, plugs, break-seals, etc.

In a preferred embodiment, the apparatus further comprises a means for freezing the hyperpolarized noble gas in the reservoir for receiving the hyperpolarized noble gas. The means to freeze the gas may consist of any means known in the art for attaining temperatures sufficiently low to freeze a noble gas. These include, but are not limited to, liquid gases, circulating baths and refrigeration units.

In another preferred embodiment, the apparatus further comprises a means for applying a magnetic field to the frozen hyperpolarized noble gas to preserve the hyperpolarization prior to forming the mixture between the hyperpolarized gas and the fluid. Any means known in the art for applying a magnetic field will be useful in the instant invention. These include, but are not limited to, permanent magnets, electromagnets, superconducting magnets and the magnet in an NMR spectrometer or imaging device.

As noted above, the noble gas used in the methods of the present invention is hyperpolarized relative to its normal Boltzmann polarization. Noble gases can be hyperpolarized for use in accordance with the present invention through any of various means known to and used by those of skill in the art. Such methods: include, but are not limited to, spin-exchange interactions with optically pumped alkali metal vapor and direct pumping by a metastable state. It will be readily apparent to those of skill in the art that other methods can also be used to hyperpolarized the noble gases used in the present invention. In a preferred embodiment, optical pumping using circularly polarized light is used to produce a hyperpolarized gas.

The term "optical pumping" generally refers to the redistribution of atoms among their fine- or hyperfine-structure levels by means of light. The light can be circularly polarized, anisotropic, filtered or amplitude-modulated. In preferred embodiments, the light is circularly polarized. Using relatively simple techniques known to those of skill in the art, it is possible to produce useful polarization of atoms, nuclei and electrons. For example, see, Carver, T. R., *Science,* 141(3581):599-608 (1963), for a detailed review of optical pumping In addition, the details of an optical-pumping apparatus suitable for use in accordance with the present invention are described, for example, by Raftery, et al., *Phys. Chem.,* 97: 1649 (1993); and Song, et al., *J. Magnet. Res.* 115: 127-130 (1995). The teachings of the above-cited references are incorporated herein by reference.

The optical pumping and spin-exchange can be performed in the absence of an applied magnetic field, but are preferably performed using modest fields of about 1 G or larger. Pumping in the NMR magnet bore at fields of several Tesla is also possible. The maximum steady state nuclear polarization achievable depends on the time constant characterizing the spin exchange with the alkali metal and the time constant characterizing the relaxation ($T_1$) due, for example, to contact with the surfaces of the pumping cell. For instance, with $^{129}$Xe, $T_1$=20 min. polarizations of 20-40% are quite practicable, and polarizations of 90% or more should be attainable.

Hyperpolarizing noble gases through spin exchange with an optically pumped alkali-metal vapor starts with the irradiation of the alkali-metal vapor with circularly polarized light at the wavelength of the first principal ($D_1$) resonance of the alkali metal (e.g., 795 nm for Rb). The $^2S_{1/2}$ ground state atoms are thus excited to the $^2P_{1/2}$ state and subsequently decay back to the ground state. If performed in a modest (10 Gauss) magnetic field aligned along the axis of incident $D_1$ light, this cycling of atoms between the ground and first excited states leads to nearly 100% polarization of the atoms. This polarization is carried mostly by the lone valence electron characteristic of all alkali metals; this essentially means that all of these electrons have their spin either aligned or anti-aligned to the magnetic field depending upon the helicity (right- or left-handed circular polarization state) of the pumping light. If a noble gas with non-zero nuclear spin is also present, the alkali-metal atoms can undergo collisions with the noble gas atoms in which the polarization of the valence electrons is transferred to the noble-gas nuclei through a mutual spin flip. This spin exchange results from the Fermi-contact hyperfine interaction between the electron and the noble-gas nucleus. By maintaining the alkali-metal polarization at nearly 100% with the pumping light, large non-equilibrium polarizations (5%-80%) are currently achievable in large quantities of a variety of noble gases through this spin-exchange process. For example, one currently available Titanium:Sapphire-laser can theoretically provide 1 g/hr (200 cc-atm/hr) of highly polarized $^{129}$Xe. Even more product is expected from the use of modem diode array lasers.

The alkali metals capable of acting as spin exchange partners in optically pumped systems include any of the alkali metals. Examples of alkali metals suitable for use in this hyperpolarization technique include, but are not limited to, $^{23}$Na, $^{39}$K, $^{85}$Rb, $^{87}$Rb and $^{133}$Cs. In a presently preferred embodiment, $^{85}$Rb and $^{87}$Rb are the alkali metal isotopes employed.

In addition to optical pumping, the noble gas may be hyperpolarized using metastability exchange. The technique of metastability exchange involves direct optical pumping of, for example, $^3$He, without need for an alkali metal intermediary. The method of metastability exchange usually involves the excitation of ground state $^3$He atoms ($1^1S_0$) to a metastable state ($2^3S_1$) by weak radio frequency discharge. The $2^3S_1$ atoms are then optically pumped using circularly polarized light having a wavelength of 1.08 μm in the case of $^3$He. The light drives transitions up to the $2^3P$ states, producing high polarizations in the metastable state to which the $2^3P$ atoms then decay. The polarization of the $2^3S$, states is rapidly transferred to the ground state through metastability exchange collisions between metastable and ground state atoms. Metastability exchange optical pumping will work in the same low magnetic fields in which spin exchange pumping works. Similar polarizations are achievable, but generally at lower pressures, e.g., about 0-10 Torr.

Prior to and independent of hyperpolarization, further enhancement of the noble gas magnetic resonance signal can be obtained by increasing the proportion of the NMR active isotope in each noble gas to a level above the natural abundance of such imageable isotopes in the noble gas. For instance, in the case of $^{129}$Xe, which has a natural isotopic abundance of about 26%, the enhancement can amount a factor of about four for a gas which is enriched to 100% $^{129}$Xe. Thus, although hyperpolarization plays a much larger role in signal enhancement, isotopic enrichment can provide a significant contribution to the ultimate efficacy of the present invention.

In the methods of the present invention, the hyperpolarized noble gas, e.g., $^{129}$Xe, can be delivered in gas, liquid or solid phases. High pressure noble gas can be conveniently obtained by first freezing into a small volume in the magnetic field followed by warming up. The noble gas is then combined with a fluid to form a mixture. Such a mixture can be formed, for example, by vigorous shaking to equilibrate quickly the noble gas in the liquid, or by other efficient means of gas/liquid mixing which are known to and used by those of skill in the art. Alternatively, porous membranes or other devices known to those of skill in the art can be used to saturate the solution with the noble gas, provided they do not significantly decrease the relaxation time of the noble gas. It should be noted that the freezing of the hyperpolarized noble gas also serves to purify the noble gas, e.g., to remove or separate out the toxic alkali metal used in the hyperpolarization, and to prolong the hyperpolarization of the noble gas during storage or shipping.

In the methods of the present invention, magnetic resonance spectroscopy and/or magnetic resonance imaging is used to detect a parameter which can be used to analyze, characterize or image a sample or a portion thereof. Parameters of the sample, the hyperpolarized noble gas or the system comprising the sample and the hyperpolarized noble gas, which are useful for such purposes include, but are not limited to, chemical shift, $T_1$ relaxation, $T_2$ relaxation and $T_{1\rho}$ relaxation. In a preferred embodiment, multiple parameters are detected. In addition, multiple techniques can be employed in the methods of the present invention to collect and manipulate nuclear magnetic resonance data. Such methods include, but are not limited to, one-dimensional and multi-dimensional spectroscopy, Fourier imaging, planar imaging, echo-planar imaging (EPI), projection-reconstruction imaging, spin-warp Fourier imaging, gradient recalled acquisition in the steady state (GRASS) imaging also known as fast low angle shot (FLASH) imaging, and hybrid imaging. For imaging purposes, preferred methods include the FLASH or GRASS imaging method and the EPI method because of their capacity to generate images through fast data acquisition, thereby conserving polarization of the noble gas.

The methods of the present invention can be used for a myriad of diverse applications including, but not limited to, tissue perfusion quantitation; longer residence time imaging of air space; new proton contrast agent; new probe of pathophysiology; new application of NMR to gastrointestinal clinical medicine; new non-toxic intravascular MRI angiography contrast agent; and protein structure elucidation by polarization transfer to protons or other nuclei in the molecule. In addition, the noble gas, when dissolved in a physiologically acceptable carrier can be utilized to study lung air-space anatomy, tissue perfusion and MRI angiography. Moreover, within the context of the methods disclosed herein, the present invention also has the following advantages. In general, hyperpolarized noble gas NMR can be used as an alternative to the imaging techniques that make use of radioactive isotopes, such as $^{127}Xe$ and $^{133}Xe$. The advantages of MRI of hyperpolarized noble gases are the zero radiation dose absorption by the patient and, in addition, a much better spatial resolution. In addition, NMR of noble gases are useful for brain studies. Specifically, magnetic resonance imaging of a hyperpolarized noble gas enables better detection of central nervous system perfusion and, thus, it is useful as a tool for diagnosis of stroke and as a flow specific tool for functional imaging. Those of skill in the art will readily appreciate that the methods of the present invention are useful for a variety of other purposes as well.

Those of skill in the art will readily appreciate that the noble gas is preferably maintained in a system which is substantially sealed to prevent loss to the atmosphere. Typically, a sealed containment apparatus will include a noble gas source, such as a gas canister or compressed gas tank, conduits to and away from a sample, as well as recovery apparatus. Moreover, a hyperpolarized noble gas may be stored for extended periods of time in a hyperpolarized state. Storage systems capable of cryogenic storage of a hyperpolarized noble gas are preferably able to maintain tempera such that noble gas is stored in frozen state. For instance, frozen $^{129}Xe$ can be reasonably maintained at fields of $\geq 500$ Gauss at temperatures ranging from 4.2K (liquid helium temperature), for which $T_1$, is about a million seconds (10 days), to 77K (liquid nitrogen temperature), for which $T_1$, is about 10 thousand seconds. The fields necessary here may be provided by a permanent magnet, a larger electromagnet or a superconducting magnet. Those of skill in the art will readily appreciate that a noble gas which has been hyperpolarized by spin exchange with an alkali metal may be stored either before or after removal of any alkali metal used in spin exchange hyperpolarization techniques. In all cases in which rubidium or other alkali metal would interfere with the behavior of the system, the alkali metal is removed before introduction of the noble gas to the sample using techniques known to and used by those of skill in the art.

The invention will be described in greater detail by way of specific examples. The following examples are offered for illustrative purposes, and are intended neither to limit or define the invention in any manner.

EXAMPLES

Materials and Methods

The following general materials and methods were used in the examples described below.

Figure 1:
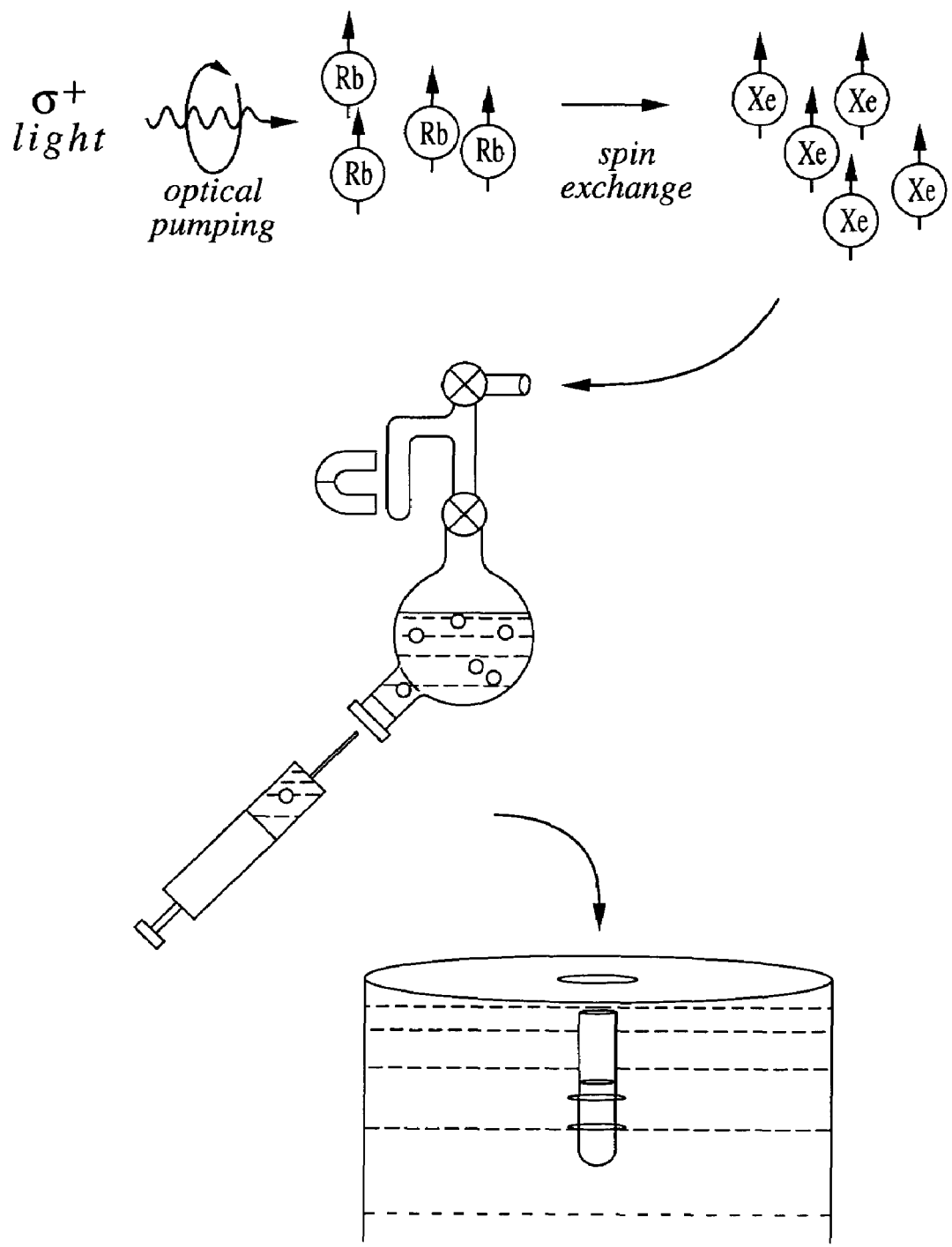
FIG. 1. A schematic is set forth of the experimental protocol used. Eighty percent of isotopically enriched $^{129}$Xe is polarized via spin exchange with optically pumped rubidium atoms using previously described techniques. The xenon is frozen at liquid nitrogen temperature in a sidearm of a sample tube in high magnetic field provided by a permanent magnet. The xenon is then brought to the gas phase by warming and admitted to the solution.

The design of the shaker used in the dissolution stage for xenon mixing and delivery is illustrated in FIG. 1. The shaker has a small sidearm which can be isolated from the main volume by a stopcock The shaker is charged with a sample of either normal abundance or isotopically enriched xenon (80% $^{129}Xe$, EG&G Mound, Miamisburg, Ohio, U.S.A.). Laser polarization is performed prior to admitting the xenon to the shaker. Briefly, approximately $5\times10^{-4}$ mol of 80% isotopically enriched $^{129}Xe$ was optically pumped in a 30 cc cylindrical glass pumping cell (diameter≈30 mm). Before optical pumping, the cell was cleaned and coated with SURFASIL® (Pierce Chemical Co., Florence, Mass., U.S.A.); the cell was then evacuated to $10^{-6}$ torr and loaded with one drop of melted rubidium metal in a dry nitrogen environment. Optical pumping was performed with a 1.3 W continuous-wave Ti:sapphire laser (794.7 nm) for 20-30 min, and

EXAMPLES

Materials and Methods

The following general materials and methods were used in the examples described below.

The design of the shaker used in the dissolution stage for xenon mixing and delivery is illustrated in FIG. 1. The shaker has a small sidearm which can be isolated from the main volume by a stopcock. The shaker is charged with a sample of either normal abundance or isotopically enriched xenon (80% $^{129}Xe$, EG&G Mound, Miamisburg, Ohio, U.S.A.). Laser polarization is performed prior to admitting the xenon to the shaker. Briefly, approximately $5\times10^{-4}$ mol of 80. % isotopically enriched $^{129}Xe$ was optically pumped in a 30 cc cylindrical glass pumping cell (diameter≈30 mm). Before optical pumping, the cell was cleaned and coated with SURFASIL® (Pierce Chemical Co., Florence, Mass., U.S.A.); the cell was then evacuated to $10^{-6}$ torr and loaded with one drop of melted rubidium metal in a dry nitrogen environment. Optical pumping was performed with a 1.3 W continuous-wave Ti:sapphire laser (794.7 nm) for 20-30 min, and the temperature of the cell was maintained at 60-80° C. by a temperature-controlled nitrogen gas stream. Typically, the apparatus produces xenon polarization levels in the range of 5-10%.

Following laser polarization, the polarized $^{129}Xe$ is frozen at liquid nitrogen temperatures in the sidearm in a magnetic field of approximately 50 mT provided by a small permanent magnet. The magnetic field is used in the freezing stage to prevent the decay of xenon polarization. The xenon is sublimated and then admitted into the solution. The small size of the shaker allows for the accumulation of several atmospheres of xenon pressure which aids in increasing the xenon concentration in the solution. During the dissolution procedure, the vessel is vigorously shaken to help dissolve the xenon gas. The resulting xenon solution is extracted with a syringe through a high-pressure rubber septum. In those examples below wherein a solution NMR study is performed on an in vitro sample, the xenon is immediately injected into an NMR tube which contains the sample to be studied. The loss of polarization during the injection procedure was found to be insignificant.

Example 1

This example describes the $^{129}$Xe NMR of a sample of hyperpolarized $^{129}$Xe dissolved in aqueous saline. The $T_1$ of xenon was measured in both $H_2O$ saline and $D_2O$/saline.

Figure 2:
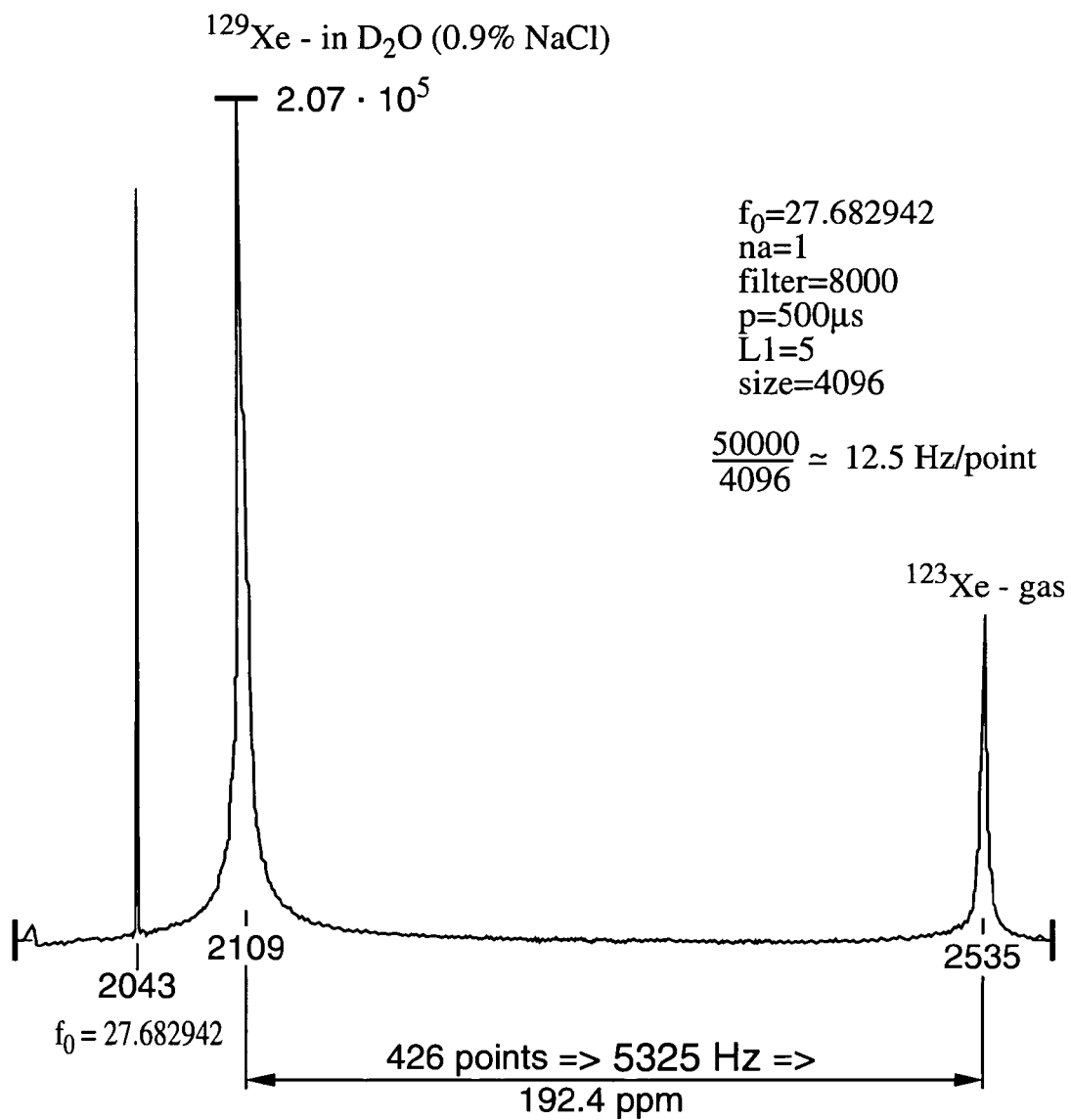
FIG. 2. $^{129}$Xe NMR spectrum of a solution of $^{129}$Xe in $D_2O$

In an NMR tube open to the atmosphere were combined saline and hyperpolarized $^{129}$Xe. The saline used had a NaCl concentration of 0.9% by weight. $^{129}$Xe was dissolved in saline as described in the materials and methods section above. Xenon has a low solubility in saline, with an Ostwald coefficient of only 0.0926 (the standard temperature and pressure volume of xenon dissolved in 1 liter of liquid at 1 atmosphere of gas pressure; 1 atm=101.3 kPa). In $H_2O$/saline, the $T_1$ of xenon is quite long (66 s at 9.4 T). The $^{129}$Xe NMR spectrum of a solution of $^{129}$Xe in $D_2O$ saline is displayed in FIG. 2. In saline made with $D_2O$, the $T_1$ of xenon is ≈1000 s. Thus, the shorter $T_1$ of xenon in $H_2O$ saline is due to dipolar couplings between the hyperpolarized xenon electrons and the proton nuclear spins.

Example 1 demonstrated the acquisition and characteristics of $^{129}$Xe spectra of hyperpolarized xenon dissolved in aqueous solution.

Example 2

This example demonstrates the use of xenon NMR to study the partition of xenon between the intracellular and extracellular compartments in a sample of human blood. The NMR of xenon in human blood was measured using both hyperpolarized and unpolarized xenon.

2.1 Materials and Methods

A sample of human blood was prepared by allowing fresh blood from a volunteer to settle for a few hours and subsequently decanting off a portion of the plasma. The portion removed accounted for approximately 30% of the total volume of the blood sample. Following removal of a portion of the plasma, xenon saturated saline (1 mL) was injected into the red blood cell (RBC) sample (1 mL) and the $^{129}$Xe NMR was measured. The NMR spectra were measured on a Bruker AM-400 spectrometer.

2.2 Results

Figure 3:
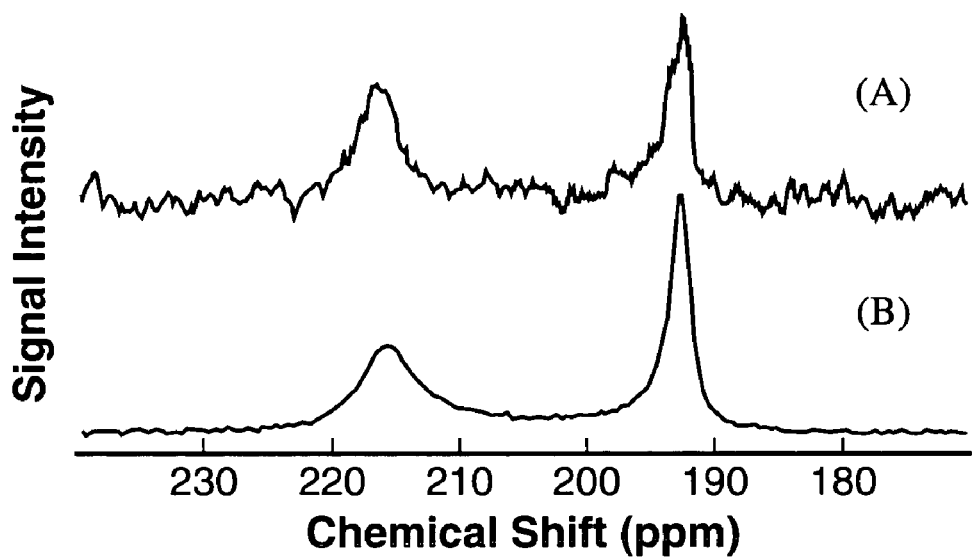
FIGS. 3A and 3B. Conventional and optically polarized $^{129}$Xe NMR spectra of xenon in blood acquired after injecting 1 cc of xenon/water mixture into 1 cc of concentrated red blood cells are set forth.

The NMR spectrum of non-polarized xenon was measured in an RBC sample (FIG. 3A). Considerable signal averaging was required in order to obtain a spectrum with an acceptable signal-to-noise ratio. The spectrum was acquired over 1.5 h and is the product of 520 scans. In marked contrast, a spectrum with an excellent signal-to-noise ratio was obtained following one scan when laser-polarized $^{129}$Xe was used (FIG. 3B). The signal enhancement obtained through using laser-polarized $^{129}$Xe, rather than non-polarized $^{129}$Xe, was estimated to be approximately 3 orders of magnitude.

The NMR spectra of both the laser-polarized and non-polarized $^{129}$Xe in the RBC sample display two peaks; 216 ppm and 192 ppm. The peak at 216 ppm arises from $^{129}$Xe which has diffused into the RBC. The peak at 192 ppm arises from the $^{129}$Xe which remains extracellular and is in the saline/plasma mixture. The significant difference between the xenon chemical shift in the RBC and that in the saline/plasma is primarily due to the xenon binding to hemoglobin.

Thus, through the use of laser polarized xenon it is possible to rapidly distinguish between intracellular and extracellular populations of $^{129}$Xe. Further, the significantly improved signal-to-noise ratio obtained in spectra measured on samples containing laser polarized $^{129}$Xe NMR spectra allows the real time observation of the dynamics of the transfer of the xenon from the saline/plasma mixture into the RBC.

Example 3

Example 3 illustrates the use of NMR spectroscopy to observe the dynamics of the mixing of laser polarized $^{129}$Xe between the intracellular and extracellular compartments of a sample consisting of red blood cells and plasma.

3.1 Materials and Methods

A sample of laser polarized xenon in saline and a RBC sample were prepared as described in Examples 1 and 2, respectively. By using short rf pulses of small tipping angle, $^{129}$Xe NMR spectra were acquired as a function of time after injection of the xenon/saline mixture into the blood. NMR spectra were measured on a Bruker AM-400 spectrometer.

3.2 Results

Figure 4:
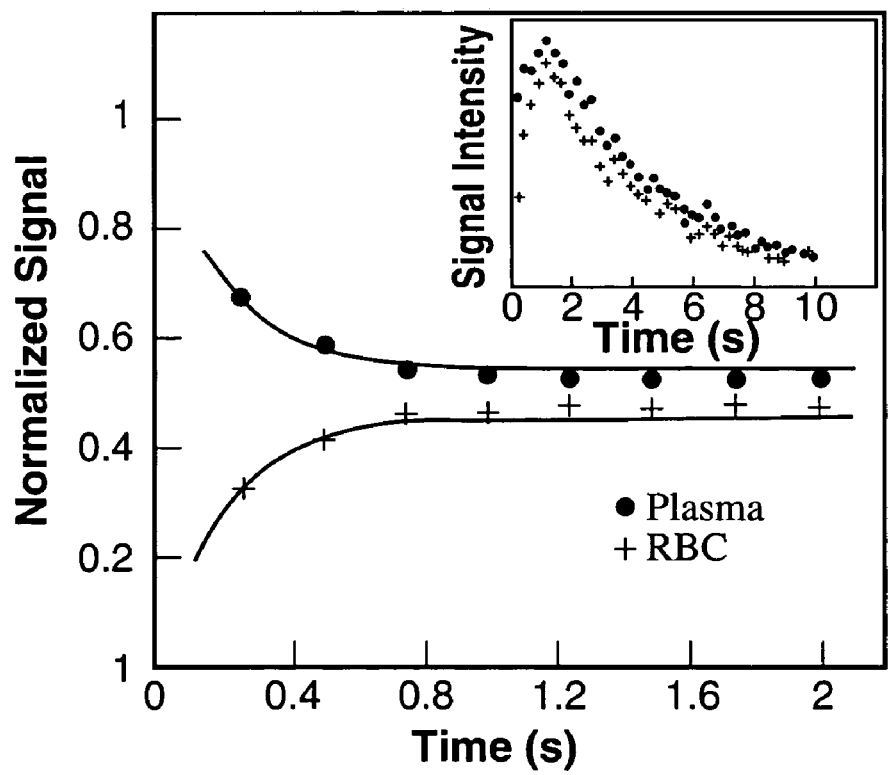
FIG. 4. The time dependence of the integrals of the two peaks in a typical $^{129}$NMR of $^{129}$Xe in blood is set forth.

The results of this experiment are illustrated in FIG. 4. In FIG. 4, the main figure shows the time dependence of the xenon signal in the RBC and in the saline/plasma, normalized by the total signal. The initial rise of the RBC signal and decrease in the saline/plasma signal indicates the transfer of xenon from the saline/plasma water mixture to the RBC during the mixing. Within the first second, the rise in the RBC signal and the reduction of the saline/plasma signal describe the dynamic process of xenon entering the RBC from the saline/plasma during mixing. The time dependence of both the RBC and saline/plasma signals during the mixing process can be described by an exponential function of the form:

$$f(t) = A + B\left(\exp\left(-\frac{t}{T}\right)\right) \quad (2)$$

where A and B are constants and the time constant (T) for this function was estimated to be about 200 ms.

The signal increase (about 1 sec) is probably due to xenon rich blood dripping from the walls of the sample tube into the detection coil after vigorous mixing. The xenon transfer from the water to the red blood cells is evident. The timescale for the process is 170±30 ms. When 1 cc of saline water is mixed with 1 cc of red blood cells, the equilibrium distribution of the integral of the two peaks is approximately 50%. Remarkably, the two peaks decay with the same rate constant (about 5 seconds). Spin-lattice relaxation time of xenon in blood measured with conventional NMR yielded two different decay rates for the 2 peaks. This is probably an artifact associated with the settling of the red blood cells during the 12 or more hours of data acquisition required for the conventional experiments. After separation of the erythrocytes from the plasma, the xenon exchange between the two compartments is very inefficient, and two different relaxation times are observed. When the red blood cells and the plasma are mixed, the exchange is fast enough to yield the same $T_1$ for the two peaks. The value for the exchange rate we have measured is consistent with this model. As the experiments have been performed in a sample tube open to air, an additional contribution to the decay of the signal may be due to xenon transfer to the air. Such mechanism would not play a role when the solution is administered intravascularly to tissues.

The inset in FIG. 4 displays the time dependence of the integrated xenon signal from both peaks in the spectra. From the decay starting after 2 seconds, the $T_1$ of the two components was found to be approximately 5.0 seconds. The initial rise in the total xenon signal intensity during the first second, following the vigorous injection and mixing of the xenon/saline solution, was most likely caused by xenon-containing blood/plasma/saline mixture descending from the walls of the sample tube into the region of the detection coil. Because the sample was unlikely to be intimately mixed and equilibrated at the start of the NMR measurements, the data acquired in the above-described example reflect primarily the xenon mixing process between the RBC and the saline/plasma.

This example illustrates the feasibility of using the techniques of the present invention to study the dynamics of noble gas exchange between the intracellular and extracellular compartments of a tissue.

Example 4

Example 4 describes the determination, using NMR spectroscopy, of the intrinsic xenon exchange rate between the RBC and the saline/plasma.

4.1 Materials and Methods

A sample of laser polarized xenon in saline and a RBC sample were prepared as described in Examples 1 and 2, respectively. By using short rf pulses of small tipping angle, $^{129}$Xe NMR spectra were acquired as a function of time after injection of the xenon/saline mixture into the blood. NMR spectra were measured on a CMX Infinity spectrometer (Chemamagnetics-Otsuka Electronics, Fort Collins, Colo., U.S.A.) at a magnetic field of 4.3 Tesla.

4.2 Results

The xenon exchange rate between the extracellular and intracellular compartments of a RBC/saline/plasma sample was measured by selectively inverting the xenon saline/plasma NMR line and observing the recovery of the two signals. The selective inversion was achieved by an amplitude-modulated Gaussian pulse of 1 ms duration centered at the frequency of the saline/plasma signal. This pulse also reduced the absolute signal intensities for the RBC and saline/plasma peaks by about 50%. A field gradient pulse of 1 ms was applied after the inversion pulse to dephase any components of the transverse magnetization. After the inversion pulse, xenon spectra were taken at fixed time intervals using a small tipping angle (20°). Following the addition of the xenon/saline solution into the RBC sample, a delay of 3 seconds before the application of the inversion pulse insured that the xenon/RBC system was well mixed and equilibrated. The results of the experiment are displayed graphically in FIG. 5A and FIG. 5B.

Figure 5A:
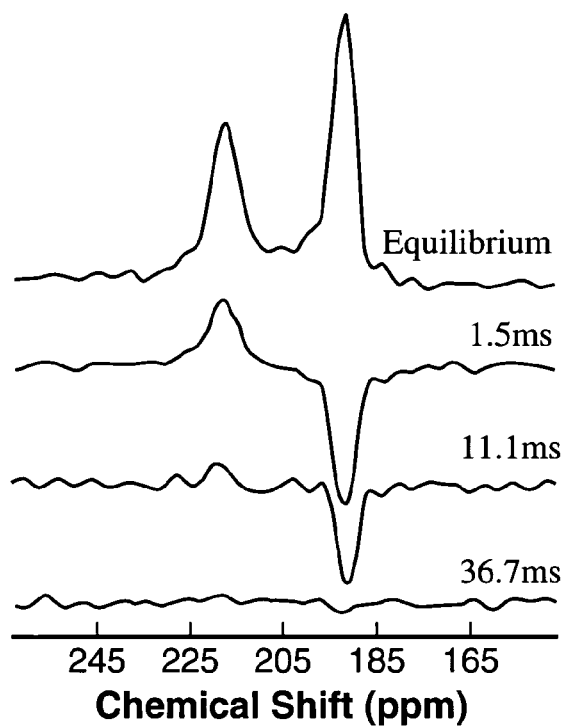
FIGS. 5A and 5B. Intrinsic exchange of xenon between the extracellular and intracellular compartments of blood.

FIG. 5A shows the initial equilibrium spectrum 13 ms before the application of the inversion pulse and three of a series of spectra which were measured after the selective inversion pulse. The exchange of xenon from the RBC to the saline/plasma is shown by the increase in amplitude of the saline/plasma signal and the corresponding reduction in the amplitude of the RBC signal. The time dependence of the signals, $S_{RBC}$ and $S_{p1}$, can be described by the following equations:

$$S_{RBC} = (S^o_{RBC} + S^o_{p1})\frac{\tau_{RBC}}{\tau_{RBC} + \tau_{p1}} + S_o\exp\left(-\frac{t}{\tau}\right), \quad (3)$$

$$S_{p1} = (S^o_{RBC} + S^o_{p1})\frac{\tau_{p1}}{\tau_{RBC} + \tau_{p1}} - S_o\exp\left(-\frac{t}{\tau}\right), \quad (4)$$

$$S_o = S^o_{RBC}\frac{\tau_{p1}}{\tau_{RBC} + \tau_{p1}} - S^o_{p1}\frac{\tau_{RBC}}{\tau_{RBC} + \tau_{p1}}, \quad (5)$$

where $\tau_{RBC}$ and $\tau_{p1}$ are residence time constants for xenon in the RBC and saline/plasma, and $1/\tau = 1/\tau_{RBC} + 1/\tau_{p1}$. $S^o_{RBC}$ and $S^o_{p1}$ are the initial intensities for the RBC and the plasma/saline components, respectively, immediately after the inversion pulse. The effect of the spin-lattice relaxation is neglected since $\tau \ll T_1$, making $S^o_{RBC} + S^o_{p1}$ a constant during the exchange process.

Figure 5B:
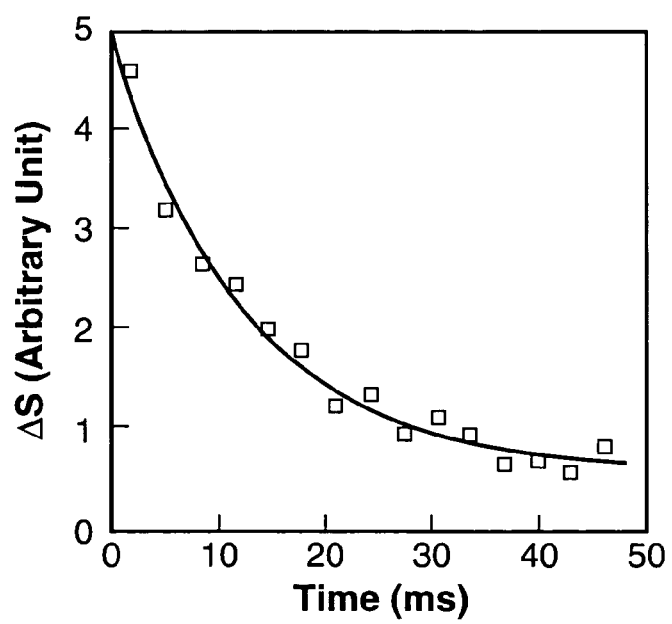

The time dependence of the difference of the two signals, $\Delta S = S^o_{RBC} - S^o_p$, is shown in FIG. 5B. From an exponential fit, it was determined that $\tau = 12.0 \pm 1$ ms. The reduction of the signals due to the finite tipping angle was taken into account. Given the constraint on $\tau_{p1}/\tau_{RBC}$ from the ratio of the signals at equilibrium, $\tau_{RBC} = 20.4 \pm 2$ ms, $\tau_{p1} = 29.1 \pm 2$ ms were obtained. The time scale for the diffusion of xenon ($\tau_{RBC} = 20.4$ ms) corresponded to the time for the diffusion of xenon over a distance of 11 µm (a diffusion constant of $10^{-5}$ cm$^2$/s was assumed). This distance is slightly larger than the characteristic dimension of the RBC. The xenon $\tau_{RBC}$ was found to be longer than that for water molecules, which was determined to be $12 \pm 2$ ms at room temperature, Herbst, M. D., et al., *Am. J. Physiol.*, 256: C1097-C1104 (1989).

The above example demonstrates that data relevant to the dynamics of the interaction between laser polarized xenon and its environment (e.g., a mixture of red blood cells and plasma) are accessible using NMR spectroscopy.

Example 5

This example illustrates the preparation and NMR properties of a vehicle for xenon delivery which consists of a mixture of xenon and an aqueous suspension of lipid vesicles. An efficient method is provided for delivery of optically polarized xenon to the vascular system in order to observe the xenon-129 NMR signal before the xenon polarization has decayed. Specifically, the hyperpolarized gas is pre-dissolved in solutions where the xenon has a long spin-lattice relaxation time and, thereafter, the xenon/solution mixture is administered to the blood.

5.1 Materials and Methods

A solution of hyperpolarized xenon in INTRALIPID® was prepared in the same manner as described for the saline solution of hyperpolarized xenon, however, the shaker was charged with INTRALIPID® rather than saline. INTRALIPID® solutions consist of aqueous suspensions of lipid vesicles of approximately 0.1 µm in diameter, which are well tolerated in vivo and are used clinically as nutrient supplements. Commercially available 20% INTRALIPID® solution (Pharmacia, Uppsala, Sweden) is approved by the U.S. Food and Drug Administration for use in humans. Importantly, xenon has an approximately 4-fold greater solubility in INTRALIPID® than in saline. The INTRALIPID® solution was charged with laser polarized $^{129}$Xe and an aliquot (1 mL) of this solution was added to human blood (1 mL). The spectra were obtained on a Bruker AM-400 spectrometer. The 128×64 image was obtained by the Echo Planar Imaging method on a Quest 4300 (Nalorac Cryogenics, Martinez, Calif., U.S.A.) spectrometer.

5.2 Results

Figure 6:
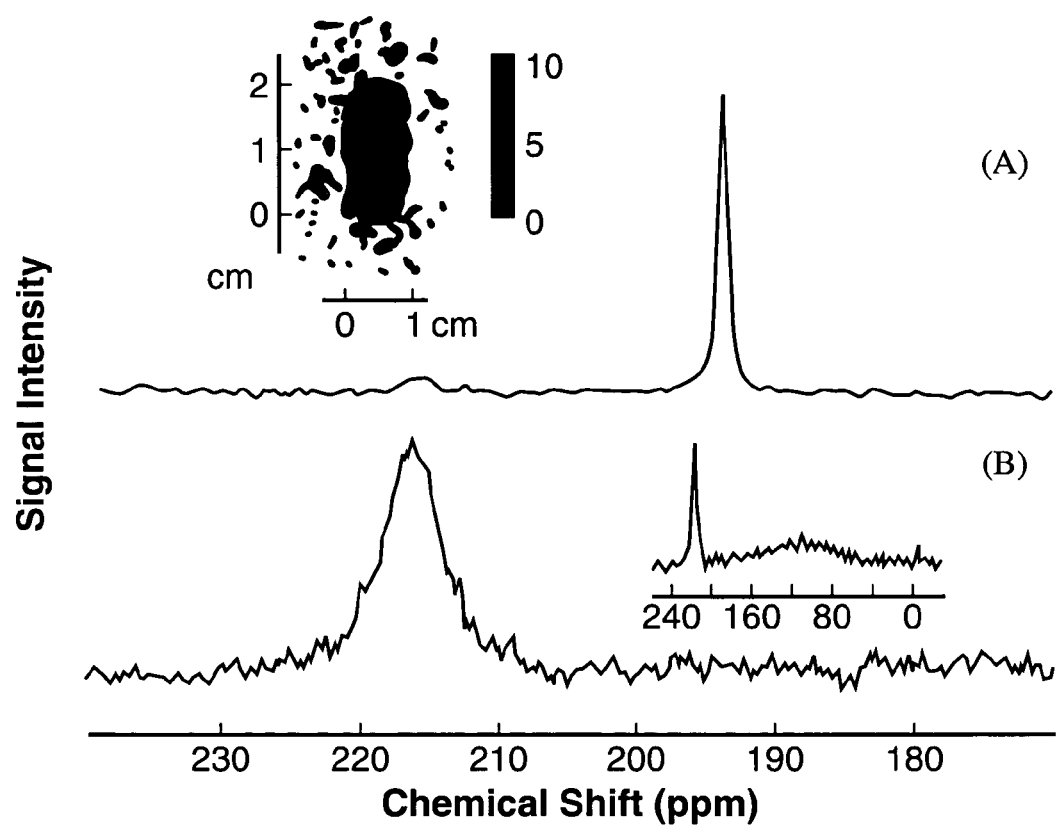
FIGS. 6A and 6B. Optically pumped $^{129}$Xe spectrum of xenon delivered to blood in the INTRALIPID® solution is provided (A). 2-dimensional $^{129}$Xe MR image laser-polarized xenon in blood/INTRALIPID® (A, inset). A $^{129}$Xe spectrum acquired after mixing the xenon/FLUOSOL® solution in whole blood (B). Compressed $^{129}$Xe NMR spectrum of xenon/FLUOSOL® solution in whole blood (B, inset).

The xenon $T_1$ in the INTRALIPID® solution was measured to be 40±3 s. The spectrum of the laser polarized xenon, delivered to blood as an Intralipid solution, is shown in FIG. 6A. The predominant feature of the spectrum is a peak at 194 ppm, which corresponds to the xenon in the pure Intralipid solution. Only a small signal is observed at 216 ppm; the signal corresponding to xenon in the RBC (i.e., intracellular). The ratio of the peak corresponding to xenon in the INTRALIPID® solution and the peak from the intracellular xenon is approximately 6:1. This result is consistent with a higher affinity of the xenon for the lipids and a correspondingly inefficient transfer into the RBC. The $T_1$ decay time of the signal at 194 ppm was measured to be 16 s, a factor approximately 3-fold larger than the corresponding decay time for xenon in the saline water/blood mixture. The $^{129}$Xe signal was so strong in this sample as to allow the direct imaging of the xenon distribution in the mixture. The acquired image is displayed in FIG. 6A (inset).

Xenon in blood can be utilized to study lung air-space anatomy, tissue perfusion and NMR angiography. In general, hyperpolarized xenon NMR would be an alternative to the imaging techniques that make use of radioactive isotopes of xenon, such as $^{127}$Xe and $^{133}$Xe. The advantages of MRI of hyperpolarized xenon are the zero ionizing radiation dose absorption by the patient and a potentially much better spatial resolution. NMR of xenon may also prove useful for brain studies. Specifically, magnetic resonance imaging of hyperpolarized xenon would enable better detection of central nervous system perfusion and thus be a tool for diagnosis of stroke and also a flow specific tool for functional imaging.

This example demonstrates the preparation and the properties of solutions of hyperpolarized xenon in lipids. Also demonstrated is the principle that lipid solutions of laser polarized xenon can be used to deliver polarized xenon through the blood. The presence of the lipid in the delivery vehicle both retards penetration of the xenon through the RBC membrane and protects the xenon polarization from rapidly decaying.

The use of different solutions for administering hyperpolarized xenon to blood and tissues is very promising for $^{129}$Xe Spectroscopic Imaging, Chemical Shift Imaging or in vivo Localized NMR Spectroscopy in tissues. $^{129}$Xe NMR parameters, such as the relaxation times, may prove useful to probe the state of health of tissues or the malignancy of tumors. Moreover, xenon dissolves readily in fat, and hyperpolarized xenon MRI may be an alternative to conventional proton MRI of fatty tissues.

Example 6

Example 6 demonstrates the utility of perfluorocarbons as delivery vehicles for laser polarized xenon.

Perfluorocarbon compounds are generally chemically inert and non-toxic. Interestingly, perfluorocarbon emulsions are able to absorb and transport oxygen and carbon dioxide. A representative perfluorocarbon emulsion, FLUOSOL® (Green Cross, Osaka, Japan), was chosen as a promising prototypical delivery vehicle for xenon. FLUOSOL® is an emulsion which contains 20% perfluorocarbon and is approved by the U.S. F.D.A. for intravascular administration in humans as a blood substitute.

A solution of hyperpolarized xenon in FLUOSOL® was prepared in the same manner as described for the saline solution of hyperpolarized xenon, however, the shaker was charged with FLUOSOL® rather than saline. The FLUOSOL® solution was charged with laser polarized $^{129}$Xe and an aliquot (1 mL) of this solution was added to human blood (1 mL). The spectra were obtained on a Bruker AM-400 spectrometer.

6.2 Results

FIG. 6B shows a $^{129}$Xe NMR spectrum acquired after mixing the FLUOSOL®/xenon solution with blood. The peak at 216 ppm corresponds to xenon in the RBC, whereas the broad peak centered around 110 ppm (FIG. 6B, inset) arises from xenon in the FLUOSOL® solution. Xenon in pure FLUOSOL® has a chemical shift of 110 ppm and the peak exhibits a broadening which is similar to that observed in the spectrum of the xenon/blood/FLUOSOL® solution. The ratio of the integrated intensities of the broad and narrow peaks is approximately 3. The $T_1$ of the narrow peak was measured to be 13±1 s. This $T_1$ is, similar to that measured for xenon in INTRALIPID®; longer than that measured for xenon in the RBC/plasma sample. The results with FLUOSOL® suggest that xenon exchanges between the interior of the RBC and an environment characterized by a xenon relaxation time which is longer than that exhibited by intracellular xenon. Presumably, the xenon which has the longer relaxation time resides in the FLUOSOL®. These results have implications for the selective MRI/NMR of xenon which has been transferred to tissues.

Figure 7:
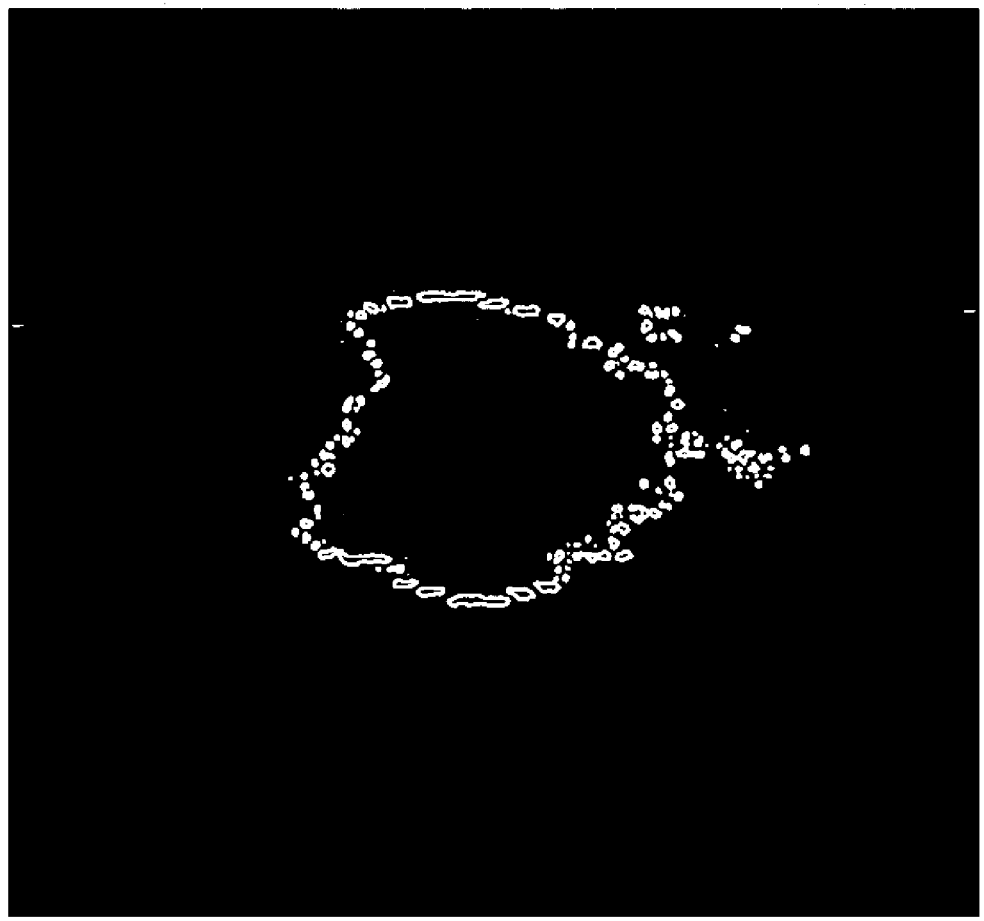
FIG. 7. Two-dimensional magnetic resonance image of $^{129}$Xe dissolved in fresh human blood taken immediately after the blood is mixed with the saline saturated by hyperpolarized xenon. The 128×64 images were taken by the Echo Planar Imaging (EPI) method on a Quest 4300 spectrometer. The diameter of the sample tube is 10 mm, and the solution occupies a region of length of 20 mm.

Also acquired was a two-dimensional MR image of $^{129}$Xe dissolved in fresh human blood (FIG. 7). The image was acquired immediately after the blood was mixed with a saline solution saturated with hyperpolarized $^{129}$Xe.

The above example illustrates that perfluorocarbon emulsions are useful delivery vehicles for hyperpolarized noble gases. Also demonstrated is the feasibility of acquiring an MR image of $^{129}$Xe dissolved in blood when the $^{129}$Xe is administered to the blood as a saline solution and, therefore, has a shorter T, than is observed for 129Xe in a fluorocarbon delivery agent.

Example 7

7.1 Materials and Methods

Solutions of hyperpolarized $^{129}$Xe in partially deuterated benzene (25% $C_6D_5H$, 75% $C_6D_6$) were prepared as described above for saline solutions of $^{129}$Xe with the exception that the shaker was charged with the benzene solution rather than saline. Typically, $4\times10^{-4}$ mol of enriched $^{129}$Xe (80%, EG&G Mound) were used in one experiment at a pressure of 1 atm. $^{129}$Xe NMR was performed at 51 MHz on a Quest 4300 spectrometer (Nalorac Cryogenics, Martinez, Calif., U.S.A.) with a home built probe and a tipping angle of 3°. $^1$H NMR was performed at 185 MHz with a home built probe and a tipping angle of 3°.

Time-resolved two-dimensional MR images of $^{129}$Xe were obtained using the fast low-angle shot (FLASH) imaging method on the Quest 4300 instrument using a tipping angle of 3° for each of the 64 signal acquisitions. The frequency-encoding gradient was 3.5 G/mm. The step size of the phase-encoding gradient pulses, which were 500 µs long, was 0.063 G/mm. The diameter of the sample tube was 7 mm and the solution occupied a region within the tube of length 15 mm. The images were 64×128 pixel images.

The time-resolved distribution (in seconds) of an unshaken sample of partially deuterated benzene was obtained from MRI projections along the tube axis (z). The imaging field gradient for the acquisition of these images was 2.6 G/mm.

Two-dimensional MR images of the SPINOE-enhanced $^1$H signals were obtained at 2 and 6 minutes after hyperpolarized $^{129}$Xe was admitted to the sample tube containing normal benzene. The images were taken by the echo planar imaging method in 24 ms. The frequency encoding gradient was 3.15 G/mm; the phase-encoding gradient pulses were 0.14 G/mm and 50 µs long. The image dimension was 128×32 pixels, and the image was zero-filled to 256×256 pixels in data processing.

The methods used and the results obtained in this example are discussed in detail in Navon, G., et al., *Science,* 271: 1848-1851 (1996), which is herein incorporated by reference.

7.2 Results

In the following example, the preliminary experiments designed to probe the SPINOE between hyperpolarized xenon and protons in solution are described. When hyperpolarized $^{129}$Xe is dissolved in liquids, a time-dependent departure of the proton spin from its thermal equilibrium was observed. The variation in magnetization was an unexpected manifestation of the nuclear Overhauser effect (NOE), a consequence of cross-relaxation between the spins of solution protons and $^{129}$Xe. SPINOE has been used to monitor time dependent magnetic resonance images and high resolution NMR spectra of solution spins as they encounter the migrating xenon atoms.

Figure 8:
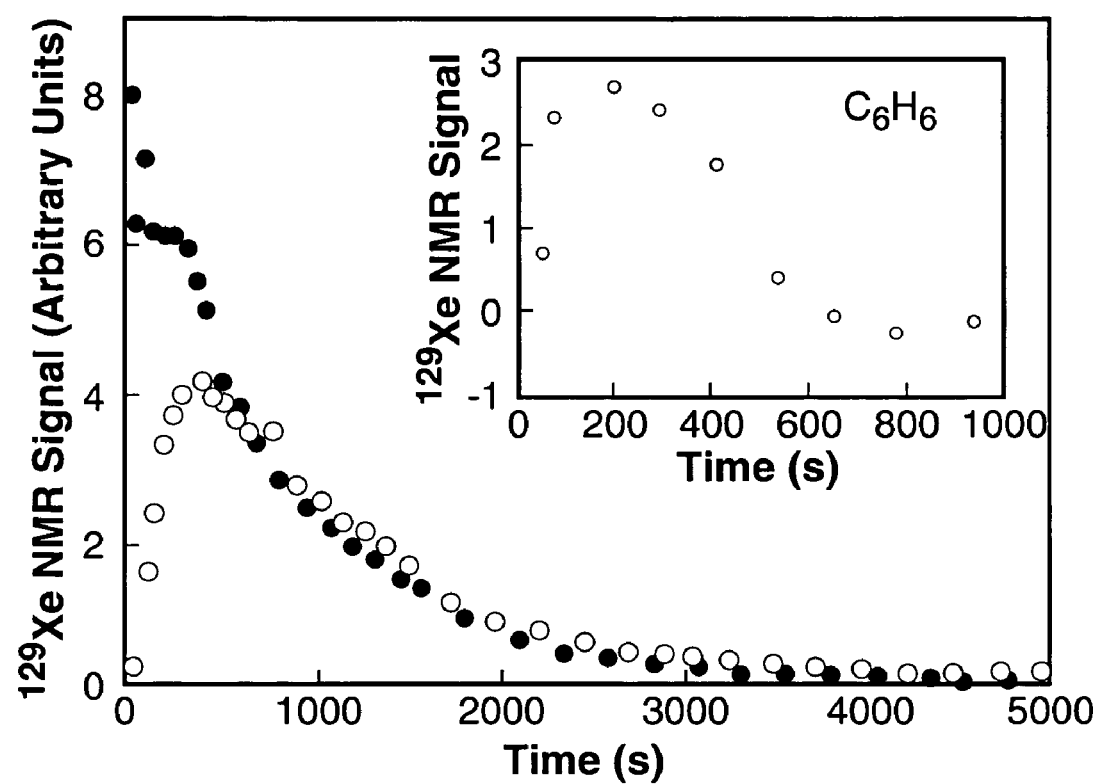
FIG. 8. Time dependence of the hyperpolarized $^{129}$Xe NMR signal observed in benzene solution after being contacted with hyperpolarized xenon. The main figure shows the data for partially deuterated benzene (25% $C_6D_5H$, 75% $C_6D_6$); the inset shows the data for normal benzene ($C_6H_6$). In the experiments represented by open circles, xenon was admitted into benzene by opening the xenon reservoir; the initial rise in signal represents the penetration of xenon into the solvent. In the experiment represented by closed circles, the xenon was mixed with the benzene by shaking the sample after opening the xenon reservoir, so as to produce a uniform saturated solution. $^{129}$Xe spin polarization was enhanced by optical pumping using circularly polarized light at 794.7 nm. Typically, $4\times10^{-4}$ moles of enriched $^{129}$Xe were used in one experiment. The difference in the $^{129}$Xe signal between benzene and deuterated benzene demonstrates the effect of magnetic dipolar coupling between $^1$H and $^{129}$Xe spins on the relaxation of the $^{129}$Xe. For the initial NOE experiments, the partially deuterated liquids were used in order to favor the effects of cross-relaxation over those contributing to $^1$H auto-relaxation. $^{129}$Xe NMR was performed at 51 MHz on a Quest 4300 spectrometer using a home-built probe and a tipping angle of 3°.

The time dependence of the $^{129}$Xe NMR signal intensity observed when hyperpolarized $^{129}$Xe is dissolved in liquid benzene is shown in FIG. 8. The observed spin-lattice relaxation time of $^{129}$Xe in solution, a combination of the gas and solution relaxation times, is ~200 s in normal benzene and ~1000 s in the partially deuterated sample (Moschos, A, et al., *J. Magn. Reson.* 95: 603 (1991); and Diehl, P., et al., *J. Magn. Reson.* 88: 660 (1990). The difference between these two values demonstrates the effect of magnetic dipolar coupling between $^1$H and $^{129}$Xe spins on the relaxation of the $^{129}$Xe magnetization; the same coupling underlies the cross relaxation between the xenon and proton spin systems. For the initial NOE experiments, the partially deuterated liquids were used to promote the effects of cross relaxation over the potentially limiting auto-relaxation of the proton spins.

Figure 9:
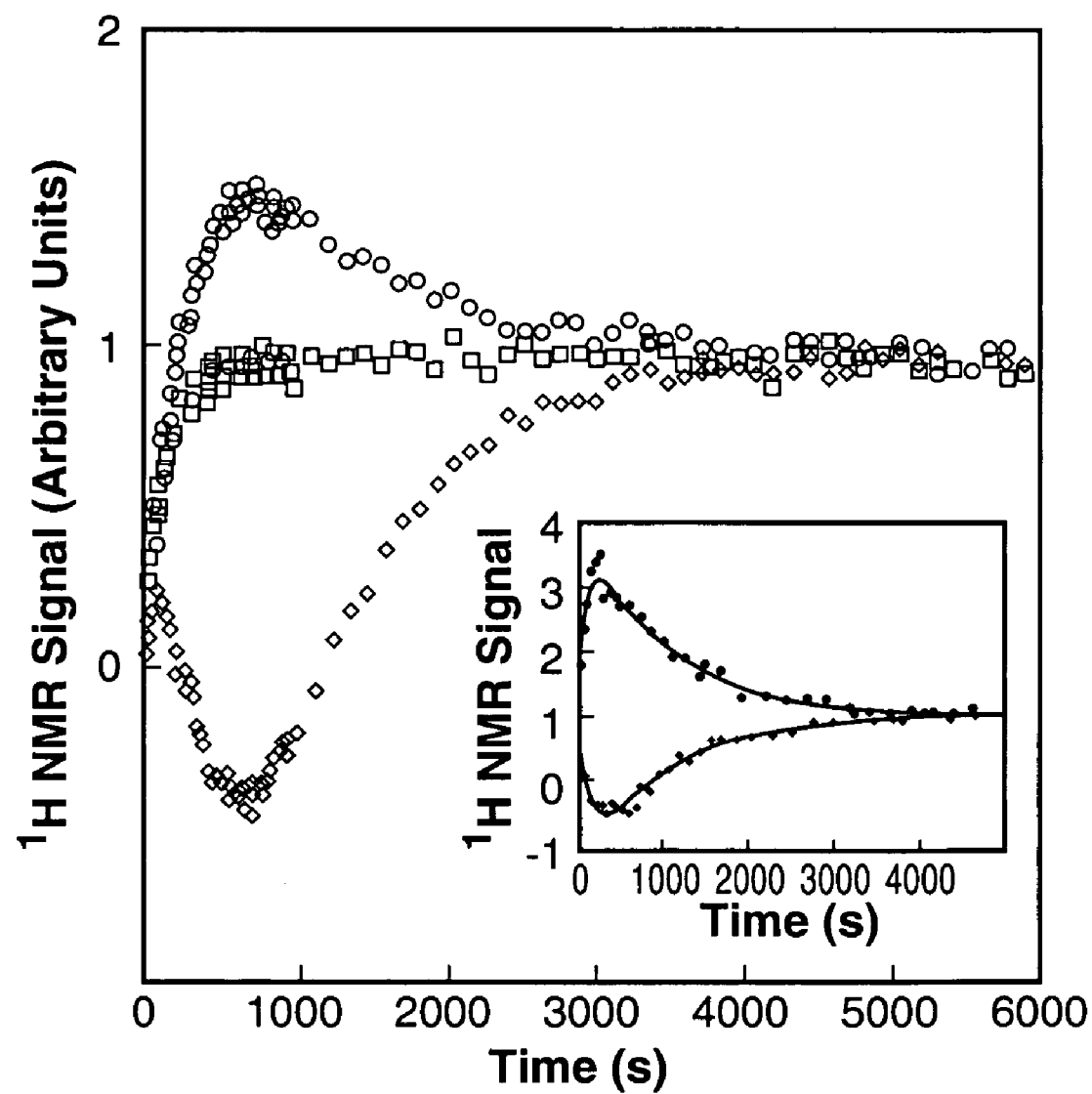
FIG. 9. Time dependence of the $^1$H NMR signal observed after exposure of partially deuterated benzene (25% $C_6D_5H$, 75% $C_6D_6$) to hyperpolarized $^{129}$Xe. The sample was exposed to xenon at zero magnetic field and was then inserted into the NMR probe within a few seconds. The initial rise of the $^1$H signal is due to spin-lattice relaxation. The $^1$H NMR signal exhibits a positive (○) or negative (◊) NOE depending on the sign of the $^{129}$Xe polarization. From the variation of the $^1$H signal in the presence of unpolarized xenon (□), the $^1$H $T_1$ of the benzene-xenon solution is determined to be ~160 s. Inset: Time dependence of the $^1$H NMR signal after polarized $^{129}$Xe was dissolved in partially deuterated benzene. Prior to admitting the xenon, the sample was placed in the NMR magnet for approximately 10 minutes to allow thermal equilibration of the $^1$H magnetization. After the xenon reservoir was opened, the sample was then shaken to ensure efficient mixing of the xenon and benzene. The smooth lines represent a fit to the time dependent solution (J. H. Noggle, R. E. Schirmer, *The Nuclear Overhauser Effect: Chemical Applications* (Academic Press, New York-London-Toronto-Sidney-San Francisco, 1971)) of Eq. 1.

The effect of the dissolved hyperpolarized $^{129}$Xe on the $^1$H magnetization in liquid benzene is illustrated in FIG. 9. The proton NMR signal exhibits a positive or negative time-dependent NOE, depending on the sign of the $^{129}$Xe magnetization, which is determined by the helicity of the laser light or the orientation of the magnetic field in the optical pumping stage. The fractional enhancement of the proton magnetization over its thermal equilibrium value is typically ~0.1 for benzene, and between 0.5 and 2 for the partially deuterated sample.

Based on the theory of the nuclear Overhauser effect, the following expression can be derived for the maximum change in the polarization of the solvent nuclei (I) due to cross relaxation with the dissolved gas (S):

$$\frac{I_z(t_0) - I_0}{I_0} = -\frac{\sigma_{IS}}{\rho_I} \frac{\gamma_S S(S+1)}{\gamma_I I(I+1)} \frac{[S_z(t_0) - S_0]}{S_0} \qquad (6)$$

where $\gamma_S$ and $\gamma_I$ are the magnetogyric ratios of the nuclear spins, $\sigma_{IS}$ the cross-relaxation rate, and $\rho_I$ is the auto-relaxation rate of the I spins. The cross-relaxation rate $\sigma_{IS}$ has the same value, $\sigma_{IS}$=1.9×10$^{-6}$ s$^{-1}$, for both benzene and partially deuterated benzene solutions, so the difference in the maximum enhancement of the proton polarization in these two solutions originates from the different proton relaxation rates, $\rho_1$=(20 s)$^{-1}$ in benzene and $\rho_{I'}$=(160 s)$^{-1}$ in the partially deuterated solution. Given the spin quantum numbers and the magnetogyric ratios of the two nuclei, I=S=½, $\gamma_1$=2.67×10$^8$ rad T$^{-1}$ s$^{-1}$, and $\gamma_S$=−7.44×10$^7$ rad T$^{-1}$ s$^{-1}$, and the enhancement of the $^{129}$Xe polarization at the time $t_o$ when the proton magnetization reaches its maximum (minimum), $S_Z(t_o)/S_o$≈6000, the maximum proton enhancement is estimated to be 0.06 in $C_6H_6$ and 0.5 in the partially deuterated solution, in general agreement with the measured values.

The high spin-polarization and the slow relaxation of $^{129}$Xe in the solvent allow for a detailed observation of the dissolution process and the flow of xenon in the solvent by means of MRI. FIG. 10 shows two-dimensional MRI projections along the vertical axis of the sample tube. Xenon is found to accumulate first at the bottom of the tube, establishing a gradient in xenon concentration and continues to dissolve into the benzene as the solution gradually becomes saturated. A detail of this process is shown in FIG. 11, where a series of the one-dimensional image intensities along the tube axis reflects the time-dependent spatial distribution of the xenon. The descent of xenon in the sample tube occurs because of density differences between the solution and pure benzene. The heavier xenon-rich regions of the solution, which form at the top of the solution by diffusion of the xenon into the solvent, gravitate to the lower part of the tube by natural convection, ultimately filling the tube with saturated xenon solution.

Because of the SPINOE enhancement of the proton spins proximate to the dissolved hyperpolarized xenon, the xenon concentration gradient is expected to induce a gradient in the proton magnetization. Indeed, as shown in FIG. 12, the benzene proton magnetization images display a time dependent gradient consistent with the spatial distribution of xenon shown in FIGS. 10 and 11. In fact, differential SPINOE enhancements of proton NMR can be observed in solutions containing more than one component or in molecules possessing nuclei with different chemical shifts, making it possible to explore the partitioning and selective association of the hyperpolarized gas.

The foregoing results indicate that it is possible to image not only the hyperpolarized xenon, but also the environment in which it is accommodated, a finding which has implications for both materials and medical applications, for xenon as well as for helium. Because the equilibrium polarization of the solution spins, $S_o$ is proportional to the magnetic field, $B_o$, the relative SPINOE is inversely proportional to $B_o$ and is thus expected to be more pronounced at the lower magnetic fields normally used in medical imaging. Furthermore, since the nuclear Overhauser effect depends on the proximity of the xenon nucleus and the neighboring spins, as well as their relative translational motion, a large SPINOE is anticipated in systems where the noble gas atoms are partially immobilized in materials, Miller, J. B., et al., *Macro-* molecules 26: 5602 (1993), or temporarily bound to molecules such as proteins, Tilton, R. F., et al., *Biochemistry* 21, 6850 (1982), even in the presence of relatively fast proton relaxation. The window is thus opened to other potential applications where xenon may be adsorbed in materials, on surfaces, or in biological molecules and organisms.

Example 8

This example illustrates the utility of $^{129}$Xe—$^{1}$H SPINOE spectroscopy for studying the dynamical and structural characteristics of molecules in solution. That the coupling between laser-polarized $^{129}$Xe and protons in a p-nitrotoluene solution is due to nuclear spin dipolar coupling modulated by diffusive motion is demonstrated.

8.1 Materials and Methods

The samples were generally prepared as described in the examples above. The pulse sequence used to obtain SPINOE data is a heteronuclear version of the difference NOE pulse sequence originally suggested by Stonehound, J., et. al. *J. Am. Chem. Soc.* 116: 6037 (1994) for homonuclear NOE studies. One method for observing SPINOEs is simply to acquire the proton signal as a function of time after laser-polarized $^{129}$Xe is introduced to the solution. The deviation of the proton signal from its thermal equilibrium value determines the signal due to SPINOE from laser-polarized$^{129}$Xe. However, this method relies on a subtraction of two large signals (with and without SPINOE), and this subtraction limits the sensitivity of the experiment to only those SPINOE signals greater than about one percent of the equilibrium signal. This new sequence is advantageous compared to the conventional SPINOE method since the equilibrium signal can be suppressed by two orders of magnitude or more. This type of sequence has enabled measurements of NOEs less than $10^{-4}$ of the equilibrium signal.

The difference SPINOE sequence is shown in FIG. 13. The saturation of proton resonances is first achieved by applying a train of proton $\pi/2$ pulses, and this saturation is maintained with the proton $\pi$ pulses during the mixing time when the SPINOE occurs. The timing of the $\pi$ pulses is adjusted to give optimal saturation. A $\pi$ pulse is also applied to the $^{129}$Xe resonance at the same time of the proton $\pi$ pulse so that the proton signal due to SPINOE will be accumulated over the entire mixing time. Odd numbers of such $\pi$ pulse pairs were used so that each acquisition inverted the $^{129}$Xe magnetization; thus the subtraction of two consecutive signals effectively removed all contributions to the signal that did not originate from SPINOE.

8.2 Results

Polarization transfer from laser-polarized xenon to p-nitrotoluene in a solution of perdeuterated benzene was observed. p-nitrotoluene is a simple molecule that does not show binding of xenon in solution; thus we anticipated that its couplings of its protons to xenon would be similar to that of benzene protons. The difference SPINOE proton spectra with laser-polarized $^{129}$Xe are shown in FIG. 14A and FIG. 14B. The $^{129}$Xe polarization is negative in FIG. 14A and positive in FIG. 14B and the magnetization transfer to proton is found to be negative and positive, respectively. This observation is consistent with a correlation time that is much shorter than the inverse of the Larmor frequencies of $^{1}$H and $^{129}$Xe, in which case the cross-relaxation constant $\sigma_{IS}$ would be positive. From the initial rise of the proton SPINOE signal intensity, we obtain the values of $\sigma_{IS}$ for the aromatic and methyl protons to be similar to that for benzene protons and the theoretical estimate of the cross-relaxation rate due to dipolar coupling modulated by molecular diffusion.

The above example demonstrates the utility of $^{129}$Xe—$^{1}$H SPINOE spectroscopy for studying the dynamical and structural characteristics of molecules in solution. That the coupling between laser-polarized $^{129}$Xe and protons in a p-nitrotoluene solution is due to nuclear spin dipolar coupling modulated by diffusive motion is demonstrated. Further, it has been shown that the sign of the SPINOE signal is influenced by the sign of the $^{129}$Xe polarization.

Example 9

This example demonstrates the effect of $^{129}$Xe binding to a molecule in solution on the observed SPINOE signal(s) arising from that molecule. A cyclic polysaccharide, cyclodextrin, was chosen as a model compound.

9.1 Materials and Methods

Hyperpolarized xenon and mixtures of hyperpolarized xenon and cyclodextrins were prepared generally as discussed above. SPINOE signals of 0.05 M cyclodextrin solutions in deuterated DMSO were measured as described above in Example 8.

9.2 Results

α-Cyclodextrin is a naturally occurring host molecule composed of six D-glucose units linked head to tail in a 1α, 4-relationship to form a ring known as a cyclohexaamylose. It has a relatively inflexible doughnut shaped structure where the top of the molecule has twelve hydroxyl groups from positions 2 and 3 of the glucose units and the bottom has the 6 primary hydroxyl groups from position 6. The equilibrium proton spectrum of α-cyclodextrin in deuterated DMSO is displayed in FIG. 15. Cyclodextrins are cyclic glucopyranose oligomers that possess a hydrophobic binding pocket, Saenger, W., *Angew. Chem. Int. Ed.* 19: 344 (1980). The hydrophobic binding properties of cyclodextrins permit them to complex a number of different guest species, from drugs to noble gases, Szejtli, J., CYCLODEXTRIN TECHNOLOGY, Kluwer-Academic, Dordrecht, 1988. Specifically, it has been shown in NMR studies that α-cyclodextrin complexes xenon, Bartik, K., et al., *J. Magn. Res. B*, 109: 164 (1995).

The first evidence of strong couplings between xenon and α-cyclodextrin is the reduced $^{129}$Xe T$_1$ in the solution of α-cyclodextrin. For example, the measured $^{129}$Xe T$_1$ was 20 s in 0.1 M α-cyclodextrin solution in deuterated DMSO, compared to a T$_1$>500 s in 0.1 M p-nitrotoluene in deuterated benzene. This increase in the apparent relaxation rate of xenon is due to the dipolar coupling between xenon and the protons of α-cyclodextrin; this coupling not only determines the cross-relaxation of the two spins, but also contributes to the xenon auto-relaxation.

In order to study the effects of xenon binding on $^{129}$Xe—$^{1}$H SPINOE, SPINOEs from laser-polarized xenon to α-cyclodextrin dissolved in a solution of perdeuterated dimethyl sulfoxide (DMSO) were observed. The proton SPINOE spectra of α-cyclodextrin in the presence of $^{129}$Xe of negative polarization and of positive polarization are shown in FIG. 16 and FIG. 17, respectively. The assignment of the proton resonance has been reported in other work, Djedaini, F., et al., *J. Mol. Struct.,* 239: 161 (1990). In contrast to the SPINOE spectra of p-nitrotoluene, the SPINOE signal intensities for various protons of α-cyclodextrin are substantially different. The strongest SPINOEs are observed from H3 and H5, protons located on the inside of the cyclodextrin cavity. The SPINOE signals from the outer protons H2, H4, and H1, however, are about a factor of 6 smaller. This difference in the xenon coupling to various protons can be expected because such dipolar coupling is highly sensitive to the relative distance between spins. One can derive a ratio of the distances between xenon-H3,H5 and xenon-H1,H2,H4 to be $1/^6\sqrt{6}=1/1.35$.

The percentage SPINOE signal is significantly larger than that from p-nitrotoluene solution. Taking into account the xenon pressures in the sample cell and the magnetic fields applied in the different experiments of p-nitrotoluene and α-cyclodextrin, we estimate that the ratio of the cross-relaxation rates of α-cyclodextrin and p-nitrotoluene is approximately 100. This large increase in the overall coupling constant can be attributed to significant binding between xenon and α-cyclodextrin molecules. Although smaller, the SPINOE signals from the three hydroxyl protons are also observable.

Additionally, the xenon coupling constants have been compared for α-cyclodextrin and β-cyclodextrin, where β-cyclodextrin is a seven-unit cyclodextrin ring. Even though the size of β-cyclodextrin is merely 15% larger than α-cyclodextrin, its binding of xenon is dramatically reduced and the coupling constants are two orders of magnitude smaller, essentially equivalent to the coupling constants of p-nitrotoluene.

In the above example, it was demonstrated that the off-equilibrium polarization of xenon can be transferred to other nuclear species, such as protons. Thus, hyperpolarized xenon can be exploited as a contrast agent for protons. Moreover, it can be used to elucidate structures of biologically relevant molecules, such as proteins, by selective polarization transfer to the protons of the specific sites where the xenon binds.

Example 10

This example describes the in vivo use of hyperpolarized xenon dissolved into a lipid vehicle. Optically pumped xenon was dissolved into a lipid emulsion as described in Example 5 and injected intravenously into a rat. The $^{129}$Xe NMR spectra from the region of the heart and liver were recorded as a function of time.

10.1 Materials and Methods

The laser polarized xenon and the solution of laser polarized xenon in INTRALIPID® were prepared essentially as described in the preceding examples.

Male rats weighing 200-250 grams were anesthetized by intramuscular injection of ketamine/xylazine/acepromazine (30/3/0.6 mg/kg). Supplemental intramuscular doses were administered as needed to maintain anesthesia. A venous catheter was placed into a tail vein, and the receiver/transmitter surface coil was placed over the heart and liver (FIG. 18). Acquisitions began at start of the injection. Prior to each experiment the rat was placed in lateral recumbency into the magnet. At the conclusion of each experiment, the catheter was removed and the rat was returned to its cage to recover from anesthesia.

The $^{129}$Xe NMR spectra were obtained on a home-built NMR spectrometer interfaced with a Bruker 2.35 T magnet (xenon frequency: 27.68 MHz, bore diameter: 25 cm). The receiver-transmitter surface coil had a diameter of 3.5 cm. For the spectroscopy experiment, spectra were obtained every second (pulse angle: ≈20°).

10.2 Results

A series of xenon NMR spectra were taken from the beginning of the intravenous injection of the xenon/IN-TRALIPID® solution. A spectrum representing an average of the sixth through twelfth scans is shown in FIG. 19; the time-dependence of the integrated signal is shown in the inset. It was anticipated that the Intralipid would initially accumulate in the liver; it is likely that the initial rise in signal amplitude reflects this accumulation, while the subsequent decay is due to wash-out, xenon relaxation, and the application of rf pulses.

This example demonstrates the feasibility of using lipid solutions of hyperpolarized xenon to deliver the xenon via an intravenous administration route. Also illustrated is that in vivo spectra of the hyperpolarized xenon can be readily obtained.

Example 11

This example describes the use of $^{129}$Xe MR imaging to obtain images of the in vivo distribution of hyperpolarized xenon in the rat. The hyperpolarized xenon was administered intramuscularly as a saline solution.

11.1 Materials and Methods

The methods for preparing the hyperpolarized xenon and a saline solution of the hyperpolarized xenon have been described in previous examples. The rats, anesthesia and apparatus were as described in Example 10, above. For the imaging experiment, the catheter was placed in the muscle of the rats thigh and secured with tape. The surface coil was placed over the injection site on the rat's thigh. At the conclusion of the experiment, the catheter was removed and the rat was returned to the cage to recover from anesthesia.

Axial images were acquired perpendicular to the coil using the FLASH sequence shown in FIG. 20. In the imaging experiment, ten two-dimensional $^{129}$Xe MR images were taken at intervals of approximately 7 s (with the exception of an 18 s delay between images 5 and 6) from the beginning of the injection of the xenon/saline solution.

11.2 Results

Six of the images obtained are shown in FIG. 21, and depict the signal intensity of the optically pumped xenon in the upper part of the rat's hind leg. The central region of low xenon signal intensity likely corresponds to the rat's femur. From the six images, one may observe that the signal intensity rises quickly and reaches a maximum at the second image (b) (7 s after the start of the injection), and then decays in the following images. The initial rise in intensity is due to the accumulation of the xenon/saline solution from the injection, while the subsequent decay is due mostly to the application of the rf pulses (48 pulses of approximately 5 degrees tipping angle), although xenon relaxation and wash-out undoubtedly made additional contributions to this decay. The change in the pattern of the images suggests that part of the xenon/saline solution may have penetrated and diffused into the surrounding tissue over the duration of the experiment.

The major advantage of saline water as the xenon solvent is the long xenon $T_1$, which permits negligible loss of polarization over the injection time. However, the solubility of xenon in saline water is low with an Ostwald coefficient of only 0.0926 (the STP volume of xenon dissolved in 1 liter of liquid at 1 atm of gas pressure). Higher xenon concentrations can be obtained by using alternative xenon solvents (e.g. INTRALIPID® and FLUOSOL®). Furthermore, the xenon partitioning properties of such solvents in biological tissues allow particular in vivo applications. It was determined in previous in vitro studies that such solvents can bring about a three-fold increase in the effective relaxation time of xenon in blood. Thus, administration of the polarized xenon dissolved into one of these two classes of delivery vehicles is anticipated to improve the MR images acquired and to afford a longer temporal imaging window.

Example 11 demonstrates that in vivo $^{129}$Xe MR images can be obtained and used to study the distribution of hyperpolarized xenon in a living system.

It is to be understood that the above description and examples are intended to be illustrative and not restrictive. Many embodiments will be apparent to those of skill in the art upon reading the above description and examples. The scope of the invention should, therefore, be determined not with reference to the above description and examples, but should instead be determined with reference to the appended claims, along with the full scope of equivalents to which such claims are entitled. The disclosures of all articles and references, including patent applications and publications, are incorporated herein by reference for all purpose.

What is claimed is:

1. An apparatus for preparing a solution of a hyperpolarized noble gas in a fluid, comprising:
    a vessel for receiving the fluid;
    a reservoir for receiving the hyperpolarized noble gas, the reservoir communicating through a first shutoff valve with said vessel, said reservoir being separated in space from said vessel such that it can be cooled independently of said vessel;
    a gas inlet port communicating through a second shutoff valve with said reservoir;
    means for withdrawing said fluid from said vessel independently of said first shutoff valve and said second shutoff valve;
    a cryogenic bath of liquid gases for freezing said hyperpolarized noble gas; and
    a magnet selected from the group of magnets consisting essentially of a permanent magnet, an electromagnet, a superconducting electromagnet, and a shimmed NMR spectrometer for applying a magnetic field to said reservoir.

2. An apparatus as recited in claim 1, wherein said means for withdrawing said fluid from said vessel comprises:
    a reversible seal coupled to a port in said vessel; and
    a syringe configured to be removably inserted through said reversible seal.

3. An apparatus as recited in claim 2, wherein said reversible seal comprises a seal selected from the group of seals consisting essentially of a cap, a plug, a septa, a membrane, and a break seal.

4. An apparatus as recited in claim 1, wherein said means for withdrawing said fluid from said vessel comprises:
    a fluid flow regulator coupled to a port in said vessel; and
    a tubular member associated with said fluid flow regulator.

5. An apparatus as recited in claim 4, wherein said fluid flow regulator comprises a valve selected from the group of valves consisting essentially of a stopcock, a check valve, a ball valve, and a pressure release valve.

6. An apparatus for preparing a solution of a hyperpolarized noble gas in a fluid, comprising:
    a vessel for receiving the fluid;
    a reservoir for receiving the hyperpolarized noble gas, the reservoir communicating through a first shutoff valve with said vessel, said reservoir being separated in space from said vessel such that it can be cooled independently of said vessel;
    a gas inlet port communicating through a second shutoff valve with said reservoir;
    means for withdrawing said fluid from said vessel independently of said first shutoff valve and said second shutoff valve, wherein said means for withdrawing comprises a reversible seal coupled to a port in said vessel;
    means for freezing said hyperpolarized noble gas;
    means for applying a magnetic field to said reservoir.

7. An apparatus as recited in claim 6, wherein said means for withdrawing said fluid from said vessel comprises:
    a syringe configured to be removably inserted through said reversible seal.

8. An apparatus as recited in claim 6, wherein said reversible seal comprises a seal selected from the group of seals consisting essentially of a cap, a plug, a septa, a membrane, and a break seal.

9. An apparatus as recited in claim 6, wherein said means for freezing said hyperpolarized noble gas comprises a cryogenic bath of liquid gases.

10. An apparatus as recited in claim 6, wherein said means for freezing said hyperpolarized noble gas comprises a refrigeration unit.

11. An apparatus as recited in claim 6, wherein said means for applying a magnetic field to said reservoir comprises a magnet selected from the group of magnets consisting essentially of a permanent magnet, an electromagnet, a superconducting electromagnet, and a shimmed NMR spectrometer.

12. An apparatus for preparing a solution of a hyperpolarized noble gas in a fluid, comprising:
    a vessel for receiving the fluid;
    a reservoir for receiving the hyperpolarized noble gas, the reservoir communicating through a first shutoff valve with said vessel, said reservoir being separated in space from said vessel such that it can be cooled independently of said vessel;
    a gas inlet port communicating through a second shutoff valve with said reservoir;
    means for withdrawing said fluid from said vessel independently of said first shutoff valve and said second shutoff valve, wherein said means for withdrawing comprises a fluid flow regulator coupled a port in said vessel;
    means for freezing said hyperpolarized noble gas; and
    means for applying a magnetic field to said reservoir.

13. An apparatus as recited in claim 12, wherein said means for withdrawing said fluid from said vessel comprises:
    a tubular member associated with said fluid flow regulator.

14. An apparatus as recited in claim 13, wherein said fluid flow regulator comprises a valve selected from the group of valves consisting essentially of a stopcock, a check valve, a ball valve, and a pressure release valve.

15. An apparatus as recited in claim 12, wherein said means for applying a magnetic field to said reservoir comprises a magnet selected from the group of magnets consisting essentially of a permanent magnet, an electromagnet, a superconducting electromagnet, and a shimmed NMR spectrometer.

16. An apparatus as recited in claim 12, wherein said means for freezing said hyperpolarized noble gas comprises a cryogenic bath of liquid gases.

17. An apparatus as recited in claim 12, wherein said means for freezing said hyperpolarized noble gas comprises a refrigeration unit.

18. An apparatus for preparing a solution of a hyperpolarized noble gas in a fluid, said apparatus comprising:

a vessel for receiving the fluid;

a reservoir for receiving the hyperpolarized noble gas, the reservoir communicating through a first shutoff valve with said vessel, said reservoir being separated in space from said vessel such that it can be cooled independently of said vessel;

a gas inlet port communicating through a second shutoff valve with said reservoir;

means for withdrawing said fluid from said vessel independently of said first shutoff valve and said second shutoff valve;

means for freezing said hyperpolarized noble gas; and means for applying a magnetic field to said reservoir.

19. An apparatus as recited in claim 18, wherein said means for withdrawing said fluid from said vessel comprises:

a reversible seal coupled to a port in said vessel; and a syringe configured to be removably inserted through said reversible seal.

20. An apparatus as recited in claim 19, wherein said reversible seal is a seal selected from the group of seals consisting essentially of a cap, a plug, a septa, a membrane, and a break seal.

21. An apparatus as recited in claim 19, wherein said means for withdrawing said fluid from said vessel comprises:

a fluid flow regulator coupled a port in said vessel; and a tubular member associated with said fluid flow regulator.

22. An apparatus as recited in claim 21, wherein said fluid flow regulator of said vessel comprises a valve selected from the group of valves consisting essentially of a stopcock, a check valve, a ball valve, and a pressure release valve.

23. An apparatus as recited in claim 18, wherein said means for freezing said hyperpolarized noble gas comprises a cryogenic bath of liquid gases.

24. An apparatus as recited in claim 18, wherein said means for freezing said hyperpolarized noble gas comprises a refrigeration unit.

25. An apparatus as recited in claim 18, wherein said means for applying a magnetic field to said reservoir comprises a magnet selected from the group of magnets consisting essentially of a permanent magnet, an electromagnet, a superconducting electromagnet, and a shimmed NMR spectrometer.

* * * * *

UNITED STATES PATENT AND TRADEMARK OFFICE
CERTIFICATE OF CORRECTION

PATENT NO. : 7,385,395 B2
APPLICATION NO. : 10/940297
DATED : June 10, 2008
INVENTOR(S) : Pines et al.

It is certified that error appears in the above-identified patent and that said Letters Patent is hereby corrected as shown below:

In the list of references, on page 3, column 1, line 47, please delete "Pluses" and insert -- Pulses --, therefore.

In the drawings, in Figure 13, please delete "1H" and insert -- $^1$H --, therefore.

In the specification, at column 2, line 47, please delete "tem" and insert -- temperature --, therefore.

At column 2, line 58, please delete "Effect" and insert -- Effect, --, therefore.

At column 3, line 19, please delete "hyperpolarize" and insert -- hyperpolarized --, therefore.

At column 5, line 12, after "$D_2O$" insert -- . --.

At column 5, line 62, please delete "C$_6$D5H," and insert -- $C_6D_5H$, --, therefore.

At column 7, line 42 (Approx.), please delete "equlibrium" and insert -- equilibrium --, therefore.

At column 7, line 45 (Approx.), please delete "129Xe" and insert -- $^{129}$Xe --, therefore.

At column 8, line 57, after "field" insert -- . --.

At column 9, line 18, please delete "bufffer" and insert -- buffer --, therefore.

At column 10, line 53, please delete "th" and insert -- that --, therefore.

At column 10, line 59, please delete "tat" and insert -- that --, therefore.

At column 13, line 46, please delete "thereof" and insert -- thereof. --, therefore.

At column 15, line 24, please delete "relaxtion" and insert -- relaxation --, therefore.

At column 15, line 38, please delete "aspect" and insert -- aspect, --, therefore.

UNITED STATES PATENT AND TRADEMARK OFFICE
CERTIFICATE OF CORRECTION

PATENT NO.      : 7,385,395 B2
APPLICATION NO. : 10/940297
DATED           : June 10, 2008
INVENTOR(S)     : Pines et al.

It is certified that error appears in the above-identified patent and that said Letters Patent is hereby corrected as shown below:

At column 17, line 17, please delete "methods:" and insert -- methods --, therefore.

At column 17, line 21, please delete "hyperpolarized" and insert -- hyperpolarzie --, therefore.

At column 17, line 49, please delete "min." and insert -- min --, therefore.

At column 18, line 14, please delete "modem" and insert -- modern --, therefore.

At column 19, line 61, please delete "tempera" and insert -- temperatures --, therefore.

At column 20, lines 15-38, below "manner.", please delete the repeated paragraph:

"EXAMPLES
Materials and Methods
The following general materials and methods were used in the examples described below.
The design of the shaker used in the dissolution stage for xenon mixing and delivery is illustrated in FIG. 1. The shaker has a small sidearm which can be isolated from the main volume by a stopcock The shaker is charged with a sample of either normal abundance or isotopically enriched xenon (80% .sup.129Xe, EG&G Mound, Miamisburg, Ohio, U.S.A.). Laser polarization is performed prior to admitting the xenon to the shaker. Briefly, approximately 5.times.1O.sup.-4 mol of 80% isotopically enriched .sup.129Xe was optically pumped in a 30 cc cylindrical glass pumping cell (diameter.apprxeq.30 mm). Before optical pumping, the cell was cleaned and coated with SURFASIL.RTM. (Pierce Chemical Co., Florence, Mass., U.S.A.); the cell was then evacuated to 10.sup.-6 torr and loaded with one drop of melted rubidium metal in a dry nitrogen environment. Optical pumping was performed with a 1.3 W continuous-wave Ti:sapphire laser (794.7 nm) for 20-30 min, and"

At column 20, line 53, please delete "80. %" and insert -- 80% --, therefore.

At column 24, line 26, please delete "$S^\circ_p$" and insert -- $S^\circ_{p1}$ --, therefore.

At column 26, line 44 (Approx.), please delete "T" and insert -- $T_1$ --, therefore.

UNITED STATES PATENT AND TRADEMARK OFFICE
CERTIFICATE OF CORRECTION

PATENT NO. : 7,385,395 B2
APPLICATION NO. : 10/940297
DATED : June 10, 2008
INVENTOR(S) : Pines et al.

It is certified that error appears in the above-identified patent and that said Letters Patent is hereby corrected as shown below:

At column 26, line 44, please delete "129Xe" and insert -- $^{129}$Xe --, therefore.

At column 27, line 43, please delete "(1991);" and insert -- (1991)); --, therefore.

At column 28, line 14, please delete "$\rho_1$" and insert -- $\rho_I$ --, therefore.

At column 28, line 17, please delete "$\gamma_1$" and insert -- $\gamma_I$ --, therefore.

At column 29, line 27, please delete "polarized$^{129}$Xe" and insert -- polarized $^{129}$Xe --, therefore.

At column 31, line 5, please delete "HI" and insert -- H1 --, therefore.

At column 34, line 41, in Claim 12, please delete "coupled" and insert -- coupled to --, therefore.

At column 36, line 4, in Claim 21, please delete "coupled" and insert -- coupled to --, therefore.

Signed and Sealed this

Ninth Day of June, 2009

JOHN DOLL
*Acting Director of the United States Patent and Trademark Office*